(12) United States Patent
Primiano et al.

(10) Patent No.: US 7,235,403 B2
(45) Date of Patent: Jun. 26, 2007

(54) REAGENTS AND METHODS FOR IDENTIFYING GENE TARGETS FOR TREATING CANCER

(75) Inventors: Thomas Primiano, Chicago, IL (US); Bey-Dih Chang, Lombard, IL (US); Igor B. Roninson, Wilmette, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 255 days.

(21) Appl. No.: 10/199,820

(22) Filed: Jul. 19, 2002

(65) Prior Publication Data
US 2003/0180739 A1 Sep. 25, 2003

Related U.S. Application Data

(60) Provisional application No. 60/306,730, filed on Jul. 20, 2001.

(51) Int. Cl.
*C12Q 1/68* (2006.01)
*C12Q 1/00* (2006.01)
*G01N 33/53* (2006.01)

(52) U.S. Cl. ............... 436/6; 435/7.1; 435/4; 435/29

(58) Field of Classification Search ............ 435/6, 435/7.1, 320.1, 325
See application file for complete search history.

(56) References Cited

U.S. PATENT DOCUMENTS

| | | | |
|---|---|---|---|
| 5,217,889 A | 6/1993 | Roninson et al. | 435/6 |
| 5,654,168 A | 8/1997 | Bujard et al. | 435/69.1 |
| 5,665,550 A | 9/1997 | Roninson et al. | 435/6 |
| 5,753,432 A | 5/1998 | Gudkov et al. | 435/6 |
| 5,811,234 A | 9/1998 | Roninson et al. | 435/6 |
| 5,851,796 A | 12/1998 | Schatz | 435/69.1 |
| 5,866,328 A | 2/1999 | Bensimon et al. | 435/6 |
| 5,942,389 A | 8/1999 | Kirschling et al. | 435/6 |
| 5,968,773 A | 10/1999 | Heddle et al. | 435/69.1 |
| 6,043,340 A | 3/2000 | Gudkov et al. | 530/300 |
| 6,060,134 A | 5/2000 | Mesch | 428/22 |
| 6,083,745 A | 7/2000 | Gudkov et al. | 435/325 |
| 6,083,746 A | 7/2000 | Gudkiv et al. | 435/325 |
| 6,197,521 B1 | 3/2001 | Roninson et al. | 435/6 |
| 6,268,134 B1 | 7/2001 | Roninson et al. | 435/6 |
| 6,281,011 B1 | 8/2001 | Roninson et al. | 435/325 |
| 6,326,488 B1 | 12/2001 | Roninson et al. | 536/24.5 |

FOREIGN PATENT DOCUMENTS

WO    WO/01 38532    5/2001

OTHER PUBLICATIONS

Araki et al., "Identification of Genes Induced in Peripheral Nerve after Injury" *J. Biol. Chem.* 276:34131-41 (Sep. 7, 2001).
Barnes and Gillett "Cyclin D1 in breast cancer" *Breast Cancer Res. Treat.* 52:1-15 (1998).
Castets et al., "Zinedin, SG2NA, and Striatin Are Calmodulin-binding, WD Repeat Proteins Principally Expressed in the Brain" *J. Biol. Chem.* 275:19970-77 (2000).
Chang et al., "Role of p53 and p21[wafl/cip1] in senescence-like terminal proliferation arrest induced in human tumor cells by chemotherapeutic drugs" *Oncogene* 18:4808-18 (1999).
Dahme et al., "Disruption of the mouse L1 gene leads to malformations of the nervous system" *Nat. Genet.* 17:346-349 (1997).
Denis et al., "A mouse model of severe von Willebrand disease: Defects in hemostasis and thrombosis" *Proc. Natl. Acad. Sci. USA* 95:9524-29 (1998).
Fruchtel & Jung, Organic Chemistry on Solid Supports: *Angew. Chem. Int. Ed. Engl.* 35:17-42 (1996).
Gallop et al., "Applications of Combinatorial Technologies to Drug Discovery. 1. Background and Peptide Combination Libraries" *J. Med. Chem.* 37:1233-51 (Apr. 29, 1994).
Gerwin et al., "Prolonged Eosinophil Accumulation in Allergic Lung Interstitium of ICAM-2-Deficient Mice Results in Extended Hyperresponsiveness" *Immunity* 10:9-19 (1999).
Gudkov et al., "Cloning mammalian genes by expression selection of genetic suppressor elements: Association of kinesin with drug resistance and cell immortalization" *Proc. Natl. Sci. USA* 91:3744-48 (1994).
Hettmann et al., "Microphthalmia Due to p53-Mediated Apoptosis of Anterior Lens Epithelial Cells in Mice Lacking the CREB-2 Transcription Factor" *Dev. Biol.* 222-110-23 (2000).
Izumoto et al., "Gene Expression of Neural Cell Adhesion Molecule L1 Malignant Gliomas and Biological Significance of L1 in Glioma Invasion" *Cancer Research* 56:1440-44 (Mar. 15, 1996).
Jacquemier et al., "Expression of the FGFR1 Gene in Human Breast-Carcinoma Cells" *Int. J. Cancer* 59:373-378 (1994).
Jameel et al., "Clinical and Biological Significance of HSP89 Alpha in Human Breast Cancer" *Int. J. Cancer* 50:409-415 (1992).
Kent et al., "Chemical Synthesis of Peptides and Proteins" *Ann. Rev. Biochem.* 57:957-89 (1988).
McPherson et al., "Current approaches to marcromolecular crystallization" *Eur. J. Biochem.* 189:1-124.
Munster et al., "Inhibition of Heat Shock Protein 90 Function by Ansamycins Causes the Morphological and Functional Differentiation of Breast Cancer Cells" *Cancer Res.* 61:2945-52 (2001).
Munster et al., "Modulation of Hsp90 Function by Ansamycins Sensitizes Breast Cancer Cells to Chemotherapy-induced Apoptosis in an RB-and Schedule-dependent Manner" *Clin. Cancer Res.* 2228-36 (2001).
O'Conner "Mammalian $G_1$ and $G_2$ Phase Checkpoints" *Cancer Surv.* 29:151-182 (1997).
Patanjali et al., "Constuction of a uniform-abundance (normalized) cDNA library" *Proc. Natl. Acad. Sci. USA* 88:1943-47 (1991).
Pestov et al., "Genetic selection of growth-inhibitory sequences in mammalian cells" *Proc. Natl. Acad. Sci. USA* 91:12549-53 (1994).
Pestov et al., "Isolation of growth suppressors from a cDNA expression library" *Oncogene* 17:13187-3197.
Peters et al., "Activation of cellular gene by mouse mammalry tumor virus may occur early in mammary tumour development" *Nature* 309:273-275 (1984).
Pihan et al., "The mitotic machinery as a source of genetic instability in cancer" *Semin. Cancer Biol.* 9:289-302 (1999).
Scolnick et al., "*Chfr* defines a mitotic stress checkpoint that delays entry into metaphase" *Nature* 406:430-435 (2000).
Talukder et al., "Heregulin Induces Expression, DNA Binding Activity, and Transactivating Functions of Basic Leucine Zipper Activating Transcription Factor $4^1$ " *Cancer Res.* 60:276-281 (2000).
Tanaka et al., "Targeted disruption of ATF4 discloses its essential role on the formation eye lens fibres" *Genes Cells* 3:801-810 (1998).
Thompson & Ellman, "Synthesis and Applications of Small Molecule Libraries" *Chem. Rev.* 96:555-6000 (1996).
Torres and Horwitz "Mechanisms of Taxol-induced Cell Death Are Concentration Dependent" *Cancer Res.* 58:3620-3626 (1998).

*Primary Examiner*—James Martinell
(74) *Attorney, Agent, or Firm*—McDonnell Boehnen Hulbert & Berghoff

(57) ABSTRACT

The invention provides methods and reagents for identifying mammalian genes necessary for tumor cell growth as targets for developing drugs that inhibit expression of said genes and inhibit tumor cell growth thereby.

14 Claims, 7 Drawing Sheets

| Library-transduced cells | -IPTG | +IPTG |
|---|---|---|
| G418-selected |  | |
| One round BrdU |  | |
| Two rounds BrdU |  | |

A. Cell morphology no IPTG 4 days IPTG

B. Mitotic catastrophe in IPTG-treated cells

Abnormal mitoses

Micronucleated cells

SEQUENCE LISTING

<160> NUMBER OF SEQ ID NOS: 314

<210> SEQ ID NO 1
<211> LENGTH: 25

```
<212> TYPE: DNA
<213> ORGANISM: Homo Sapiens
<220> FEATURE:
<221> NAME/KEY: misc_feature
<222> LOCATION: (18)..(25)
<223> OTHER INFORMATION: n stands for a, c, t, or g

<400> SEQUENCE: 1
ggatcctcac tcactcannn nnnnn                                          25

<210> SEQ ID NO 2
<211> LENGTH: 38
<212> TYPE: DNA
<213> ORGANISM: Homo Sapiens

<400> SEQUENCE: 2
gtacctgagt tataggatcc ctgccatgcc atgccatg                            38

<210> SEQ ID NO 3
<211> LENGTH: 24
<212> TYPE: DNA
<213> ORGANISM: Homo Sapiens

<400> SEQUENCE: 3
cctagggacg gtacggtacg gtac                                           24

<210> SEQ ID NO 4
<211> LENGTH: 183
<212> TYPE: DNA
<213> ORGANISM: Homo Sapiens

<400> SEQUENCE: 4
gccgctagag gtgaaattcc ttggaccggc gcaagacgga ccagagcgaa agcatttgcc    60
aagaatgttt tcattaatca agaacgaaag tcggaggttc gaagacgatc agataccgtc   120
gtagttccga ccataaacga tgccgaccgg cgatgcggcg gcgttattcc catgacccgc   180
cgg                                                                 183

<210> SEQ ID NO 5
<211> LENGTH: 117
<212> TYPE: DNA
<213> ORGANISM: Homo Sapiens

<400> SEQUENCE: 5
ccggacacgg acaggattga cagattgata gctctttctc gattccgtgg gtggtggtgc    60
atggccgttc ttagttggtg gagcgatttg tctggttaat tccgataacg aacgaga      117

<210> SEQ ID NO 6
<211> LENGTH: 92
<212> TYPE: DNA
<213> ORGANISM: Homo Sapiens

<400> SEQUENCE: 6
caaagattaa gccatgcatg tctaagtacg cacggccggt acagtgaaac tgcgaatggc    60
tcattaaatc agttatggtt cctttggtcg ct                                  92

<210> SEQ ID NO 7
<211> LENGTH: 69
<212> TYPE: DNA
<213> ORGANISM: Homo Sapiens

<400> SEQUENCE: 7
```

```
cggacacgga caggattgac agattgatag ctctttctcg attccgtggg tggtggtgca      60
tggccgttc                                                              69

<210> SEQ ID NO 8
<211> LENGTH: 65
<212> TYPE: DNA
<213> ORGANISM: Homo Sapiens

<400> SEQUENCE: 8
ctgccagtag catatgcttg tctcaaagat taagccatgc atgtctaagt acgcacggcc      60
ggtac                                                                  65

<210> SEQ ID NO 9
<211> LENGTH: 57
<212> TYPE: DNA
<213> ORGANISM: Homo Sapiens

<400> SEQUENCE: 9
taagtacgca cggccggtac agtgaaactg cgaatggctc attaaatcag ttatggt         57

<210> SEQ ID NO 10
<211> LENGTH: 44
<212> TYPE: DNA
<213> ORGANISM: Homo Sapiens

<400> SEQUENCE: 10
cggagaggga gcctgagaaa cggctaccac atccaaggaa ggca                       44

<210> SEQ ID NO 11
<211> LENGTH: 41
<212> TYPE: DNA
<213> ORGANISM: Homo Sapiens

<400> SEQUENCE: 11
caaagattaa gccatgcatg tctaagtacg cacggccggt a                          41

<210> SEQ ID NO 12
<211> LENGTH: 35
<212> TYPE: DNA
<213> ORGANISM: Homo Sapiens

<400> SEQUENCE: 12
cggaactgag gccatgatta agagggacgg ccggg                                 35

<210> SEQ ID NO 13
<211> LENGTH: 35
<212> TYPE: DNA
<213> ORGANISM: Homo Sapiens

<400> SEQUENCE: 13
cagattgata gctctttctc gattccgtgg gtggt                                 35

<210> SEQ ID NO 14
<211> LENGTH: 45
<212> TYPE: DNA
<213> ORGANISM: Homo Sapiens

<400> SEQUENCE: 14
aactgcgaat ggctcattaa atcagttatg gttcctttgg tcgct                      45

<210> SEQ ID NO 15
<211> LENGTH: 30
```

<212> TYPE: DNA
<213> ORGANISM: Homo Sapiens

<400> SEQUENCE: 15
aagccatgca tgtctaagta cgcacggccg                              30

<210> SEQ ID NO 16
<211> LENGTH: 118
<212> TYPE: DNA
<213> ORGANISM: Homo Sapiens

<400> SEQUENCE: 16
ccctactgat gatgtgttgt tgccatggta atcctgctca gtacgagagg aaccgcaggt    60
tcagacattt ggtgtatgtg cttggctgag gagccaatgg ggcgaacgta ccatctgt     118

<210> SEQ ID NO 17
<211> LENGTH: 49
<212> TYPE: DNA
<213> ORGANISM: Homo Sapiens

<400> SEQUENCE: 17
gaattcacca agcgttggat tgttcaccca ctaatagggga acgtgagct              49

<210> SEQ ID NO 18
<211> LENGTH: 27
<212> TYPE: DNA
<213> ORGANISM: Homo Sapiens

<400> SEQUENCE: 18
cgcaggttca gacatttggt gtatgtg                                 27

<210> SEQ ID NO 19
<211> LENGTH: 108
<212> TYPE: DNA
<213> ORGANISM: Homo Sapiens

<400> SEQUENCE: 19
cccagctact cgggaggctg aggctggagg atcgcttgag tccaggagtt ctgggctgta    60
gtgcgctatg ccgatcgggt gtccgcacta agttcggcat caatatgg              108

<210> SEQ ID NO 20
<211> LENGTH: 68
<212> TYPE: DNA
<213> ORGANISM: Homo Sapiens

<400> SEQUENCE: 20
ccaggagttc tgggctgtag tgcgctatgc cgatcgggtg tccgcactaa gttcggcatc    60
aatatggt                                                    68

<210> SEQ ID NO 21
<211> LENGTH: 40
<212> TYPE: DNA
<213> ORGANISM: Homo Sapiens

<400> SEQUENCE: 21
ccgggagcgg gggaccacca ggttgcctaa ggagggtga                   40

<210> SEQ ID NO 22
<211> LENGTH: 44
<212> TYPE: DNA
<213> ORGANISM: Homo Sapiens

```
<400> SEQUENCE: 22
gtagtcccag ctactcggga ggctgaggct ggaggatcgc ttga            44

<210> SEQ ID NO 23
<211> LENGTH: 31
<212> TYPE: DNA
<213> ORGANISM: Homo Sapiens

<400> SEQUENCE: 23
ggggaccacc aggttgccta aggagggtg a                           31

<210> SEQ ID NO 24
<211> LENGTH: 86
<212> TYPE: DNA
<213> ORGANISM: Homo Sapiens

<400> SEQUENCE: 24
gctgtggcac gggtctagga ccaccaactt tgctgggatc ctgtcccagg gtcttcggat    60
agccccgcct gaagcgcccg tgacag                                86

<210> SEQ ID NO 25
<211> LENGTH: 83
<212> TYPE: DNA
<213> ORGANISM: Homo Sapiens

<400> SEQUENCE: 25
gaccctcccc tgagcagact gtaggccacc tcgatgtcca gcaggttgtc aagcatttcc    60
accttggcct gcacactgtc tgc                                   83

<210> SEQ ID NO 26
<211> LENGTH: 54
<212> TYPE: DNA
<213> ORGANISM: Homo Sapiens

<400> SEQUENCE: 26
ttcacactga ccaaccgccg aggacagtcg gaccggcgac ctctcaaccc agcc          54

<210> SEQ ID NO 27
<211> LENGTH: 76
<212> TYPE: DNA
<213> ORGANISM: Homo Sapiens

<400> SEQUENCE: 27
acaccttcga attaagcaca ttcctcgatt ccagcaaagc accgcaacat gaccgaaatg    60
agcttcctga gcagcg                                           76

<210> SEQ ID NO 28
<211> LENGTH: 50
<212> TYPE: DNA
<213> ORGANISM: Homo Sapiens

<400> SEQUENCE: 28
gacaccttcg aattaagcac attcctcgat tccagcaaag caccgcaaca              50

<210> SEQ ID NO 29
<211> LENGTH: 55
<212> TYPE: DNA
<213> ORGANISM: Homo Sapiens

<400> SEQUENCE: 29
ccttagaatt aagcacattc ctcgattcca gcaaagcgcc gcaacatgac ggaaa         55
```

```
<210> SEQ ID NO 30
<211> LENGTH: 38
<212> TYPE: DNA
<213> ORGANISM: Homo Sapiens

<400> SEQUENCE: 30
gaattaagca ctttcctcga gtccagcaaa gccccgca                            38

<210> SEQ ID NO 31
<211> LENGTH: 46
<212> TYPE: DNA
<213> ORGANISM: Homo Sapiens

<400> SEQUENCE: 31
cgctgctcag caagctctgt tcggtcatgt tgcggtgctt tgctgg                   46

<210> SEQ ID NO 32
<211> LENGTH: 57
<212> TYPE: DNA
<213> ORGANISM: Homo Sapiens

<400> SEQUENCE: 32
ccagcagcaa tggcagtgac ggcgttggcg gcgcggacgt ggcttggcgt gtggggc       57

<210> SEQ ID NO 33
<211> LENGTH: 85
<212> TYPE: DNA
<213> ORGANISM: Homo Sapiens

<400> SEQUENCE: 33
ccgggacgag gagtcgaccc ggagcgagga ggtgaccagg gaggaaatgg cggcagctgg    60
gctcaccgtg actgtcaccc acagc                                         85

<210> SEQ ID NO 34
<211> LENGTH: 58
<212> TYPE: DNA
<213> ORGANISM: Homo Sapiens

<400> SEQUENCE: 34
ggaggtgacc agggaggaaa tggcggcagc tgggctcacc gtgactgtca cccacagc     58

<210> SEQ ID NO 35
<211> LENGTH: 62
<212> TYPE: DNA
<213> ORGANISM: Homo Sapiens

<400> SEQUENCE: 35
gccaagagtc agcctgacat ggccattatg gccgtcaaca cctttgtgaa ggactgtgag   60
ga                                                                  62

<210> SEQ ID NO 36
<211> LENGTH: 49
<212> TYPE: DNA
<213> ORGANISM: Homo Sapiens

<400> SEQUENCE: 36
gcctgacatg gccattatgg ccgtcaacac ctttgtgaag gactgtgag               49

<210> SEQ ID NO 37
<211> LENGTH: 209
<212> TYPE: DNA
```

```
<213> ORGANISM: Homo Sapiens

<400> SEQUENCE: 37
gccagggaca ccatgctacg gccttgacag cccccttgatg ctgggtgaat gtctgcagag        60
gaacccagcc accctctcca ggagcactgg gccacacatt gaccaagtta tcattaccac       120
cactggccaa atgtcgtcca tctggggccc agcgcagccc acacacttcc tggctgtggc       180
cactcagtgt ggccacatgg tgttctgct                                         209

<210> SEQ ID NO 38
<211> LENGTH: 41
<212> TYPE: DNA
<213> ORGANISM: Homo Sapiens

<400> SEQUENCE: 38
gccccagcca cctccgaggg ccagagcatg cgctgtaaac c                            41

<210> SEQ ID NO 39
<211> LENGTH: 96
<212> TYPE: DNA
<213> ORGANISM: Homo Sapiens

<400> SEQUENCE: 39
ctaccaggag agccctgggc tggaggctga gctgcatccc tgctccccac atggaggacc        60
caacaggagg ccgtggctct gatgctgagc gaagct                                  96

<210> SEQ ID NO 40
<211> LENGTH: 47
<212> TYPE: DNA
<213> ORGANISM: Homo Sapiens

<400> SEQUENCE: 40
agatctctct gcttaaggag cttaaccatc ctaatattgt caagctg                      47

<210> SEQ ID NO 41
<211> LENGTH: 58
<212> TYPE: DNA
<213> ORGANISM: Homo Sapiens

<400> SEQUENCE: 41
tacacccatg aggtggtgac cctgtggtac cgagctcctg aaatcctcct gggctgca          58

<210> SEQ ID NO 42
<211> LENGTH: 112
<212> TYPE: DNA
<213> ORGANISM: Homo Sapiens

<400> SEQUENCE: 42
cactgccatc tcgaccagtc cggacctgca gtggctggtg cagcccgccc tcgtctcctc        60
tgtggcccca tcgcagacca gagcccctca ccctttcgga gtccccgccc cc               112

<210> SEQ ID NO 43
<211> LENGTH: 72
<212> TYPE: DNA
<213> ORGANISM: Homo Sapiens

<400> SEQUENCE: 43
cactcacccg cagactcctt ctccagcatg ggctcgcctg tcaacgcgca ggacttctgc        60
acggacctgg cc                                                            72
```

```
<210> SEQ ID NO 44
<211> LENGTH: 66
<212> TYPE: DNA
<213> ORGANISM: Homo Sapiens

<400> SEQUENCE: 44
agcgaacgag cagtgaccgt gctcctaccc agctctgctt cacagcgccc acctgtctcc      60
gcccct                                                                66

<210> SEQ ID NO 45
<211> LENGTH: 66
<212> TYPE: DNA
<213> ORGANISM: Homo Sapiens

<400> SEQUENCE: 45
gcccgagctg gtgcattaca gagaggagaa acacatcttc cctagagggt tcctgtagac      60
ctaggg                                                                66

<210> SEQ ID NO 46
<211> LENGTH: 166
<212> TYPE: DNA
<213> ORGANISM: Homo Sapiens

<400> SEQUENCE: 46
gaggcagggt gaaggcctcc tcagactccg ggtggcaac ctctggcagg cccccagtca       60
gatcaaggga agccacagac atctcttctg ggaagcccag gtcatcaggg atcttgcagg     120
cgggtcggtg agctgccagg atgaactcta gtttttcctt ctcctt                    166

<210> SEQ ID NO 47
<211> LENGTH: 35
<212> TYPE: DNA
<213> ORGANISM: Homo Sapiens

<400> SEQUENCE: 47
taagatggct gcagccaaat gccgcaaccg gagga                                 35

<210> SEQ ID NO 48
<211> LENGTH: 108
<212> TYPE: DNA
<213> ORGANISM: Homo Sapiens

<400> SEQUENCE: 48
gcgatttcgg gctagccaga gacatcagga atgattcgaa ttacgtggtc aaaggaaatg      60
cacgactgcc cgtgaagtgg atggcaccag agagcatttt cagctgcg                 108

<210> SEQ ID NO 49
<211> LENGTH: 116
<212> TYPE: DNA
<213> ORGANISM: Homo Sapiens

<400> SEQUENCE: 49
cccagggatg ccggtcgact ccaagttcta caagatgatc aaggaaggct tccggatggt      60
cagcccggag cacgcgcctg ccgaaatgta tgacgtcatg aagacttgct gggacg        116

<210> SEQ ID NO 50
<211> LENGTH: 71
<212> TYPE: DNA
<213> ORGANISM: Homo Sapiens

<400> SEQUENCE: 50
```

```
aacggggcat cggaagtctg gtcacgctaa gaagaccgag gctgagaagg aacaagccag    60
gggaagcgtg a                                                         71

<210> SEQ ID NO 51
<211> LENGTH: 69
<212> TYPE: DNA
<213> ORGANISM: Homo Sapiens

<400> SEQUENCE: 51
gctggtttgg aggtcctgtg gtcatgtacg agactgtcac cagttaccgc gctctgtttg    60
aaacatgtc                                                            69

<210> SEQ ID NO 52
<211> LENGTH: 85
<212> TYPE: DNA
<213> ORGANISM: Homo Sapiens

<400> SEQUENCE: 52
tgagaaggaa caagccaggg gaagcgtgaa caatgatgct ctgctctggg ctgccgctcg    60
ggcttctgta caactgacct ggttt                                          85

<210> SEQ ID NO 53
<211> LENGTH: 80
<212> TYPE: DNA
<213> ORGANISM: Homo Sapiens

<400> SEQUENCE: 53
gaacaagcca gggaagcgtg aacaatgatg ctctgctctg gctgccgct cgggcttctg    60 tacaactgac ctggtttctc                                                80

<210> SEQ ID NO 54
<211> LENGTH: 66
<212> TYPE: DNA
<213> ORGANISM: Homo Sapiens

<400> SEQUENCE: 54
aagcccagcc acagattgcc acattagccc aggtatctat gccagcagct catgcaacat    60
catctg                                                               66

<210> SEQ ID NO 55
<211> LENGTH: 108
<212> TYPE: DNA
<213> ORGANISM: Homo Sapiens

<400> SEQUENCE: 55
tgcggaagat cgtcgccacc tggatgctgg aggtctgcga ggaacagaag tgcgaggagg    60
aggtcttccc gctggccatg aactacctgg accgcttcct gtcgctgg               108

<210> SEQ ID NO 56
<211> LENGTH: 23
<212> TYPE: DNA
<213> ORGANISM: Homo Sapiens

<400> SEQUENCE: 56
agaacatgga ccccaaggcc gcc                                            23

<210> SEQ ID NO 57
<211> LENGTH: 108
<212> TYPE: DNA
<213> ORGANISM: Homo Sapiens
```

```
<400> SEQUENCE: 57
tgcggaagat cgtcgccacc tggatgctgg aggtctgcga ggaacagaag tgcgaggagg    60
aggtcttccc gctggccatg aactacctgg accgcttcct gtcgctgg              108

<210> SEQ ID NO 58
<211> LENGTH: 113
<212> TYPE: DNA
<213> ORGANISM: Homo Sapiens

<400> SEQUENCE: 58
cacagcttct cggccgtcag ggggatggtc tccttcatct tagaggccac gaacatgcaa    60
gtggccccca gcagctgcag gcggctcttt tcacgggct ccagcgacag gaa         113

<210> SEQ ID NO 59
<211> LENGTH: 169
<212> TYPE: DNA
<213> ORGANISM: Homo Sapiens

<400> SEQUENCE: 59
gcggcactgt gcctacctct aagccaagat cacagcatgt gaggaagaca gtggacatct    60
gctttatgct ggacccagta agatgaggaa gtcgggcagt acacaggaag aggagccagg   120
cccttgtacc tatgggattg acaggactg cagttggctc tggacctgc              169

<210> SEQ ID NO 60
<211> LENGTH: 159
<212> TYPE: DNA
<213> ORGANISM: Homo Sapiens

<400> SEQUENCE: 60
gcctacctct aagccaagat cacagcatgt gaggaagaca gtggacatct gctttatgct    60
ggacccagta agatgaggaa gtcgggcagt acacaggaag aggagccagg cccttgtacc   120
tatgggattg acaggactg cagttggctc tggacctgc                         159

<210> SEQ ID NO 61
<211> LENGTH: 49
<212> TYPE: DNA
<213> ORGANISM: Homo Sapiens

<400> SEQUENCE: 61
ggccaaatcc aagcaggcta tcttagcggc acagagacga ggaggagat              49

<210> SEQ ID NO 62
<211> LENGTH: 79
<212> TYPE: DNA
<213> ORGANISM: Homo Sapiens

<400> SEQUENCE: 62
ggcgaggagg cgctgatgat gagcgatcat cctggcgtaa tgctgatgat gaccggggtc    60
ccaggcgagg gttggatga                                               79

<210> SEQ ID NO 63
<211> LENGTH: 25
<212> TYPE: DNA
<213> ORGANISM: Homo Sapiens

<400> SEQUENCE: 63
gcagcgttgg gcccatgcag gacgc                                        25
```

<210> SEQ ID NO 64
<211> LENGTH: 25
<212> TYPE: DNA
<213> ORGANISM: Homo Sapiens

<400> SEQUENCE: 64
cagcttcagg cagaaacaga accaa                                  25

<210> SEQ ID NO 65
<211> LENGTH: 66
<212> TYPE: DNA
<213> ORGANISM: Homo Sapiens

<400> SEQUENCE: 65
agatctcgcc ggctttacgt tcacctcggt gtctgcagca ccctccgctt cctctcctag   60
gcgacg                                                            66

<210> SEQ ID NO 66
<211> LENGTH: 47
<212> TYPE: DNA
<213> ORGANISM: Homo Sapiens

<400> SEQUENCE: 66
cgccggcttt acgttcacct cggtgtctgc agcaccctcc gcttcct               47

<210> SEQ ID NO 67
<211> LENGTH: 84
<212> TYPE: DNA
<213> ORGANISM: Homo Sapiens

<400> SEQUENCE: 67
cgcactatga agatcactct gtggcagacg ctgccatgga gcagtacata ctgtacctgg   60
tggagcatga ggagtaccag ctgt                                         84

<210> SEQ ID NO 68
<211> LENGTH: 61
<212> TYPE: DNA
<213> ORGANISM: Homo Sapiens

<400> SEQUENCE: 68
tgctgcaagt ctcttctcct gtggattgac atgggcctga ggactgtgag tgattttgcc   60
a                                                                  61

<210> SEQ ID NO 69
<211> LENGTH: 109
<212> TYPE: DNA
<213> ORGANISM: Homo Sapiens

<400> SEQUENCE: 69
tggcacagcc cccctgctgg cacagctctg gggagtgctg ccccaggatg ggagagaatg   60
cagtacctgg ctacaaactt ctctgtggca gctccacaga tgaggtctt             109

<210> SEQ ID NO 70
<211> LENGTH: 48
<212> TYPE: DNA
<213> ORGANISM: Homo Sapiens

<400> SEQUENCE: 70
gacagtcacc ttcaacctca agcagcggtc ttcatgctgg tggatggg              48

<210> SEQ ID NO 71
<211> LENGTH: 87
<212> TYPE: DNA
<213> ORGANISM: Homo Sapiens

<400> SEQUENCE: 71
gccacagctc aagtcaggcg agctggccaa acgcagtgag cggcgggctg aggcagagaa    60
gcagctgcag caggctcagg ctgctgg    87

<210> SEQ ID NO 72
<211> LENGTH: 60
<212> TYPE: DNA
<213> ORGANISM: Homo Sapiens

<400> SEQUENCE: 72
ggcagaggcc agctgtgctg ccctggtgaa ggctggcaaa gtctatgctg cggctaccga    60

<210> SEQ ID NO 73
<211> LENGTH: 44
<212> TYPE: DNA
<213> ORGANISM: Homo Sapiens

<400> SEQUENCE: 73
gccacagctc aagtcaggcg agctggccaa acgcagtgag cggc    44

<210> SEQ ID NO 74
<211> LENGTH: 70
<212> TYPE: DNA
<213> ORGANISM: Homo Sapiens

<400> SEQUENCE: 74
gcgacctgga caaacgcatt gagcggcggc ctgaggcaga aagcagctg tatcatgctc    60 aagctgctgg    70

<210> SEQ ID NO 75
<211> LENGTH: 70
<212> TYPE: DNA
<213> ORGANISM: Homo Sapiens

<400> SEQUENCE: 75
tggcgaaacg cgggccgacc acagggacgc tgctgcccag ggtcctgctg gccctggtgg    60
tggccctggc    70

<210> SEQ ID NO 76
<211> LENGTH: 165
<212> TYPE: DNA
<213> ORGANISM: Homo Sapiens

<400> SEQUENCE: 76
ggtaacagtg tctgctgact ccagtgcatc catgaactct ggggttcttc tggttcggcc    60
atcacggctc tcctccagtg ggactcccat gctagcaggg gtctctgagt atgagcttcc    120
cgaagaccct cgcgggagct gcctcgggac agactggtct taggc    165

<210> SEQ ID NO 77
<211> LENGTH: 135
<212> TYPE: DNA
<213> ORGANISM: Homo Sapiens

<400> SEQUENCE: 77
ggaggaactt ttcaagctgc tgaaggaggg tcaccgcatg acaagccca gtaactgcac    60

```
caacgagctg tacatgatga tgcgggactg ctggcatgca gtgccctcac agagacccac      120
cttcaagcag ctggt                                                        135

<210> SEQ ID NO 78
<211> LENGTH: 99
<212> TYPE: DNA
<213> ORGANISM: Homo Sapiens

<400> SEQUENCE: 78
ggtaccaaga agagtgactt ccacagccag atggctgtgc acaagctggc caagagcatc      60
ctctgcgcag acaggtaaca gtgtctgctg actccagtg                             99

<210> SEQ ID NO 79
<211> LENGTH: 68
<212> TYPE: DNA
<213> ORGANISM: Homo Sapiens

<400> SEQUENCE: 79
tcctcacatc ccagacgatg ggcggccagg cagagacgct cctcacttcc cagacggggt      60
agcggccg                                                               68

<210> SEQ ID NO 80
<211> LENGTH: 53
<212> TYPE: DNA
<213> ORGANISM: Homo Sapiens

<400> SEQUENCE: 80
tcctcacatc ccagacgatg ggcggccagg cagagacgct cctcacttcc cag             53

<210> SEQ ID NO 81
<211> LENGTH: 94
<212> TYPE: DNA
<213> ORGANISM: Homo Sapiens

<400> SEQUENCE: 81
agaaagtgag gaccctcagg aggctgcagg ccagtgagtc agcaaatgaa gagattcccg      60
aaccccgaat cagtgattcg gaaagtgagg atcc                                  94

<210> SEQ ID NO 82
<211> LENGTH: 49
<212> TYPE: DNA
<213> ORGANISM: Homo Sapiens

<400> SEQUENCE: 82
ctaacacagc gagggactca acacgctgat tctcctcctg cctctcccg                  49

<210> SEQ ID NO 83
<211> LENGTH: 76
<212> TYPE: DNA
<213> ORGANISM: Homo Sapiens

<400> SEQUENCE: 83
ggcggggctg gacaatgccc agcgctctgt ctcaagccca tcagcattgc tggggcttc      60 tacggtgagg atcccc                                                      76

<210> SEQ ID NO 84
<211> LENGTH: 34
<212> TYPE: DNA
<213> ORGANISM: Homo Sapiens

<400> SEQUENCE: 84
```

```
ggtgactcct gctccaggac gctaggatag gtga                                34

<210> SEQ ID NO 85
<211> LENGTH: 58
<212> TYPE: DNA
<213> ORGANISM: Homo Sapiens

<400> SEQUENCE: 85
cagagcccca aaacgctggg cagagttgac aggacccaaa tgctaaagtt gtggaggg      58

<210> SEQ ID NO 86
<211> LENGTH: 121
<212> TYPE: DNA
<213> ORGANISM: Homo Sapiens

<400> SEQUENCE: 86
tggggagacc cggagacggt ggctggggtg tcctcagccc gggagagctg agtcagccgc    60
gccccgcaca cagcatactt aggagccaag gacttggacc tcgcttctcg ccggtacgcg   120
a                                                                   121

<210> SEQ ID NO 87
<211> LENGTH: 91
<212> TYPE: DNA
<213> ORGANISM: Homo Sapiens
<220> FEATURE:
<221> NAME/KEY: misc_feature
<222> LOCATION: (9)..(9)
<223> OTHER INFORMATION: n stands for a, c, t, or g
<220> FEATURE:
<221> NAME/KEY: misc_feature
<222> LOCATION: (17)..(17)
<223> OTHER INFORMATION: n stands for a, c, t, or g

<400> SEQUENCE: 87
acccctggna acatggnaaa tataaaacaa cttggtgttt ttgaaaaacc gcaaagcgtt    60
atggtgtgga tgtaacacag gggtgtggtg t                                  91

<210> SEQ ID NO 88
<211> LENGTH: 61
<212> TYPE: DNA
<213> ORGANISM: Homo Sapiens

<400> SEQUENCE: 88
tggaggaaac cccgtgtctg cggagcggct gtagcctgtg agcagcgaga tccagggaca    60
g                                                                   61

<210> SEQ ID NO 89
<211> LENGTH: 53
<212> TYPE: DNA
<213> ORGANISM: Homo Sapiens

<400> SEQUENCE: 89
cagctaccca gaagtctgag gcaggagaaa tgctggaacc cgggaggcag agg           53

<210> SEQ ID NO 90
<211> LENGTH: 82
<212> TYPE: DNA
<213> ORGANISM: Homo Sapiens

<400> SEQUENCE: 90
cagcgatccg tccagcagat gacgaatatc gacggccatt tccggcatac cgagctgttg    60
```
cataatgccc gcagactgtg ct                                                    82

<210> SEQ ID NO 91
<211> LENGTH: 170
<212> TYPE: DNA
<213> ORGANISM: Homo Sapiens

<400> SEQUENCE: 91
cggaagagct cacaatgctc atttcgcgtc tcgctcgggt gttgtgctgt tctttaatac         60
tgtgggcaat tcaggtgtgt cgcttagaaa acggaggtac tcaatggagt cctcaacaat        120
gaggggccct gttcatggct ttgtgttggc cgttcgttcc acatgttctt                   170

<210> SEQ ID NO 92
<211> LENGTH: 79
<212> TYPE: DNA
<213> ORGANISM: Homo Sapiens

<400> SEQUENCE: 92
cgatgattat tttcttggca aagttttag cagaacgtca aaaattgatt acatctttta          60
aacgtggttt attaccggc                                                      79

<210> SEQ ID NO 93
<211> LENGTH: 81
<212> TYPE: DNA
<213> ORGANISM: Homo Sapiens

<400> SEQUENCE: 93
agagcgaggc gtgaagtcca cacgcccagc cccgtcgcag tgtggttgcc gagcaaggct         60
acgtctgcgg cgcgtgcggt a                                                   81

<210> SEQ ID NO 94
<211> LENGTH: 98
<212> TYPE: DNA
<213> ORGANISM: Homo Sapiens

<400> SEQUENCE: 94
ccgggatgaa gtgacccagc agaaatacca gagaccggag acggaatggc ccagggtcag         60
cctccacccg gaaccggagg atgcagcgaa gacgtctc                                 98

<210> SEQ ID NO 95
<211> LENGTH: 86
<212> TYPE: DNA
<213> ORGANISM: Homo Sapiens

<400> SEQUENCE: 95
cctcgctcag gattgcttcc cgcggtgcct cccgcggctg cacggaaggc cacgaaccga         60
caacttgcac agcagccatc ttttct                                              86

<210> SEQ ID NO 96
<211> LENGTH: 63
<212> TYPE: DNA
<213> ORGANISM: Homo Sapiens

<400> SEQUENCE: 96
cgcgcgcagc tccccgcccc tcgagccgag gccgaggggg ctgatggccg ccgccgggcc         60
gag                                                                       63

<210> SEQ ID NO 97
<211> LENGTH: 62

-continued

```
<212> TYPE: DNA
<213> ORGANISM: Homo Sapiens

<400> SEQUENCE: 97
ggaccagcag gaggcagccc tggtggacat ggtgaatgac ggcgtggagg acctccgctg    60
ca                                                                   62

<210> SEQ ID NO 98
<211> LENGTH: 134
<212> TYPE: DNA
<213> ORGANISM: Homo Sapiens

<400> SEQUENCE: 98
tgcctggctg cgtttcccct gctctcagca tatgtggggc gcctcagcgc ccggcccaag    60
ctcaaggcct tcctggcctc ccctgagtac gtgaacttcc ccatcaatgg caacgggaaa   120
cagtgagggt tggg                                                     134

<210> SEQ ID NO 99
<211> LENGTH: 79
<212> TYPE: DNA
<213> ORGANISM: Homo Sapiens

<400> SEQUENCE: 99
gcagggcagc ccctggtaac cagcccagtc aggccccagc cccgtttctt aagaaacttt    60
tagggaccct gcagctctg                                                 79

<210> SEQ ID NO 100
<211> LENGTH: 77
<212> TYPE: DNA
<213> ORGANISM: Homo Sapiens

<400> SEQUENCE: 100
cggaccagga ccaggaagta actttagagg aggatctgat ggatatggca gtggacgtgg    60
atttggggat ggctata                                                   77

<210> SEQ ID NO 101
<211> LENGTH: 158
<212> TYPE: DNA
<213> ORGANISM: Homo Sapiens

<400> SEQUENCE: 101
caggcctgga aaggatgagg cctggtgcct acagcacagg ctacggggc tacgaggagt     60 acagtggcct cagtgatggc tacggcttca ccaccgacct gttcgggaga gacctcagct   120
actgtctctc cggaatgtat gaccacagat acgccgac                           158

<210> SEQ ID NO 102
<211> LENGTH: 42
<212> TYPE: DNA
<213> ORGANISM: Homo Sapiens

<400> SEQUENCE: 102
ggtgcgggtg aagatggcgg cagccgaggc cgcgaactgc at                       42

<210> SEQ ID NO 103
<211> LENGTH: 52
<212> TYPE: DNA
<213> ORGANISM: Homo Sapiens

<400> SEQUENCE: 103
```
caaggaccag gtagctaact cagcctttgt ggaacgtctt cggaaacatg gc        52

<210> SEQ ID NO 104
<211> LENGTH: 36
<212> TYPE: DNA
<213> ORGANISM: Homo Sapiens

<400> SEQUENCE: 104
ccaaggacca ggtagctaac tcagcctttg tggaac                         36

<210> SEQ ID NO 105
<211> LENGTH: 101
<212> TYPE: DNA
<213> ORGANISM: Homo Sapiens

<400> SEQUENCE: 105
ggcagccctt ggctggtccc tgcgagcccg tggagactgc cagagatgtc ctctttcggt    60
tacaggaccc tgactgtggc cctcttcacc ctgatctgct g                       101

<210> SEQ ID NO 106
<211> LENGTH: 64
<212> TYPE: DNA
<213> ORGANISM: Homo Sapiens

<400> SEQUENCE: 106
gagcctgtgt cggacagcca gatggtcatc atagtcacgg tggtgtcggt gttgctgtcc    60
ctgt                                                                64

<210> SEQ ID NO 107
<211> LENGTH: 106
<212> TYPE: DNA
<213> ORGANISM: Homo Sapiens

<400> SEQUENCE: 107
gccgctcact ccccgtaggt gcccatccgc tgctggcgca agtgctggcc gaagatgaag    60
cagagcagga cagatgtcac gaacagggac agcaacaccg acacca                  106

<210> SEQ ID NO 108
<211> LENGTH: 39
<212> TYPE: DNA
<213> ORGANISM: Homo Sapiens

<400> SEQUENCE: 108
gaagctggtg cgcaaggaca ggcttgtcct gagttacgt                          39

<210> SEQ ID NO 109
<211> LENGTH: 62
<212> TYPE: DNA
<213> ORGANISM: Homo Sapiens
<220> FEATURE:
<221> NAME/KEY: misc_feature
<222> LOCATION: (18)..(18)
<223> OTHER INFORMATION: n stands for a, c, t, or g

<400> SEQUENCE: 109
gcggtgccac cgacgggnaa gaagcgctat gacctgtccg cgctggtccg ccatgcagaa    60
cc                                                                  62

<210> SEQ ID NO 110
<211> LENGTH: 124
<212> TYPE: DNA
<213> ORGANISM: Homo Sapiens

```
<220> FEATURE:
<221> NAME/KEY: misc_feature
<222> LOCATION: (26)..(26)
<223> OTHER INFORMATION: n stands for a, c, t, or g

<400> SEQUENCE: 110
ctcctcctcc tcacactcca ccgggngcct caaacaactc cacacatcgc accacgctga    60
tgctctctgg ccagaggact gtcttgctga tctccactgg gcaccatgct gattttccag   120
agcc                                                                124

<210> SEQ ID NO 111
<211> LENGTH: 132
<212> TYPE: DNA
<213> ORGANISM: Homo Sapiens

<400> SEQUENCE: 111
tggggctctg cgcgctcctg ccccggctcg caggtctcaa catatgcact agtggaagtg    60
ccacctcatg tgaagaatgt ctgctaatcc acccaaaatg tgcctggtgc tccaaagagg   120
acttcggaag cc                                                       132

<210> SEQ ID NO 112
<211> LENGTH: 115
<212> TYPE: DNA
<213> ORGANISM: Homo Sapiens

<400> SEQUENCE: 112
ccaaggactg cgtcatgatg ttcacctatg tggagctccc cagtgggaag tccaacctga    60
ccgtcctcag ggagccagag tgtggaaaca ccccaacgc catgaccatc ctcct          115

<210> SEQ ID NO 113
<211> LENGTH: 87
<212> TYPE: DNA
<213> ORGANISM: Homo Sapiens

<400> SEQUENCE: 113
ggccatggcg agtgtcactg cggggaatgc aagtgccatg caggttacat cggggacaac    60
tgtaactgct cgacagacat cagcaca                                        87

<210> SEQ ID NO 114
<211> LENGTH: 91
<212> TYPE: DNA
<213> ORGANISM: Homo Sapiens

<400> SEQUENCE: 114
gtggagctcc ccagtgggaa gtccaacctg accgtcctca gggagccaga gtgtggaaac    60 accccaacg ccatgaccat cctcctggct g                                    91

<210> SEQ ID NO 115
<211> LENGTH: 36
<212> TYPE: DNA
<213> ORGANISM: Homo Sapiens

<400> SEQUENCE: 115
tgaaagatga ccaggaggct gtgctatgtt tctaca                              36

<210> SEQ ID NO 116
<211> LENGTH: 90
<212> TYPE: DNA
<213> ORGANISM: Homo Sapiens
```

```
<400> SEQUENCE: 116
aactccagtg ggcacccaag attcacttgg agccctggcc tccccaccct tgtctttggg    60
ctggctgctt gggggaccaa gaacttgcat                                     90

<210> SEQ ID NO 117
<211> LENGTH: 81
<212> TYPE: DNA
<213> ORGANISM: Homo Sapiens

<400> SEQUENCE: 117
aagagcaagt gccagctgct aagggcttg agtcagagac tctggaagac tcgaagttca    60
agatgtatgt ggagttacat g                                              81

<210> SEQ ID NO 118
<211> LENGTH: 93
<212> TYPE: DNA
<213> ORGANISM: Homo Sapiens

<400> SEQUENCE: 118
tgggcgtcct ccccggagcg ctccgaggtc cgggtgttcg tcacgttgat gctcaggagc    60
aatttccgga cgtctctgct gtactggagc ctg                                 93

<210> SEQ ID NO 119
<211> LENGTH: 90
<212> TYPE: DNA
<213> ORGANISM: Homo Sapiens

<400> SEQUENCE: 119
ggcgcgaacc cggccccccga aggccgccgt ccgggagacg gtgatgctgt tgctgtgcct    60
gggggtcccg accggccgcc cctacaacgt                                     90

<210> SEQ ID NO 120
<211> LENGTH: 53
<212> TYPE: DNA
<213> ORGANISM: Homo Sapiens
<220> FEATURE:
<221> NAME/KEY: misc_feature
<222> LOCATION: (44)..(44)
<223> OTHER INFORMATION: n stands for a, c, t, or g

<400> SEQUENCE: 120
tgtgttctac agttagcttc tctgctggac acctgtatgc ttcnctgtaa tca           53

<210> SEQ ID NO 121
<211> LENGTH: 48
<212> TYPE: DNA
<213> ORGANISM: Homo Sapiens

<400> SEQUENCE: 121
cgggatacgg ccgggcccct ggtggcctct ctctacacga ctacaaac                 48

<210> SEQ ID NO 122
<211> LENGTH: 28
<212> TYPE: DNA
<213> ORGANISM: Homo Sapiens

<400> SEQUENCE: 122
ccctggtggc ctctctctac acgactac                                       28

<210> SEQ ID NO 123
<211> LENGTH: 96
```

<212> TYPE: DNA
<213> ORGANISM: Homo Sapiens

<400> SEQUENCE: 123

```
cctgtccaag aggaggccac agcgctggcc tttccccacg gaggccactg ctgtcccgtc    60
ctctgtatac agttgcaaca cctgggcctc acaggt                              96
```

<210> SEQ ID NO 124
<211> LENGTH: 69
<212> TYPE: DNA
<213> ORGANISM: Homo Sapiens

<400> SEQUENCE: 124

```
tctggatccg tcttcacttc ctgttggcct gagcagtacc aataacacac tggttcacct    60
tggaggcaa                                                            69
```

<210> SEQ ID NO 125
<211> LENGTH: 93
<212> TYPE: DNA
<213> ORGANISM: Homo Sapiens

<400> SEQUENCE: 125

```
ttggggaccc aggagacgac acttggatgt tgtgtggtgg gtaccgaagg cagcgtgtgt    60
atggagctcc tgaaagccgg ccatggggtg ggc                                 93
```

<210> SEQ ID NO 126
<211> LENGTH: 112
<212> TYPE: DNA
<213> ORGANISM: Homo Sapiens

<400> SEQUENCE: 126

```
caggcaatcc ctgagctgga aggcattgaa atcctcaact caagtgccgt gctggtcaag    60
tggcggccgg tggacctggc ccaggtcaag ggccacctcc gcggatacaa tg           112
```

<210> SEQ ID NO 127
<211> LENGTH: 107
<212> TYPE: DNA
<213> ORGANISM: Homo Sapiens

<400> SEQUENCE: 127

```
agtgttcagt ggctggacga ggatgggaca acagtgcttc aggacgaacg cttcttcccc    60
tatgccaatg ggaccctggg cattcgagac ctccaggcca atgacac                 107
```

<210> SEQ ID NO 128
<211> LENGTH: 106
<212> TYPE: DNA
<213> ORGANISM: Homo Sapiens

<400> SEQUENCE: 128

```
gccaatgacc aaaacaatgt taccatcatg gctaacctga aggttaaaga tgcaactcag    60
atcactcagg ggccccgcag cacaatcgag aagaaaggtt ccaggg                  106
```

<210> SEQ ID NO 129
<211> LENGTH: 109
<212> TYPE: DNA
<213> ORGANISM: Homo Sapiens

<400> SEQUENCE: 129

```
accaggacca tcattcagaa ggaacccatt gacctccggg tcaaggccac caacagcatg    60
```

```
attgacagga agccgcgcct gctcttcccc accaactcca gcagccacc      109
```

<210> SEQ ID NO 130
<211> LENGTH: 90
<212> TYPE: DNA
<213> ORGANISM: Homo Sapiens

<400> SEQUENCE: 130

```
ggcaacctct actttgccaa tgtgctcacc tccgacaacc actcagacta catctgccac      60
gcccacttcc caggcaccag gaccatcatt                                       90
```

<210> SEQ ID NO 131
<211> LENGTH: 42
<212> TYPE: DNA
<213> ORGANISM: Homo Sapiens

<400> SEQUENCE: 131

```
ccaaggaaga gctgggtgtg accgtgtacc agtcgcccca ct                         42
```

<210> SEQ ID NO 132
<211> LENGTH: 61
<212> TYPE: DNA
<213> ORGANISM: Homo Sapiens

<400> SEQUENCE: 132

```
ggccttcgga gcgcctgtgc ccagtgttca gtggctggac gaggatggga caacagtgct      60
t                                                                      61
```

<210> SEQ ID NO 133
<211> LENGTH: 51
<212> TYPE: DNA
<213> ORGANISM: Homo Sapiens

<400> SEQUENCE: 133

```
gacaggaagc cgcgcctgct cttccccacc aactccagca gccacctggt g               51
```

<210> SEQ ID NO 134
<211> LENGTH: 40
<212> TYPE: DNA
<213> ORGANISM: Homo Sapiens

<400> SEQUENCE: 134

```
aatatgaagg acaccatgtg atggagccac ctgtcatcac                            40
```

<210> SEQ ID NO 135
<211> LENGTH: 29
<212> TYPE: DNA
<213> ORGANISM: Homo Sapiens

<400> SEQUENCE: 135

```
cccctggatg aggggggcaa ggggcaact                                        29
```

<210> SEQ ID NO 136
<211> LENGTH: 27
<212> TYPE: DNA
<213> ORGANISM: Homo Sapiens

<400> SEQUENCE: 136

```
aatatgaagg acaccatgtg atggagc                                          27
```

<210> SEQ ID NO 137
<211> LENGTH: 111

```
<212> TYPE: DNA
<213> ORGANISM: Homo Sapiens

<400> SEQUENCE: 137
tacatcatca ccgagttcat ggctaagggt agtttgctgg atttcctcaa gagtgatgaa      60
ggtggcaagg tgctgctgcc caagctcatt gacttctcgg cccagattgc a              111

<210> SEQ ID NO 138
<211> LENGTH: 48
<212> TYPE: DNA
<213> ORGANISM: Homo Sapiens

<400> SEQUENCE: 138
ggctgtacgc tgtggtcacc aaggaggagc ccatctacat catcaccg                   48

<210> SEQ ID NO 139
<211> LENGTH: 52
<212> TYPE: DNA
<213> ORGANISM: Homo Sapiens

<400> SEQUENCE: 139
caagaatctg gtgagcgaag ccatcgcagc tggcatcttc aacgacctgg gc              52

<210> SEQ ID NO 140
<211> LENGTH: 41
<212> TYPE: DNA
<213> ORGANISM: Homo Sapiens

<400> SEQUENCE: 140
tcatcgtctt tgagttcgcc gaccttggct ttctgggtga g                          41

<210> SEQ ID NO 141
<211> LENGTH: 97
<212> TYPE: DNA
<213> ORGANISM: Homo Sapiens

<400> SEQUENCE: 141
ccgctccgga gccatgtagg agcgcgtgcc cacgaaggag ttggccatgg agtctatgag      60
ctggccgctc accccgaagt cacacagctt gatctcc                               97

<210> SEQ ID NO 142
<211> LENGTH: 61
<212> TYPE: DNA
<213> ORGANISM: Homo Sapiens

<400> SEQUENCE: 142
cctcgtgccg aattcttggc ctcgagggcc aaattcccta tagtgagtcg tattaaattc      60
g                                                                      61

<210> SEQ ID NO 143
<211> LENGTH: 40
<212> TYPE: DNA
<213> ORGANISM: Homo Sapiens

<400> SEQUENCE: 143
tttaatacga ctcactatag ggaatttggc cctcgaggcc                            40

<210> SEQ ID NO 144
<211> LENGTH: 188
<212> TYPE: DNA
<213> ORGANISM: Homo Sapiens
```

```
<400> SEQUENCE: 144
cactccaaag acggcagact cacaggagac caaggaatcc cagaaagtgg agttgagtga      60
atccaggttg aaggcattca agtggccct cttggatgtg ttccgggaag ctcatgcgca     120
gtcaatcggc atgaatcgcc tcacagaatc catcaaccgg acagcgaag agcccttctc     180 ttcagttg                                                             188

<210> SEQ ID NO 145
<211> LENGTH: 79
<212> TYPE: DNA
<213> ORGANISM: Homo Sapiens

<400> SEQUENCE: 145
tgcccttggg tagtgctgtg gatatcctgg ccacagatga tcccaacttt agccaggaag      60
atcagcagga cacccagat                                                  79

<210> SEQ ID NO 146
<211> LENGTH: 77
<212> TYPE: DNA
<213> ORGANISM: Homo Sapiens

<400> SEQUENCE: 146
accaagaaga aaaggagaa gatggtgagt gcagcattca tgaagaagta catccatgtg      60
gccaaaatca tcaagcc                                                   77

<210> SEQ ID NO 147
<211> LENGTH: 79
<212> TYPE: DNA
<213> ORGANISM: Homo Sapiens

<400> SEQUENCE: 147
tgcccttggg tagtgctgtg gatatcctgg ccacagatga tcccaacttt agccaggaag      60
atcagcagga cacccagat                                                  79

<210> SEQ ID NO 148
<211> LENGTH: 41
<212> TYPE: DNA
<213> ORGANISM: Homo Sapiens

<400> SEQUENCE: 148
tgagcaagat gcaggatgac aatcaggtca tggtgtctga g                         41

<210> SEQ ID NO 149
<211> LENGTH: 97
<212> TYPE: DNA
<213> ORGANISM: Homo Sapiens

<400> SEQUENCE: 149
acccaagttc ggagacgagg cctcctcaga tgaggaagat gatgccctca gacaccatga      60
cctgattgtc atcctgcatc ttgctcagag caacctg                              97

<210> SEQ ID NO 150
<211> LENGTH: 80
<212> TYPE: DNA
<213> ORGANISM: Homo Sapiens

<400> SEQUENCE: 150
agcagtggct catccgccct acttcccatc ccacacaaac ccaattgtaa ataacatatg      60
acttcgtgag tacttttggg                                                 80
```

<210> SEQ ID NO 151
<211> LENGTH: 68
<212> TYPE: DNA
<213> ORGANISM: Homo Sapiens

<400> SEQUENCE: 151
gccctgctcc tgtgaacggg atcaatggct acaatgaaga cataaatcaa gagtctgctc    60
ccaaagcc                                                            68

<210> SEQ ID NO 152
<211> LENGTH: 46
<212> TYPE: DNA
<213> ORGANISM: Homo Sapiens

<400> SEQUENCE: 152
tggagtgcat tctgacggaa aaagaagaaa gagatccaca agggaa                  46

<210> SEQ ID NO 153
<211> LENGTH: 90
<212> TYPE: DNA
<213> ORGANISM: Homo Sapiens

<400> SEQUENCE: 153
gcacagtgaa ttttctttcc gtcactgtcc aacaaagtcc catgatagac acagccaaaa    60
tgccctcttc ctatgacttc attgaaatgc                                    90

<210> SEQ ID NO 154
<211> LENGTH: 196
<212> TYPE: DNA
<213> ORGANISM: Homo Sapiens

<400> SEQUENCE: 154
tatagcgtcc acaacaaaac gggtgcgaaa ctaccggtga agtggatggc tttagagagt    60
ctgcagacgc aaaagttcac caccaagtca gacgtgtggt ccttcggtgt gcttctctgg   120
gagctcatga cgagaggagc ccctccttat cctgacgtga acacatttga tatcactata   180
tacctgttgc aaggca                                                  196

<210> SEQ ID NO 155
<211> LENGTH: 73
<212> TYPE: DNA
<213> ORGANISM: Homo Sapiens

<400> SEQUENCE: 155
gtcaagatgt gtgacttcac cgaagaccag accgcagagt tcaaggaggc cttccagctg    60
tttgaccgaa cag                                                      73

<210> SEQ ID NO 156
<211> LENGTH: 82
<212> TYPE: DNA
<213> ORGANISM: Homo Sapiens

<400> SEQUENCE: 156
ccgaagacca gaccgcagag ttcaaggagg ccttccagct gtttgaccga acaggtgatg    60
gcaagatcct gtacagccag tg                                            82

<210> SEQ ID NO 157
<211> LENGTH: 46
<212> TYPE: DNA

<213> ORGANISM: Homo Sapiens

<400> SEQUENCE: 157
ggccaccgga gcggcccggc gacgatcgct gacagcttcc cctgcc  46

<210> SEQ ID NO 158
<211> LENGTH: 86
<212> TYPE: DNA
<213> ORGANISM: Homo Sapiens

<400> SEQUENCE: 158
ggcacccctt ctgcactgac ttccagatat ggttctccct tcctccctga ggacaccaaa  60
ttggatgaga gcaagtttga gagaag  86

<210> SEQ ID NO 159
<211> LENGTH: 88
<212> TYPE: DNA
<213> ORGANISM: Homo Sapiens

<400> SEQUENCE: 159
gcaaacctca tatgtcgacc agtgttccag agaaccccaa gagttcagca tccactgctg  60
tgtctgctgc ccccacagag aaggagtt  88

<210> SEQ ID NO 160
<211> LENGTH: 59
<212> TYPE: DNA
<213> ORGANISM: Homo Sapiens

<400> SEQUENCE: 160
ggagctgacc tcacaggctg agcgtgcgga ggagctgggc caagaattga aggcgtggc  59

<210> SEQ ID NO 161
<211> LENGTH: 72
<212> TYPE: DNA
<213> ORGANISM: Homo Sapiens

<400> SEQUENCE: 161
caatctgaag agatacctga agtctgaacc tatcccagag agcaatgatg ggcctgtgaa  60
ggtagtggta gc  72

<210> SEQ ID NO 162
<211> LENGTH: 66
<212> TYPE: DNA
<213> ORGANISM: Homo Sapiens

<400> SEQUENCE: 162
ttagcagttc tgatagcaac aacaggaatc tctccagcag tgctctccaa gtgagtgagc  60
ggccgc  66

<210> SEQ ID NO 163
<211> LENGTH: 55
<212> TYPE: DNA
<213> ORGANISM: Homo Sapiens

<400> SEQUENCE: 163
tgctccagaa aaacctgtaa agagacaaaa gacaggtgag acttcgagag ccctg  55

<210> SEQ ID NO 164
<211> LENGTH: 97
<212> TYPE: DNA
<213> ORGANISM: Homo Sapiens

```
<400> SEQUENCE: 164
ccgctacagg caggcgggaa ggaggaaagt ctagctggtt tcggcttcag gagcctcaga     60
gcgagcgggc gaacgtcgcg acgacgggct gagacct                             97

<210> SEQ ID NO 165
<211> LENGTH: 128
<212> TYPE: DNA
<213> ORGANISM: Homo Sapiens

<400> SEQUENCE: 165
gcggcatcaa ccagaagctt ttggctgagg ccttgaacca agtcacccag agagcctccc    60
ggagatcaga ctcagcctcc tcagagcctg ttgggatata tcagggtttc gagaagaaga   120
ccggagtt                                                            128

<210> SEQ ID NO 166
<211> LENGTH: 109
<212> TYPE: DNA
<213> ORGANISM: Homo Sapiens

<400> SEQUENCE: 166
gatcatcggc agatgcactg gcaccgcggc caacagccgg gacactatat tccagaaaga    60
acgcttcaac atcgacatgc cgcaccgctt caaggttcac aactacatg              109

<210> SEQ ID NO 167
<211> LENGTH: 66
<212> TYPE: DNA
<213> ORGANISM: Homo Sapiens

<400> SEQUENCE: 167
cacccagaga ctacagtaac tttgaccagg agttcctgaa cgagaaggcg cgcctctcct    60
acagcg                                                               66

<210> SEQ ID NO 168
<211> LENGTH: 92
<212> TYPE: DNA
<213> ORGANISM: Homo Sapiens

<400> SEQUENCE: 168
tgggccagac cagcaccaag cagaagacca acaaacccac gtacaacgag gagttttgcg    60
ctaacgtcac cgacggcggc cacctcgagt tg                                  92

<210> SEQ ID NO 169
<211> LENGTH: 107
<212> TYPE: DNA
<213> ORGANISM: Homo Sapiens

<400> SEQUENCE: 169
tgcgctaacg tcaccgacgg cggccacctc gagttggccg tcttccacga dacccccctg    60
ggctacgacc acttcgtggc caactgcacc ctgcagttcc aggagct                 107

<210> SEQ ID NO 170
<211> LENGTH: 75
<212> TYPE: DNA
<213> ORGANISM: Homo Sapiens

<400> SEQUENCE: 170
aacgaggagt tttgcgctaa cgtcaccgac ggcggccacc tcgagttggc cgtcttccac    60
```

```
gagaccccc tgggc                                              75

<210> SEQ ID NO 171
<211> LENGTH: 29
<212> TYPE: DNA
<213> ORGANISM: Homo Sapiens

<400> SEQUENCE: 171
cccacgtaca acgaggagtt ttgcgctaa                              29

<210> SEQ ID NO 172
<211> LENGTH: 60
<212> TYPE: DNA
<213> ORGANISM: Homo Sapiens

<400> SEQUENCE: 172
acggccacct cttccaagcc aagcgcttta acaggagagc gtactgcggt cagtgcagcg   60

<210> SEQ ID NO 173
<211> LENGTH: 121
<212> TYPE: DNA
<213> ORGANISM: Homo Sapiens

<400> SEQUENCE: 173
ccgctcaccc tcaagtgggt ggacagcgaa ggtgacccctt gcacggtgtc ctcccagatg   60
gagctggaag aggctttccg cctggcccgt cagtgcaggg atgaaggcct catcattcat  120
g                                                                 121

<210> SEQ ID NO 174
<211> LENGTH: 158
<212> TYPE: DNA
<213> ORGANISM: Homo Sapiens

<400> SEQUENCE: 174
gacgtactca atgaccagga acaaccgact tgtcgtctgg aagcaggagt gtaatccgac   60
caggaagggg ttgctggatg cctgctcaaa cacgtgcttc tctgtctgta cccagtcaat  120
atcctcgcca tcatgcacca gctctttctt caccactt                         158

<210> SEQ ID NO 175
<211> LENGTH: 75
<212> TYPE: DNA
<213> ORGANISM: Homo Sapiens

<400> SEQUENCE: 175
acggaattgc tgtctgattt ctgctttaac agcatttgat gccctgggat agcaaacgct   60
gaacaaacca catgc                                                   75

<210> SEQ ID NO 176
<211> LENGTH: 89
<212> TYPE: DNA
<213> ORGANISM: Homo Sapiens

<400> SEQUENCE: 176
aggacccatg gctttctgga gctctgaaaa tctgtcagcc accatatagc gaacgcgcca   60
agatttatct tctgctgctt gtcgaagtg                                    89

<210> SEQ ID NO 177
<211> LENGTH: 95
<212> TYPE: DNA
<213> ORGANISM: Homo Sapiens
```

<400> SEQUENCE: 177
gtcacacagt ttaacaaggt ggcaggggca gtggttagtt ctgtcctggg ggctacttcc        60
actggagagg gacctgggga ggtgaccata cggcc        95

<210> SEQ ID NO 178
<211> LENGTH: 31
<212> TYPE: DNA
<213> ORGANISM: Homo Sapiens

<400> SEQUENCE: 178
aacaccaggc agctgttccg actggcctcc t        31

<210> SEQ ID NO 179
<211> LENGTH: 39
<212> TYPE: DNA
<213> ORGANISM: Homo Sapiens

<400> SEQUENCE: 179
gggcggaggt ggaggtgcag ggtcaactgt ggctctgta        39

<210> SEQ ID NO 180
<211> LENGTH: 69
<212> TYPE: DNA
<213> ORGANISM: Homo Sapiens
<220> FEATURE:
<221> NAME/KEY: misc_feature
<222> LOCATION: (10)..(10)
<223> OTHER INFORMATION: n stands for a, c, t, or g

<400> SEQUENCE: 180
gcctgctcan agaagctggc aggactggga ggcgacagat gggcccctct tggcctctgt        60
cccagctct        69

<210> SEQ ID NO 181
<211> LENGTH: 67
<212> TYPE: DNA
<213> ORGANISM: Homo Sapiens

<400> SEQUENCE: 181
ggatggtgac ctgtgagaat gaagctggag cccagcgtca gaagtctagt tttataggca        60
gctgtcc        67

<210> SEQ ID NO 182
<211> LENGTH: 181
<212> TYPE: DNA
<213> ORGANISM: Homo Sapiens

<400> SEQUENCE: 182
tgaatcttga aaacccctca tgtaattcag tgttagaccc aagagacttg agacagctcc        60
atcagatgtc ctcttccagt atgtcagcag gcgccaattc caatactact gcccattgtt        120
tcacaatcag atgcatttga gggatctgac ttcagttgtg cagataacag catgataaat        180
g        181

<210> SEQ ID NO 183
<211> LENGTH: 143
<212> TYPE: DNA
<213> ORGANISM: Homo Sapiens

<400> SEQUENCE: 183

-continued

```
aggagcagag ccaggcgccc atcacaccgc agcagggcca ggcactcgcg aaacagatcc      60
acgctgtgcg ctacctcgaa tgctcagccc tgcaacagga tggtgtcaag gaagtgttcg     120
ccgaggctgt ccgggctgtg ctc                                             143
```

<210> SEQ ID NO 184
<211> LENGTH: 135
<212> TYPE: DNA
<213> ORGANISM: Homo Sapiens

<400> SEQUENCE: 184

```
ccattgccag tccgccgtcc tatgagaacg tgcggcacaa gtggcatcca gaggtgtgcc      60
accactgccc tgatgtgccc atcctgctgg tgggcaccaa gaaggacctg agagcccagc     120
ctgacaccct acggc                                                      135
```

<210> SEQ ID NO 185
<211> LENGTH: 46
<212> TYPE: DNA
<213> ORGANISM: Homo Sapiens

<400> SEQUENCE: 185

```
aggagcagag ccaggcgccc atcacaccgc agcagggcca ggcact                     46
```

<210> SEQ ID NO 186
<211> LENGTH: 112
<212> TYPE: DNA
<213> ORGANISM: Homo Sapiens

<400> SEQUENCE: 186

```
ggcaatggag aaacagatga cgaaaacgtt ggtctgaggg taggagagtg tacggaggcg      60
gtcatactcc tcctggcccg cagtgtccca caggttcagg ttcactttgc gc             112
```

<210> SEQ ID NO 187
<211> LENGTH: 107
<212> TYPE: DNA
<213> ORGANISM: Homo Sapiens

<400> SEQUENCE: 187

```
caccatcctg ttgcagggct gagcattcga ggtagcgcac agcgtggatc tgcttggcca      60
gtgcctggcc ctgctgcggt gtgatgggcg cctggccctg ctccttg                   107
```

<210> SEQ ID NO 188
<211> LENGTH: 119
<212> TYPE: DNA
<213> ORGANISM: Homo Sapiens

<400> SEQUENCE: 188

```
gagcacagcc cggacagcct cggcgagcta ttccttggct ccatcgtgtt gcagggtgg       60 cgtcctaggt agcgcgcagc gtggatatgc tcggccagtg catggccctg atgcggtgt      119
```

<210> SEQ ID NO 189
<211> LENGTH: 123
<212> TYPE: DNA
<213> ORGANISM: Homo Sapiens

<400> SEQUENCE: 189

```
tggagaagca aaacctagt tacataattt acttcatggt ctgcagttag ggtcagtgac       60
ttacgacata attcctgctt gatgataatg aaattgacag aagcctgaag gctgagtgag     120
tga                                                                   123
```

<210> SEQ ID NO 190
<211> LENGTH: 27
<212> TYPE: DNA
<213> ORGANISM: Homo Sapiens

<400> SEQUENCE: 190
agccgcagtc ttggaccata atcatgg                                27

<210> SEQ ID NO 191
<211> LENGTH: 91
<212> TYPE: DNA
<213> ORGANISM: Homo Sapiens

<400> SEQUENCE: 191
ggccaaggtg caacttcctt cggtcgtccc gaatccgggt tcatccgaca ccagccgcct    60
ccaccatgcc gccgaagttc gaccccaacg a                           91

<210> SEQ ID NO 192
<211> LENGTH: 53
<212> TYPE: DNA
<213> ORGANISM: Homo Sapiens

<400> SEQUENCE: 192
tggcgagaag aaaaagggcc gttctgccat caacgaagtg gtaacccgag aat            53

<210> SEQ ID NO 193
<211> LENGTH: 37
<212> TYPE: DNA
<213> ORGANISM: Homo Sapiens

<400> SEQUENCE: 193
ggccgttctg ccatcaacga agtggtaacc cgagaat                     37

<210> SEQ ID NO 194
<211> LENGTH: 42
<212> TYPE: DNA
<213> ORGANISM: Homo Sapiens

<400> SEQUENCE: 194
ggcggcttgt gcagcaatgg ccaagatcaa ggctcgagat ct               42

<210> SEQ ID NO 195
<211> LENGTH: 33
<212> TYPE: DNA
<213> ORGANISM: Homo Sapiens

<400> SEQUENCE: 195
ggcggcttgt gcagcaatgg ccaagatcaa ggc                         33

<210> SEQ ID NO 196
<211> LENGTH: 71
<212> TYPE: DNA
<213> ORGANISM: Homo Sapiens

<400> SEQUENCE: 196
gccagcacca acattggcct ttgcagtccc cctgactttc ttcattctgt tcttgcgttc    60
ctttcgttgc t                                                 71

<210> SEQ ID NO 197
<211> LENGTH: 55
<212> TYPE: DNA

```
<213> ORGANISM: Homo Sapiens

<400> SEQUENCE: 197 cttttttgcca gcaccaacat tggcctttgc agtcccctg actttcttca ttctg        55

<210> SEQ ID NO 198
<211> LENGTH: 56
<212> TYPE: DNA
<213> ORGANISM: Homo Sapiens

<400> SEQUENCE: 198
ttacctcgtt gcactgctga gagcaagatg ggtcaccagc agctgtactg gagcca       56

<210> SEQ ID NO 199
<211> LENGTH: 47
<212> TYPE: DNA
<213> ORGANISM: Homo Sapiens

<400> SEQUENCE: 199
ggcagcaaaa caagtgacat gaagggaggg tccctgtgtg tgtgtgc                 47

<210> SEQ ID NO 200
<211> LENGTH: 120
<212> TYPE: DNA
<213> ORGANISM: Homo Sapiens

<400> SEQUENCE: 200
gagagccagg agcatcctga agctgaccca ggtagcgctg ccccatacct gaagaccaag   60
tttatctgtg tgacaccaac gacctgcagc ataccattg acctgccgat gtccccccgc   120

<210> SEQ ID NO 201
<211> LENGTH: 108
<212> TYPE: DNA
<213> ORGANISM: Homo Sapiens

<400> SEQUENCE: 201
aagacccaga tccagtccgt ggaaccatac acaaagcagc agctgaacaa catgtcattt   60
gctgaaatca tcatgggcta taagatcatg gatgctacca atatcctg              108

<210> SEQ ID NO 202
<211> LENGTH: 98
<212> TYPE: DNA
<213> ORGANISM: Homo Sapiens

<400> SEQUENCE: 202
ggatgtccgg aagagagtgc aggatctaga acagaaaatg aaagtggtag agaatctcca   60
ggatgacttt gatttcaact ataaaaccct caagagtc                          98

<210> SEQ ID NO 203
<211> LENGTH: 115
<212> TYPE: DNA
<213> ORGANISM: Homo Sapiens

<400> SEQUENCE: 203
ttcctgcaag agtcgaatgt tctctatcag cacaatctac gaagaatcaa gcagtttctt   60
cagagcaggt atcttgagaa gccaatggag attgcccgga ttgtggcccg gtgcc       115

<210> SEQ ID NO 204
<211> LENGTH: 85
<212> TYPE: DNA
<213> ORGANISM: Homo Sapiens
```

```
<400> SEQUENCE: 204
agatgctcac tgcgctggac cagatgcgga gaagcatcgt gagtgagctg gcggggcttt      60
tgtcagcgat ggagtacgtg cagaa                                            85

<210> SEQ ID NO 205
<211> LENGTH: 47
<212> TYPE: DNA
<213> ORGANISM: Homo Sapiens

<400> SEQUENCE: 205
gaccagcagt atagccgctt cctgcaagag tcgaatgttc tctatca                    47

<210> SEQ ID NO 206
<211> LENGTH: 47
<212> TYPE: DNA
<213> ORGANISM: Homo Sapiens

<400> SEQUENCE: 206
gagctggctg actggaagag gcggcaacag atggagtacg tgcagaa                    47

<210> SEQ ID NO 207
<211> LENGTH: 105
<212> TYPE: DNA
<213> ORGANISM: Homo Sapiens

<400> SEQUENCE: 207
tcttgataat ccacaggaga acattaaggc cacccagctc ctggagggcc tggtgcagga      60
gctgcagaag aaggcagaac accaggtggg ggaagatggg ttttt                     105

<210> SEQ ID NO 208
<211> LENGTH: 82
<212> TYPE: DNA
<213> ORGANISM: Homo Sapiens

<400> SEQUENCE: 208
gagaacatta aggccaccca gctcctggag ggcctggcgc aggagctgca gaacaaggca      60
caacaccagg aggggaaga tg                                                82

<210> SEQ ID NO 209
<211> LENGTH: 107
<212> TYPE: DNA
<213> ORGANISM: Homo Sapiens

<400> SEQUENCE: 209
aacaagcagc aggcccacga cctgctcatc aacaagccag atgggacctt cctgctgcgc      60
ttcagcgact cggaaatcgg gggcatcacc attgcttgga agtttga                   107

<210> SEQ ID NO 210
<211> LENGTH: 104
<212> TYPE: DNA
<213> ORGANISM: Homo Sapiens

<400> SEQUENCE: 210
aaacgaatca agaggtctga ccgccgtggt gcagagtcgg tcacggaaga gaagttcaca      60
atcttgtttg actcacagtt cagtgttggt ggaaatgagc tggt                      104

<210> SEQ ID NO 211
<211> LENGTH: 104
<212> TYPE: DNA
```

<210> SEQ ID NO 211
<211> LENGTH: 104
<212> TYPE: DNA
<213> ORGANISM: Homo Sapiens

<400> SEQUENCE: 211
tcttgataat cctcaggagg ccattaagcc cacccagctc atgaagggca tggtgcagta    60
gctgcagaag aagagcagaa ctccaggtgg gggaagatgg gttt    104

<210> SEQ ID NO 212
<211> LENGTH: 48
<212> TYPE: DNA
<213> ORGANISM: Homo Sapiens

<400> SEQUENCE: 212
tcttgataat ccacaggaga acattaaggc cacccagctc ctggaggg    48

<210> SEQ ID NO 213
<211> LENGTH: 47
<212> TYPE: DNA
<213> ORGANISM: Homo Sapiens

<400> SEQUENCE: 213
acaatcctgt ttgaatccca gttcagtgtt ggtggaaatg agctggt    47

<210> SEQ ID NO 214
<211> LENGTH: 30
<212> TYPE: DNA
<213> ORGANISM: Homo Sapiens

<400> SEQUENCE: 214
ccagttcagt gttggtggaa atgagctggt    30

<210> SEQ ID NO 215
<211> LENGTH: 63
<212> TYPE: DNA
<213> ORGANISM: Homo Sapiens

<400> SEQUENCE: 215
cgagctgcgc ctctcggcaa gatttcgcgc tgaccatccc gggccctttc atcactaatc    60
ggt    63

<210> SEQ ID NO 216
<211> LENGTH: 49
<212> TYPE: DNA
<213> ORGANISM: Homo Sapiens

<400> SEQUENCE: 216
ggtcgtagca gaagcaggag caaggcgtcc aggggaaact ggagggctt    49

<210> SEQ ID NO 217
<211> LENGTH: 123
<212> TYPE: DNA
<213> ORGANISM: Homo Sapiens

<400> SEQUENCE: 217
ccagcatggc aagtggtga cctggaggac ggccacattg tgccccaga gctgcgagga    60 gaggaatctc cgggagaacg ggtatgagtg tgagtggcgc tataacagct gtgcacctgc    120
ctg    123

<210> SEQ ID NO 218
<211> LENGTH: 127
<212> TYPE: DNA
<213> ORGANISM: Homo Sapiens

```
<400> SEQUENCE: 218
ccttgcccct gaagcccctc ctcctactct gcccccccac atggcacaag tcactgtggg      60
cccggggctc ttgggggttt cgaccctggg gcccaagagg aactccatgg ttctggatgt     120
ggcgttc                                                               127

<210> SEQ ID NO 219
<211> LENGTH: 84
<212> TYPE: DNA
<213> ORGANISM: Homo Sapiens

<400> SEQUENCE: 219
gcccggacct gtgcccagga gggaatggtg ctgtacggct ggaccgacca cagcgcgtgc      60
agcccagtgt gccctgctgg tatg                                             84

<210> SEQ ID NO 220
<211> LENGTH: 76
<212> TYPE: DNA
<213> ORGANISM: Homo Sapiens

<400> SEQUENCE: 220
agtgctgtgg aaggtgcctg ccatctgcct gtgaggtggt gactggctca ccgcgggggg      60
actcccagtc ttcctg                                                      76

<210> SEQ ID NO 221
<211> LENGTH: 63
<212> TYPE: DNA
<213> ORGANISM: Homo Sapiens

<400> SEQUENCE: 221
tggtcagcca gggtgaccgg gagcaggcgc ccaacctggt ctacatggtc accggaaatc      60
ctg                                                                    63

<210> SEQ ID NO 222
<211> LENGTH: 65
<212> TYPE: DNA
<213> ORGANISM: Homo Sapiens

<400> SEQUENCE: 222
agtgccacac cgtgacttgc cagccagatg ccagaccttg ctgaagagt catcgggtca       60 actgt                                                                  65

<210> SEQ ID NO 223
<211> LENGTH: 81
<212> TYPE: DNA
<213> ORGANISM: Homo Sapiens

<400> SEQUENCE: 223
acatggcaca agtcactgtg ggcccggggc tcttgggggt ttcgaccctg ggcccaaga       60 ggaactccat ggttctggat g                                                81

<210> SEQ ID NO 224
<211> LENGTH: 65
<212> TYPE: DNA
<213> ORGANISM: Homo Sapiens

<400> SEQUENCE: 224
tccaccagcg aggtcttgaa atacacactg ttccaaatct tcagcaagat cgaccgccct      60
```

-continued gaagc 65

<210> SEQ ID NO 225
<211> LENGTH: 57
<212> TYPE: DNA
<213> ORGANISM: Homo Sapiens

<400> SEQUENCE: 225
ctggctcacc gcgggggggac tcccagtctt cctggaagag tgtcggctcc cagtggg    57

<210> SEQ ID NO 226
<211> LENGTH: 57
<212> TYPE: DNA
<213> ORGANISM: Homo Sapiens

<400> SEQUENCE: 226
accctcccgg cacctccctc tctcgagact gcaacacctg catttgccga aacagcc    57

<210> SEQ ID NO 227
<211> LENGTH: 25
<212> TYPE: DNA
<213> ORGANISM: Homo Sapiens

<400> SEQUENCE: 227
agctgcatgg gtgcctgctg ctgcc    25

<210> SEQ ID NO 228
<211> LENGTH: 135
<212> TYPE: DNA
<213> ORGANISM: Homo Sapiens

<400> SEQUENCE: 228
ctcagtggcc ttcaccagca ccgagcctgc ccacatcgtg gcctccttcc gctctggcga    60
caccgtcttg tatgacatgg aggttggcag tgccctcctc acgctggagt cccggggcag    120
cagcggtcca accca    135

<210> SEQ ID NO 229
<211> LENGTH: 28
<212> TYPE: PRT
<213> ORGANISM: Homo sapiens

<400> SEQUENCE: 229

Leu Trp His Gly Ser Arg Thr Thr Asn Phe Ala Gly Ile Leu Ser Gln
1               5                   10                  15

Gly Leu Arg Ile Ala Pro Pro Glu Ala Pro Val Thr
            20                  25

<210> SEQ ID NO 230
<211> LENGTH: 16
<212> TYPE: PRT
<213> ORGANISM: Homo sapiens

<400> SEQUENCE: 230

Met Ala Val Thr Ala Leu Ala Ala Arg Thr Trp Leu Gly Val Trp Gly
1               5                   10                  15

<210> SEQ ID NO 231
<211> LENGTH: 28
<212> TYPE: PRT
<213> ORGANISM: Homo sapiens

<400> SEQUENCE: 231

-continued

Arg Asp Glu Glu Ser Thr Arg Ser Glu Glu Val Thr Arg Glu Glu Met
1               5                   10                  15

Ala Ala Ala Gly Leu Thr Val Thr Val Thr His Ser
                20                  25

<210> SEQ ID NO 232
<211> LENGTH: 19
<212> TYPE: PRT
<213> ORGANISM: Homo sapiens

<400> SEQUENCE: 232

Glu Val Thr Arg Glu Glu Met Ala Ala Ala Gly Leu Thr Val Thr Val
1               5                   10                  15

Thr His Ser

<210> SEQ ID NO 233
<211> LENGTH: 22
<212> TYPE: PRT
<213> ORGANISM: Homo sapiens

<400> SEQUENCE: 233

Tyr Ala Lys Ser Gln Pro Asp Met Ala Ile Met Ala Val Asn Thr Phe
1               5                   10                  15

Val Lys Asp Cys Glu Asp
                20

<210> SEQ ID NO 234
<211> LENGTH: 16
<212> TYPE: PRT
<213> ORGANISM: Homo sapiens

<400> SEQUENCE: 234

Pro Asp Met Ala Ile Met Ala Val Asn Thr Phe Val Lys Asp Cys Glu
1               5                   10                  15

<210> SEQ ID NO 235
<211> LENGTH: 14
<212> TYPE: PRT
<213> ORGANISM: Homo sapiens

<400> SEQUENCE: 235

Ala Pro Ala Thr Ser Glu Gly Gln Ser Lys Arg Cys Lys Pro
1               5                   10

<210> SEQ ID NO 236
<211> LENGTH: 16
<212> TYPE: PRT
<213> ORGANISM: Homo sapiens

<400> SEQUENCE: 236

Glu Ile Ser Leu Leu Lys Glu Leu Asn His Pro Asn Ile Val Lys Leu
1               5                   10                  15

<210> SEQ ID NO 237
<211> LENGTH: 19
<212> TYPE: PRT
<213> ORGANISM: Homo sapiens

<400> SEQUENCE: 237

Tyr Thr His Glu Val Val Thr Leu Trp Tyr Arg Ala Pro Glu Ile Leu
1               5                   10                  15

Leu Gly Cys

<210> SEQ ID NO 238
<211> LENGTH: 17
<212> TYPE: PRT
<213> ORGANISM: Homo sapiens

<400> SEQUENCE: 238

Pro Glu Leu Val His Tyr Arg Glu Glu Lys His Val Phe Pro Gln Arg
1               5                   10                  15

Phe

<210> SEQ ID NO 239
<211> LENGTH: 11
<212> TYPE: PRT
<213> ORGANISM: Homo sapiens

<400> SEQUENCE: 239

Lys Met Ala Ala Lys Cys Arg Asn Arg Arg
1               5                   10

<210> SEQ ID NO 240
<211> LENGTH: 23
<212> TYPE: PRT
<213> ORGANISM: Homo sapiens

<400> SEQUENCE: 240

Val Gln Ala Gln Pro Gln Ile Ala Thr Leu Ala Gln Val Ser Met Pro
1               5                   10                  15

Ala Ala His Ala Thr Ser Ser
            20

<210> SEQ ID NO 241
<211> LENGTH: 36
<212> TYPE: PRT
<213> ORGANISM: Homo sapiens

<400> SEQUENCE: 241

Met Arg Lys Ile Val Ala Thr Trp Met Leu Glu Val Cys Glu Glu Gln
1               5                   10                  15

Lys Cys Glu Glu Glu Val Phe Pro Leu Ala Met Asn Tyr Leu Asp Arg
            20                  25                  30

Phe Leu Ser Leu
        35

<210> SEQ ID NO 242
<211> LENGTH: 16
<212> TYPE: PRT
<213> ORGANISM: Homo sapiens

<400> SEQUENCE: 242

Ala Lys Ser Lys Gln Ala Ile Leu Ala Ala Gln Arg Arg Gly Gly Asp
1               5                   10                  15

<210> SEQ ID NO 243
<211> LENGTH: 14
<212> TYPE: PRT
<213> ORGANISM: Homo sapiens

<400> SEQUENCE: 243

Arg Gly Gly Ala Asp Asp Glu Arg Ser Ser Trp Arg Asn Ala
1               5                   10

<210> SEQ ID NO 244

```
<211> LENGTH: 27
<212> TYPE: PRT
<213> ORGANISM: Homo sapiens

<400> SEQUENCE: 244

His Tyr Glu Asp His Ser Val Ala Asp Ala Ala Met Glu Gln Tyr Ile
1               5                   10                  15

Leu Tyr Leu Val Glu His Glu Glu Tyr Gln Leu
            20                  25

<210> SEQ ID NO 245
<211> LENGTH: 12
<212> TYPE: PRT
<213> ORGANISM: Homo sapiens

<400> SEQUENCE: 245

Pro Gln Leu Lys Ser Gly Glu Leu Ala Lys Arg Ser
1               5                   10

<210> SEQ ID NO 246
<211> LENGTH: 44
<212> TYPE: PRT
<213> ORGANISM: Homo sapiens

<400> SEQUENCE: 246

Val Thr Val Ser Ala Asp Ser Ser Ala Ser Met Asn Ser Gly Val Leu
1               5                   10                  15

Leu Val Arg Pro Ser Arg Leu Ser Ser Ser Gly Thr Pro Met Leu Ala
            20                  25                  30

Gly Val Ser Glu Tyr Glu Leu Pro Glu Asp Pro Arg
        35                  40

<210> SEQ ID NO 247
<211> LENGTH: 20
<212> TYPE: PRT
<213> ORGANISM: Homo sapiens

<400> SEQUENCE: 247

Gly Thr Lys Lys Ser Asp Phe His Ser Gln Met Ala Val His Lys Leu
1               5                   10                  15

Ala Lys Ser Ile
            20

<210> SEQ ID NO 248
<211> LENGTH: 19
<212> TYPE: PRT
<213> ORGANISM: Homo sapiens

<400> SEQUENCE: 248

Leu Thr Ser Gln Thr Met Gly Gly Gln Ala Glu Thr Leu Leu Thr Ser
1               5                   10                  15

Gln Lys Gly

<210> SEQ ID NO 249
<211> LENGTH: 16
<212> TYPE: PRT
<213> ORGANISM: Homo sapiens

<400> SEQUENCE: 249

Ile Lys Pro Ile Ser Ile Ala Gly Gly Phe Tyr Gly Glu Glu Pro Leu
1               5                   10                  15
```

<210> SEQ ID NO 250
<211> LENGTH: 20
<212> TYPE: PRT
<213> ORGANISM: Homo sapiens

<400> SEQUENCE: 250

Asp Gln Gln Glu Ala Ala Leu Val Asp Met Val Asn Asp Gly Val Glu
1               5                   10                  15

Asp Leu Arg Cys
            20

<210> SEQ ID NO 251
<211> LENGTH: 41
<212> TYPE: PRT
<213> ORGANISM: Homo sapiens

<400> SEQUENCE: 251

Cys Leu Asp Ala Phe Pro Leu Leu Ser Ala Tyr Val Gly Arg Leu Ser
1               5                   10                  15

Ala Arg Pro Lys Leu Lys Ala Phe Leu Ala Ser Pro Glu Tyr Val Asn
            20                  25                  30

Leu Pro Ile Asn Gly Asn Gly Lys Gln
        35                  40

<210> SEQ ID NO 252
<211> LENGTH: 39
<212> TYPE: PRT
<213> ORGANISM: Homo sapiens

<400> SEQUENCE: 252

Trp Met Asp Gly Arg Asp Glu Val Thr Gln Gln Lys Tyr Gln Arg Pro
1               5                   10                  15

Glu Thr Glu Trp Pro Arg Val Ser Leu His Pro Glu Pro Glu Asp Ala
            20                  25                  30

Ala Lys Thr Ser Leu Ser Glu
        35

<210> SEQ ID NO 253
<211> LENGTH: 25
<212> TYPE: PRT
<213> ORGANISM: Homo sapiens

<400> SEQUENCE: 253

Arg Ala Ala Pro Gly Asn Gln Pro Ser Gln Ala Pro Ala Pro Phe Leu
1               5                   10                  15

Lys Lys Leu Leu Gly Thr Leu Gln Leu
            20                  25

<210> SEQ ID NO 254
<211> LENGTH: 27
<212> TYPE: PRT
<213> ORGANISM: Homo sapiens

<400> SEQUENCE: 254

Ile Ser Asp Gln Asp Gln Glu Val Thr Leu Glu Glu Asp Leu Met Asp
1               5                   10                  15

Met Ala Val Asp Val Asp Leu Gly Met Ala Ile
            20                  25

<210> SEQ ID NO 255
<211> LENGTH: 53
<212> TYPE: PRT

-continued

<213> ORGANISM: Homo sapiens

<400> SEQUENCE: 255

Ala Gly Leu Glu Arg Met Arg Pro Gly Ala Tyr Ser Thr Gly Tyr Gly
1               5                   10                  15

Gly Tyr Glu Glu Tyr Ser Gly Leu Ser Asp Gly Tyr Gly Phe Thr Thr
            20                  25                  30

Asp Leu Phe Gly Arg Asp Leu Ser Tyr Cys Leu Ser Gly Met Tyr Asp
        35                  40                  45

His Arg Tyr Gly Asp
    50

<210> SEQ ID NO 256
<211> LENGTH: 16
<212> TYPE: PRT
<213> ORGANISM: Homo sapiens

<400> SEQUENCE: 256

Gly Val Gly Ala Gly Glu Asp Gly Gly Ser Arg Gly Arg Glu Leu His
1               5                   10                  15

<210> SEQ ID NO 257
<211> LENGTH: 17
<212> TYPE: PRT
<213> ORGANISM: Homo sapiens

<400> SEQUENCE: 257

Lys Asp Gln Val Ala Asn Ser Ala Phe Val Glu Arg Leu Arg Lys His
1               5                   10                  15

Gly

<210> SEQ ID NO 258
<211> LENGTH: 19
<212> TYPE: PRT
<213> ORGANISM: Homo sapiens

<400> SEQUENCE: 258

Met Ser Ser Phe Gly Tyr Arg Thr Leu Thr Val Ala Leu Phe Thr Leu
1               5                   10                  15

Ile Cys Cys

<210> SEQ ID NO 259
<211> LENGTH: 14
<212> TYPE: PRT
<213> ORGANISM: Homo sapiens

<400> SEQUENCE: 259

Tyr Glu Pro Val Ser Asp Ser Gln Met Val Ile Ile Val Thr
1               5                   10

<210> SEQ ID NO 260
<211> LENGTH: 13
<212> TYPE: PRT
<213> ORGANISM: Homo sapiens

<400> SEQUENCE: 260

Lys Leu Val Arg Lys Asp Arg Leu Val Leu Ser Tyr Val
1               5                   10

<210> SEQ ID NO 261
<211> LENGTH: 16
<212> TYPE: PRT

<213> ORGANISM: Homo sapiens

<400> SEQUENCE: 261

Lys Lys Arg Tyr Asp Leu Ser Ala Leu Val Arg His Ala Glu Pro Glu
1               5                   10                  15

<210> SEQ ID NO 262
<211> LENGTH: 45
<212> TYPE: PRT
<213> ORGANISM: Homo sapiens

<400> SEQUENCE: 262

Leu Leu Gly Leu Cys Ala Leu Leu Pro Arg Leu Ala Gly Leu Asn Ile
1               5                   10                  15

Cys Thr Ser Gly Ser Ala Thr Ser Cys Glu Glu Cys Leu Leu Ile His
                20                  25                  30

Pro Lys Cys Ala Trp Cys Ser Lys Glu Asp Phe Gly Ser
            35                  40                  45

<210> SEQ ID NO 263
<211> LENGTH: 37
<212> TYPE: PRT
<213> ORGANISM: Homo sapiens

<400> SEQUENCE: 263

Lys Asp Cys Val Met Met Phe Thr Tyr Val Glu Leu Pro Ser Gly Lys
1               5                   10                  15

Ser Asn Leu Thr Val Leu Arg Glu Pro Glu Cys Gly Asn Thr Pro Asn
                20                  25                  30

Ala Met Thr Ile Leu
            35

<210> SEQ ID NO 264
<211> LENGTH: 29
<212> TYPE: PRT
<213> ORGANISM: Homo sapiens

<400> SEQUENCE: 264

Gly His Gly Glu Cys His Cys Gly Glu Cys Lys Cys His Ala Gly Tyr
1               5                   10                  15

Ile Gly Asp Asn Cys Asn Cys Ser Thr Asp Ile Ser Thr
                20                  25

<210> SEQ ID NO 265
<211> LENGTH: 30
<212> TYPE: PRT
<213> ORGANISM: Homo sapiens

<400> SEQUENCE: 265

Val Glu Leu Pro Ser Gly Lys Ser Asn Leu Thr Val Leu Arg Glu Pro
1               5                   10                  15

Glu Cys Gly Asn Thr Pro Asn Ala Met Thr Ile Leu Leu Ala
                20                  25                  30

<210> SEQ ID NO 266
<211> LENGTH: 24
<212> TYPE: PRT
<213> ORGANISM: Homo sapiens

<400> SEQUENCE: 266

Pro Glu Ala Ala Val Arg Glu Thr Val Met Leu Leu Leu Cys Leu Gly
1               5                   10                  15

```
Val Pro Thr Gly Arg Pro Tyr Asn
            20

<210> SEQ ID NO 267
<211> LENGTH: 16
<212> TYPE: PRT
<213> ORGANISM: Homo sapiens

<400> SEQUENCE: 267

Gly Tyr Gly Arg Ala Pro Gly Gly Leu Ser Leu His Asp Tyr Lys Leu
1               5                   10                  15

<210> SEQ ID NO 268
<211> LENGTH: 9
<212> TYPE: PRT
<213> ORGANISM: Homo sapiens

<400> SEQUENCE: 268

Pro Gly Gly Leu Ser Leu His Asp Tyr
1               5

<210> SEQ ID NO 269
<211> LENGTH: 35
<212> TYPE: PRT
<213> ORGANISM: Homo sapiens

<400> SEQUENCE: 269

Ser Val Gln Trp Leu Asp Glu Asp Gly Thr Thr Val Leu Gln Asp Glu
1               5                   10                  15

Arg Phe Phe Pro Tyr Ala Asn Gly Thr Leu Gly Ile Arg Asp Leu Gln
            20                  25                  30

Ala Asn Asp
        35

<210> SEQ ID NO 270
<211> LENGTH: 36
<212> TYPE: PRT
<213> ORGANISM: Homo sapiens

<400> SEQUENCE: 270

Thr Arg Thr Ile Ile Gln Lys Glu Pro Ile Asp Leu Arg Val Lys Ala
1               5                   10                  15

Thr Asn Ser Met Ile Asp Arg Lys Pro Arg Leu Leu Phe Pro Thr Asn
            20                  25                  30

Ser Ser Ser His
        35

<210> SEQ ID NO 271
<211> LENGTH: 30
<212> TYPE: PRT
<213> ORGANISM: Homo sapiens

<400> SEQUENCE: 271

Gly Asn Leu Tyr Phe Ala Asn Val Leu Thr Ser Asp Asn His Ser Asp
1               5                   10                  15

Tyr Ile Cys His Ala His Phe Pro Gly Thr Arg Thr Ile Ile
            20                  25                  30

<210> SEQ ID NO 272
<211> LENGTH: 20
<212> TYPE: PRT
<213> ORGANISM: Homo sapiens
```

<400> SEQUENCE: 272

Ala Phe Gly Ala Pro Val Pro Ser Val Gln Trp Leu Asp Glu Asp Gly
1               5                   10                  15

Thr Thr Val Leu
            20

<210> SEQ ID NO 273
<211> LENGTH: 15
<212> TYPE: PRT
<213> ORGANISM: Homo sapiens

<400> SEQUENCE: 273

Glu Tyr Glu Gly His His Val Met Glu Pro Val Ile Thr Glu
1               5                   10                  15

<210> SEQ ID NO 274
<211> LENGTH: 13
<212> TYPE: PRT
<213> ORGANISM: Homo sapiens

<400> SEQUENCE: 274

Lys Glu Glu Leu Gly Val Thr Val Tyr Gln Ser Pro His
1               5                   10

<210> SEQ ID NO 275
<211> LENGTH: 17
<212> TYPE: PRT
<213> ORGANISM: Homo sapiens

<400> SEQUENCE: 275

Asp Arg Lys Pro Arg Leu Leu Phe Pro Thr Asn Ser Ser Ser His Leu
1               5                   10                  15

Val

<210> SEQ ID NO 276
<211> LENGTH: 19
<212> TYPE: PRT
<213> ORGANISM: Homo sapiens

<400> SEQUENCE: 276

Glu Ala Lys Asn Leu Val Ser Glu Ala Ile Ala Ala Gly Ile Phe Asn
1               5                   10                  15

Asp Leu Gly

<210> SEQ ID NO 277
<211> LENGTH: 25
<212> TYPE: PRT
<213> ORGANISM: Homo sapiens

<400> SEQUENCE: 277

Pro Leu Gly Ser Ala Val Asp Ile Leu Ala Thr Asp Asp Pro Asn Phe
1               5                   10                  15

Ser Gln Glu Asp Gln Gln Asp Thr Gln
            20                  25

<210> SEQ ID NO 278
<211> LENGTH: 14
<212> TYPE: PRT
<213> ORGANISM: Homo sapiens

<400> SEQUENCE: 278

-continued

Leu Ser Lys Met Gln Asp Asp Asn Gln Val Met Val Ser Glu
1               5                   10

<210> SEQ ID NO 279
<211> LENGTH: 22
<212> TYPE: PRT
<213> ORGANISM: Homo sapiens

<400> SEQUENCE: 279

Pro Ala Pro Val Asn Gly Ile Asn Gly Tyr Asn Glu Asp Ile Asn Gln
1               5                   10                  15

Glu Ser Ala Pro Lys Ala
            20

<210> SEQ ID NO 280
<211> LENGTH: 65
<212> TYPE: PRT
<213> ORGANISM: Homo sapiens

<400> SEQUENCE: 280

Tyr Ser Val His Asn Lys Thr Gly Ala Lys Leu Pro Val Lys Trp Met
1               5                   10                  15

Ala Leu Glu Ser Leu Gln Thr Gln Lys Phe Thr Thr Lys Ser Asp Val
            20                  25                  30

Trp Ser Phe Gly Val Val Leu Trp Glu Leu Met Thr Arg Gly Ala Pro
        35                  40                  45

Pro Tyr Pro Asp Val Asn Thr Phe Asp Ile Thr Val Tyr Leu Leu Gln
    50                  55                  60

Gly
65

<210> SEQ ID NO 281
<211> LENGTH: 22
<212> TYPE: PRT
<213> ORGANISM: Homo sapiens

<400> SEQUENCE: 281

Met Cys Asp Phe Thr Glu Asp Gln Thr Thr Glu Phe Lys Glu Ala Phe
1               5                   10                  15

Gln Leu Phe Asp Arg Thr
            20

<210> SEQ ID NO 282
<211> LENGTH: 26
<212> TYPE: PRT
<213> ORGANISM: Homo sapiens

<400> SEQUENCE: 282

Glu Asp Gln Thr Thr Glu Phe Lys Glu Ala Phe Gln Leu Phe Asp Arg
1               5                   10                  15

Thr Gly Asp Gly Lys Ile Leu Tyr Asn Gln
            20                  25

<210> SEQ ID NO 283
<211> LENGTH: 24
<212> TYPE: PRT
<213> ORGANISM: Homo sapiens

<400> SEQUENCE: 283

Ser Thr Ser Val Pro Glu Asn Pro Lys Ser Ser Ala Ser Thr Ala Val
1               5                   10                  15

-continued

Ser Ala Ala Pro Thr Glu Lys Glu
            20

<210> SEQ ID NO 284
<211> LENGTH: 19
<212> TYPE: PRT
<213> ORGANISM: Homo sapiens

<400> SEQUENCE: 284

Glu Leu Thr Ser Gln Ala Glu Arg Ala Glu Leu Gly Gln Glu Leu
1               5                   10                  15

Lys Ala Trp

<210> SEQ ID NO 285
<211> LENGTH: 23
<212> TYPE: PRT
<213> ORGANISM: Homo sapiens

<400> SEQUENCE: 285

Asn Leu Lys Arg Tyr Leu Lys Ser Glu Pro Ile Pro Glu Ser Asn Asp
1               5                   10                  15

Gly Pro Val Lys Val Val Val
            20

<210> SEQ ID NO 286
<211> LENGTH: 18
<212> TYPE: PRT
<213> ORGANISM: Homo sapiens

<400> SEQUENCE: 286

Ala Pro Glu Lys Pro Val Lys Lys Gln Lys Thr Gly Glu Thr Ser Arg
1               5                   10                  15

Ala Leu

<210> SEQ ID NO 287
<211> LENGTH: 42
<212> TYPE: PRT
<213> ORGANISM: Homo sapiens

<400> SEQUENCE: 287

Gly Ile Asn Gln Lys Leu Leu Ala Glu Ala Leu Asn Gln Val Thr Gln
1               5                   10                  15

Arg Ala Ser Arg Arg Ser Asp Ser Ala Ser Ser Glu Pro Val Gly Ile
            20                  25                  30

Tyr Gln Gly Phe Glu Lys Lys Thr Gly Val
            35                  40

<210> SEQ ID NO 288
<211> LENGTH: 36
<212> TYPE: PRT
<213> ORGANISM: Homo sapiens

<400> SEQUENCE: 288

Ile Ile Gly Arg Cys Thr Gly Thr Ala Ala Asn Ser Arg Asp Thr Ile
1               5                   10                  15

Phe Gln Lys Glu Arg Phe Asn Ile Asp Met Pro His Arg Phe Lys Val
            20                  25                  30

His Asn Tyr Met
            35

<210> SEQ ID NO 289

<211> LENGTH: 30
<212> TYPE: PRT
<213> ORGANISM: Homo sapiens

<400> SEQUENCE: 289

Gly Gln Thr Ser Thr Lys Gln Lys Thr Asn Lys Pro Thr Tyr Asn Glu
1               5                   10                  15

Glu Phe Cys Ala Asn Val Thr Asp Gly Gly His Leu Glu Leu
            20                  25                  30

<210> SEQ ID NO 290
<211> LENGTH: 35
<212> TYPE: PRT
<213> ORGANISM: Homo sapiens

<400> SEQUENCE: 290

Cys Ala Asn Val Thr Asp Gly Gly His Leu Glu Leu Ala Val Phe His
1               5                   10                  15

Glu Thr Pro Leu Gly Tyr Asp His Phe Val Ala Asn Cys Thr Leu Gln
            20                  25                  30

Phe Gln Glu
        35

<210> SEQ ID NO 291
<211> LENGTH: 19
<212> TYPE: PRT
<213> ORGANISM: Homo sapiens

<400> SEQUENCE: 291

Gly His Leu Phe Gln Ala Lys Arg Phe Asn Arg Arg Ala Tyr Cys Gly
1               5                   10                  15

Gln Cys Ser

<210> SEQ ID NO 292
<211> LENGTH: 40
<212> TYPE: PRT
<213> ORGANISM: Homo sapiens

<400> SEQUENCE: 292

Pro Leu Thr Leu Lys Trp Val Asp Ser Glu Gly Asp Pro Cys Thr Val
1               5                   10                  15

Ser Ser Gln Met Glu Leu Glu Glu Ala Phe Arg Leu Ala Arg Gln Cys
            20                  25                  30

Arg Asp Glu Gly Leu Ile Ile His
        35                  40

<210> SEQ ID NO 293
<211> LENGTH: 31
<212> TYPE: PRT
<213> ORGANISM: Homo sapiens

<400> SEQUENCE: 293

Val Thr Gln Phe Asn Lys Val Ala Gly Ala Val Val Ser Ser Val Leu
1               5                   10                  15

Gly Ala Thr Ser Thr Gly Glu Gly Pro Gly Glu Val Thr Ile Arg
            20                  25                  30

<210> SEQ ID NO 294
<211> LENGTH: 36
<212> TYPE: PRT
<213> ORGANISM: Homo sapiens -continued

```
<400> SEQUENCE: 294

Asn Leu Glu Asn Pro Ser Cys Asn Ser Val Leu Asp Pro Arg Asp Leu
1               5                   10                  15

Arg Gln Leu His Gln Met Ser Ser Ser Met Ser Ala Gly Ala Asn
            20                  25                  30

Ser Asn Thr Thr
        35

<210> SEQ ID NO 295
<211> LENGTH: 47
<212> TYPE: PRT
<213> ORGANISM: Homo sapiens

<400> SEQUENCE: 295

Glu Gln Ser Gln Ala Pro Ile Thr Pro Gln Gln Gly Gln Ala Leu Ala
1               5                   10                  15

Lys Gln Ile His Ala Val Arg Tyr Leu Glu Cys Ser Ala Leu Gln Gln
            20                  25                  30

Asp Gly Val Lys Glu Val Phe Ala Glu Ala Val Arg Ala Val Leu
        35                  40                  45

<210> SEQ ID NO 296
<211> LENGTH: 20
<212> TYPE: PRT
<213> ORGANISM: Homo sapiens

<400> SEQUENCE: 296

Gly Trp Met Glu Glu Gln Ser Gln Ala Pro Ile Thr Pro Gln Gln Gly
1               5                   10                  15

Gln Ala Leu Glu
        20

<210> SEQ ID NO 297
<211> LENGTH: 35
<212> TYPE: PRT
<213> ORGANISM: Homo sapiens

<400> SEQUENCE: 297

Lys Glu Gln Ser Gln Ala Pro Ile Thr Pro Gln Gln Gly Gln Ala Leu
1               5                   10                  15

Ala Lys Gln Ile His Ala Val Arg Tyr Leu Glu Cys Ser Ala Leu Gln
            20                  25                  30

Gln Asp Gly
        35

<210> SEQ ID NO 298
<211> LENGTH: 18
<212> TYPE: PRT
<213> ORGANISM: Homo sapiens

<400> SEQUENCE: 298

Thr Pro Gln Gln Gly Gln Ala Leu Ala Lys Gln Ile His Ala Val Arg
1               5                   10                  15

Tyr Leu

<210> SEQ ID NO 299
<211> LENGTH: 20
<212> TYPE: PRT
<213> ORGANISM: Homo sapiens

<400> SEQUENCE: 299
```

```
Ser Arg Ile Arg Val His Leu Thr Pro Ala Ala Ser Thr Met Leu Pro
1               5                   10                  15

Lys Phe Asn Pro
            20
```

<210> SEQ ID NO 300
<211> LENGTH: 17
<212> TYPE: PRT
<213> ORGANISM: Homo sapiens

<400> SEQUENCE: 300

```
Gly Glu Lys Lys Lys Gly Arg Ser Ala Ile Asn Glu Val Val Thr Arg
1               5                   10                  15

Glu
```

<210> SEQ ID NO 301
<211> LENGTH: 22
<212> TYPE: PRT
<213> ORGANISM: Homo sapiens

<400> SEQUENCE: 301

```
Trp Met Asp Gly Arg Met Lys Lys Val Arg Gly Thr Ala Lys Ala Asn
1               5                   10                  15

Val Gly Ala Gly Lys Lys
            20
```

<210> SEQ ID NO 302
<211> LENGTH: 40
<212> TYPE: PRT
<213> ORGANISM: Homo sapiens

<400> SEQUENCE: 302

```
Glu Ser Gln Glu His Pro Glu Ala Asp Pro Gly Ser Ala Ala Pro Tyr
1               5                   10                  15

Leu Lys Thr Lys Phe Ile Cys Val Thr Pro Thr Thr Cys Ser Asn Thr
            20                  25                  30

Ile Asp Leu Pro Met Ser Pro Arg
            35                  40
```

<210> SEQ ID NO 303
<211> LENGTH: 32
<212> TYPE: PRT
<213> ORGANISM: Homo sapiens

<400> SEQUENCE: 303

```
Asp Val Arg Lys Arg Val Gln Asp Leu Glu Gln Lys Met Lys Val Val
1               5                   10                  15

Glu Asn Leu Gln Asp Asp Phe Asp Phe Asn Tyr Lys Thr Leu Lys Ser
            20                  25                  30
```

<210> SEQ ID NO 304
<211> LENGTH: 38
<212> TYPE: PRT
<213> ORGANISM: Homo sapiens

<400> SEQUENCE: 304

```
Phe Leu Gln Glu Ser Asn Val Leu Tyr Gln His Asn Leu Arg Arg Ile
1               5                   10                  15

Lys Gln Phe Leu Gln Ser Arg Tyr Leu Glu Lys Pro Met Glu Ile Ala
            20                  25                  30
```

Arg Ile Val Ala Arg Cys
        35

<210> SEQ ID NO 305
<211> LENGTH: 15
<212> TYPE: PRT
<213> ORGANISM: Homo sapiens

<400> SEQUENCE: 305

Asp Gln Gln Tyr Ser Arg Phe Leu Gln Glu Ser Asn Val Leu Tyr
1               5                   10                  15

<210> SEQ ID NO 306
<211> LENGTH: 35
<212> TYPE: PRT
<213> ORGANISM: Homo sapiens

<400> SEQUENCE: 306

Asn Lys Gln Gln Ala His Asp Leu Leu Ile Asn Lys Pro Asp Gly Thr
1               5                   10                  15

Phe Leu Leu Arg Phe Ser Asp Ser Glu Ile Gly Gly Ile Thr Ile Ala
                20                  25                  30

Trp Lys Phe
        35

<210> SEQ ID NO 307
<211> LENGTH: 34
<212> TYPE: PRT
<213> ORGANISM: Homo sapiens

<400> SEQUENCE: 307

Lys Arg Ile Lys Arg Ser Asp Arg Arg Gly Ala Glu Ser Val Thr Glu
1               5                   10                  15

Glu Lys Phe Thr Ile Leu Phe Glu Ser Gln Phe Ser Val Gly Gly Asn
                20                  25                  30

Glu Leu

<210> SEQ ID NO 308
<211> LENGTH: 15
<212> TYPE: PRT
<213> ORGANISM: Homo sapiens

<400> SEQUENCE: 308

Thr Ile Leu Phe Glu Ser Gln Phe Ser Val Gly Gly Asn Glu Leu
1               5                   10                  15

<210> SEQ ID NO 309
<211> LENGTH: 40
<212> TYPE: PRT
<213> ORGANISM: Homo sapiens

<400> SEQUENCE: 309

Gln His Gly Lys Val Val Thr Trp Arg Thr Ala Thr Leu Cys Pro Gln
1               5                   10                  15

Ser Cys Glu Glu Arg Asn Leu Arg Glu Asn Gly Tyr Glu Cys Glu Trp
                20                  25                  30

Arg Tyr Asn Ser Cys Ala Pro Ala
        35                  40

<210> SEQ ID NO 310

```
<211> LENGTH: 28
<212> TYPE: PRT
<213> ORGANISM: Homo sapiens

<400> SEQUENCE: 310

Ala Arg Thr Cys Ala Gln Glu Gly Met Val Leu Tyr Gly Trp Thr Asp
1               5                   10                  15

His Ser Ala Cys Ser Pro Val Cys Pro Ala Gly Met
            20                  25

<210> SEQ ID NO 311
<211> LENGTH: 24
<212> TYPE: PRT
<213> ORGANISM: Homo sapiens

<400> SEQUENCE: 311

Cys Cys Gly Arg Cys Leu Pro Ser Ala Cys Glu Val Val Thr Gly Ser
1               5                   10                  15

Pro Arg Gly Asp Ser Gln Ser Ser
            20

<210> SEQ ID NO 312
<211> LENGTH: 20
<212> TYPE: PRT
<213> ORGANISM: Homo sapiens

<400> SEQUENCE: 312

Val Ser Gln Gly Asp Arg Glu Gln Ala Pro Asn Leu Val Tyr Met Val
1               5                   10                  15

Thr Gly Asn Pro
            20

<210> SEQ ID NO 313
<211> LENGTH: 21
<212> TYPE: PRT
<213> ORGANISM: Homo sapiens

<400> SEQUENCE: 313

Cys His Thr Val Thr Cys Gln Pro Asp Gly Gln Thr Leu Leu Lys Ser
1               5                   10                  15

His Arg Val Asn Cys
            20

<210> SEQ ID NO 314
<211> LENGTH: 21
<212> TYPE: PRT
<213> ORGANISM: Homo sapiens

<400> SEQUENCE: 314

Ser Thr Ser Glu Val Leu Lys Tyr Thr Leu Phe Gln Ile Phe Ser Lys
1               5                   10                  15

Ile Asp Arg Pro Glu
            20
```

REAGENTS AND METHODS FOR IDENTIFYING GENE TARGETS FOR TREATING CANCER

This application claims priority to U.S. Provisional Application Ser. No.: 60/306,730, filed Jul. 20, 2001.

This invention was made with government support under R01 CA62099 awarded by the National Institutes of Health. The government has certain rights in the invention.

BACKGROUND OF THE INVENTION

1. Field of the Invention

The invention is related to methods and reagents for inhibiting tumor cell growth. Specifically, the invention identifies genes necessary for tumor cell growth as targets for developing drugs to inhibit such genes and thereby inhibit tumor growth. The invention provides methods for screening compounds to identify inhibitors of said genes, and methods for using said inhibitors to inhibit tumor cell growth. The invention also provides peptides encoded by genetic suppressor elements of the invention and mimetics and analogues thereof for inhibiting tumor cell growth. Also provided by the invention are normalized random fragment cDNA libraries prepared from tumor cells of one or a plurality of tumor cell types wherein the cDNA fragments can be induced by treating recipient cells with a physiologically-neutral stimulating agent.

2. Summary of the Related Art

The completion of the draft sequence of the human genome has provided the art with a partial list of known and putative human genes, the total number of which is estimated to be between 30,000 and 45,000 (Venter et al., 2001, *Science* 291: 1304–1351; Lander et al., 2001, *Nature* 409: 860–921). These genes provide many potential targets for drugs, some of which may be useful in preventing the growth of cancers. However, the development of clinically useful gene-targeting anticancer drugs could be greatly facilitated by the ability to narrow down the list of human genes to those that are involved in the primary feature of cancer, uncontrolled tumor growth. It would be especially useful to identify genes necessary for the growth of tumor cells and to determine which of the genes play a tumor-specific role and are not required for normal cell growth. These genes are particularly attractive targets for developing tumor-specific anticancer agents.

Most of the effort in tumor-specific drug targeting in the prior art has focused on oncogenes, the function of which has been associated with different forms of cancer Perkins and Stem (1997, in CANCER: PRINCIPLES AND PRACTICE OF ONCOLOGY, DeVita et al., eds., (Philadelphia: Lippincott-Raven), pp. 79–102). Oncogene targets have been viewed in the art as being more "tumor-specific" than "normal" cellular enzymes that are targeted by the drugs used in present chemotherapeutic regimens. The tumor specificity of oncogenes has been suggested primarily by the existence of oncogene-associated genetic changes, such as mutations or rearrangements, specific to neoplastic cells. Although oncogenes are mutated or rearranged in some cases, in other cases they are merely expressed at elevated levels or at inappropriate stages of the cell cycle, without changes in the structure of the gene product (Perkins and Stem, 1997, Id.). Even when mutated, proteins encoded by oncogenes rarely acquire a qualitatively novel function relative to the "normal" protooncogene products. Hence, products of mutated, rearranged or overexpressed oncogenes generally perform the same biochemical functions as their normal cell counterparts, except that the functions of the activated oncogene products are abnormally regulated.

It is noteworthy that none of the "classical" oncogenes known in the art have been identified as targets for clinically useful anticancer drugs discovered by traditional mechanism-independent screening procedures. Rather the known cellular targets of chemotherapeutic drugs, such as dihydrofolate reductase (inhibited by methotrexate and other antifolates), topoisomerase II ("poisoned" by epipodophyllotoxins, anthracyclines or acridine drugs), or microtubules that form the mitotic spindle (the targets of Vinca alkaloids and taxanes) are essential for growth and proliferation of both normal and neoplastic cells. Tumor selectivity of anticancer drugs appears to be based not merely on the fact that their targets function primarily in proliferating cells, but rather on tumor-specific response to the inhibition of anticancer drug targets. For example, Scolnick and Halazonetis (2000, *Nature* 406 430–435) disclosed that a high fraction of tumor cell lines are deficient in a gene termed CHFR. In the presence of antimicrotubular drugs, CHFR appears to arrest the cell cycle in prophase. CHFR-deficient tumor cells, however, proceed into drug-impacted abnormal metaphase (Scolnick and Halazonetis, 2000, Id.), where they die through mitotic catastrophe or apoptosis (Torres and Horwitz, 1998, *Cancer Res.* 58: 3620–3626). In addition to CHFR, tumor cells are frequently deficient in various cell cycle checkpoint controls, and exploiting these deficiencies is a major direction in experimental therapeutics (O'Connor, 1997, *Cancer Surv.* 29: 151–182; Pihan and Doxsey, 1999, *Semin. Cancer Biol.* 9: 289–302). In most cases, however, the reasons that inhibition of anticancer drug targets selectively induces cell death or permanent growth arrest in tumor cells are unknown. There is therefore need in the art to identify additional molecular targets in tumor cells, inhibition of which would arrest tumor cell growth.

One method known in the art for identifying unknown genes or unknown functions of known genes is genetic suppressor element technology, developed by some of the present inventors (in U.S. Pat. Nos. 5,217,889, 5,665,550, 5,753,432, 5,811,234, 5,866,328, 5,942,389, 6,043,340, 6,060,134, 6,083,745, 6,083,746, 6,197,521, 6,268,134, 6,281,011 and 6,326,488, each of which is incorporated by reference in its entirety). Genetic suppressor elements (GSEs) are biologically active cDNA fragments that interfere with the function of the gene from which they are derived. GSEs may encode antisense RNA molecules that inhibit gene expression or peptides corresponding to functional protein domains, which interfere with protein function as dominant inhibitors. The general strategy for the isolation of biologically active GSEs involves the preparation of an expression library containing randomly fragmented DNA of the target gene or genes. This library is then introduced into recipient cells, followed by selection for the desired phenotype and recovery of biologically active GSEs from the selected cells. By using a single cDNA as the starting material for GSE selection, one can generate specific inhibitors of the target gene and map functional domains in the target protein. By using a mixture of multiple genes or the entire genome as the starting material, GSE selection allows one to identify genes responsible for a specific cellular function, since such genes will give rise to GSEs inhibiting this function. In a variation of this approach, the vector used for library preparation contains sequences permitting regulated expression of cDNA fragments cloned therein.

This method can be used to identify genes required for tumor cell growth by subjecting the cells to negative growth selection. One example of this type of selection is known in the art as bromodeoxyuridine (BrdU) suicide selection, which has long been used to select conditional-lethal mutants (Stetten et al., 1977, *Exp. Cell Res.* 108: 447–452) and growth-inhibitory DNA sequences (Padmanabhan et al., 1987, *Mol. Cell Biol.* 7: 1894–1899). The basis of BrdU suicide selection is the destruction of cells that replicate their DNA in the presence of BrdU. BrdU is a photoactive nucleotide that incorporates into DNA and causes lethal DNA crosslinking upon illumination with white light in the presence of Hoechst 33342. The only cells that survive this selection are cells that do not replicate their DNA while BrdU is present, such as cells that express growth-inhibitory genes or GSEs. One advantage of this method is very low background of surviving cells. When used with GSE libraries under the control of an inducible vector, this selection method excludes spontaneously arising BrdU-resistant mutants by the insensitivity of their phenotype to the presence or absence of the inducing agent. Another major advantage of this technique is its sensitivity for weak growth-inhibitory GSEs: even if only a small fraction of GSE-containing cells are growth-inhibited by GSE induction, such cells will survive BrdU suicide and will give rise to a recovering clone.

The applicability of this approach to the isolation of growth-inhibitory GSEs was first demonstrated by Pestov and Lau (1994, *Proc. Natl. Acad. Sci. USA* 91: 12549–12553). These workers used an IPTG-inducible plasmid expression vector to isolate cytostatic GSEs from a mixture of cDNA fragments from 19 murine genes associated with the $G_0/G_1$ transition. In this work, three of the genes in the mixture gave rise to growth-inhibitory GSEs (Pestov and Lau, 1994, Id.). In a subsequent study, Pestov et al. (1998, *Oncogene* 17: 13187–3197) used the same approach to isolate one full-length and one truncated cDNA clone with growth-inhibitory activity from a 40,000-clone library of nominally full-length mouse cDNA. However, the method disclosed in the art cannot be efficiently used for transducing a library of random fragments representing the total mRNA population from a mammalian cell such as a tumor cell because the method relies on plasmid expression vectors for library construction, and only a limited number of cells can be stably transfected by such libraries.

There remains a need in the art to discover novel genes and novel functions of known genes necessary for tumor cell growth, especially by using methods for identifying genes based on function. There is also a need in the art to identify targets for therapeutic drug treatment, particularly targets for inhibiting tumor cell growth, and to develop compounds that inhibit the identified targets and thereby inhibit tumor cell growth.

SUMMARY OF THE INVENTION

The present invention identifies genes that are targets for developing drugs for the treatment of cancer by inhibiting tumor cell growth. Such genes are identified as disclosed herein through expression selection of genetic suppressor elements (GSEs) that inhibit the growth of tumor cells in vitro. This selection has revealed multiple genes, some of which have been previously known to play a role in cell proliferation, whereas others were not known to be involved in cell proliferation prior to instant invention; the latter genes constitute novel drug targets and are set forth in Table 3.

In a first embodiment, the invention provides a method identifying a compound that inhibits growth of a mammalian cell, the method comprising the steps of:

(a) culturing a cell in the presence or absence of the compound;
(b) assaying the cell for expression or activity in the sample of one or a plurality of the genes set forth in Table 3; and
(c) identifying the compound when expression or activity in the sample of at least one of the genes set forth in Table 3 is lower in the presence of the compound than in the absence of the compound.

In preferred embodiments, the cell is a mammalian cell, preferably a human cell, and most preferably a human tumor cell. In further preferred embodiments, gene inhibition is detected by hybridization with a nucleic acid complementary to the gene, biochemical assay for an activity of the gene or immunological reaction with an antibody specific for an antigen comprising the gene product. In a preferred embodiment, the cell is a recombinant cell in which a reporter gene is operably linked to a promoter from a cellular gene in Table 3, to detect decreased expression of the reporter gene in the presence of the compound than in the absence of the compound. In further preferred embodiments, the cell is assayed for cell growth in the presence and absence of the compound, to identify compounds that inhibit cell growth and a gene identified in Table 3.

The invention also provides compounds that inhibit tumor cell growth that are identified by the methods of the invention, and pharmaceutical formulations of said compounds. The invention specifically provides peptides encoded by sense-oriented genetic suppressor elements of the invention. In addition the invention provides peptide mimetics comprising all or a portion of any of said peptides, peptido-, organo- or chemical mimetics thereof.

In a second embodiment, the invention provides a method for assessing efficacy of a treatment of a disease or condition relating to abnormal cell proliferation or tumor cell growth, comprising the steps of:

(a) obtaining a biological sample comprising cells from an animal having a disease or condition relating to abnormal cell proliferation or tumor cell growth before treatment and after treatment with a compound that inhibits expression or activity of a gene identified in Table 3;
(b) comparing expression or activity of at least one gene in Table 3 after treatment with the compound with expression or activity of said genes before treatment with the compound; and
(c) determining that said treatment with the compound has efficacy for treating the disease or condition relating to abnormal cell proliferation or neoplastic cell growth if expression or activity of at least one gene in Table 3 is lower after treatment than before treatment.

In preferred embodiments, the cell is a mammalian, most preferably human cell, most preferably a tumor cell.

In a third aspect, the invention provides a method for inhibiting tumor cell growth, the method comprising the steps of contacting a tumor cell with an effective amount of a compound that inhibits expression of a gene in Table 3.

In a fourth aspect, the invention provides a method for treating a disease or condition relating to abnormal cell proliferation or tumor cell growth, the method comprising the steps of administering to an animal having said disease or condition a therapeutically effective amount of a compound that inhibits expression of a gene in Table 3.

Pharmaceutically acceptable compositions effective according to the methods of the invention, comprising a therapeutically effective amount of a peptide or peptide mimetic of the invention capable of inhibiting tumor cell growth and a pharmaceutically acceptable carrier or diluent, are also provided.

Specific preferred embodiments of the present invention will become evident from the following more detailed description of certain preferred embodiments and the claims.

BRIEF DESCRIPTION OF THE DRAWINGS

FIG. 7A shows the effects on cell morphology of four-day treatment with IPTG. FIG. 7B shows evidence of mitotic catastrophe in IPTG-treated cells.

DETAILED DESCRIPTION OF PREFERRED EMBODIMENTS

Figure 1:
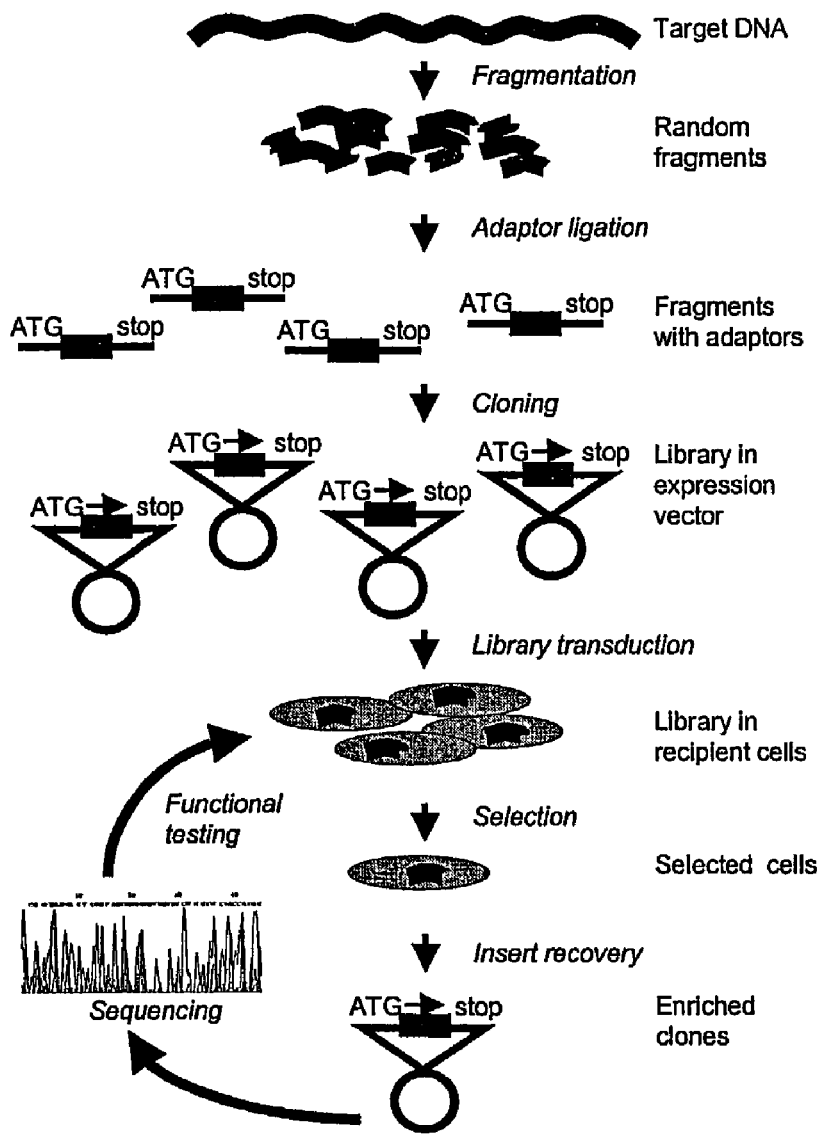
FIG. 1 is a schematic diagram illustrating the principles of genetic suppressor element technology.

This invention provides target genes involved in cell growth, preferably tumor cell growth, methods for identifying compounds that inhibit expression or activity of these genes and methods for specifically inhibiting tumor cell growth by inhibiting expression or activity of these genes. Preferably, the methods of the invention do not substantially affect normal cell growth.

This invention provides methods for identifying genes that are required for tumor cell growth. Such genes, which are potential targets for new anticancer drugs, are identified through expression selection of genetic suppressor elements (GSEs). GSEs are biologically active sense- or antisense-oriented cDNA fragments that inhibit the function of the gene from which they are derived. Expression of GSEs derived from genes involved in cell proliferation is expected to inhibit cell growth. According to the inventive methods, such GSEs are isolated by so-called "suicide selection" of cells the growth of which is inhibited under cell culture conditions in which growing cells are specifically killed. In a preferred embodiment the suicide selection protocol is bromodeoxyuridine (BrdU) suicide selection, in which cells are incubated with BrdU and then illuminated with bright light. Growing cells incorporate BrdU into chromosomal DNA, making the DNA sensitive to illumination with light, which specifically kills growing cells. GSEs are produced starting from a normalized (reduced-redundance) library of human cDNA fragments in an inducible retroviral vector. In preferred embodiments, the recipient cells are tumor cells, most preferably human tumor cells, for example breast carcinoma cells.

For the purposes of this invention, reference to "a cell" or "cells" is intended to be equivalent, and particularly encompasses in vitro cultures of mammalian cells grown and maintained as known in the art.

For the purposes of this invention, reference to "cellular genes" in the plural is intended to encompass a single gene as well as two or more genes. It will also be understood by those with skill in the art that effects of modulation of cellular gene expression, or reporter constructs under the transcriptional control of promoters derived from cellular genes, can be detected in a first gene and then the effect replicated by testing a second or any number of additional genes or reporter gene constructs. Alternatively, expression of two or more genes or reporter gene constructs can be assayed simultaneously within the scope of this invention.

Recombinant expression constructs can be introduced into appropriate mammalian cells as understood by those with skill in the art. Preferred embodiments of said constructs are produced in transmissible vectors, more preferably viral vectors and most preferably retrovirus vectors, adenovirus vectors, adeno-associated virus vectors, and vaccinia virus vectors, as known in the art. See, generally, MAMMALIAN CELL BIOTECHNOLOGY: A PRACTICAL APPROACH, (Butler, ed.), Oxford University Press: New York, 1991, pp. 57–84.

In additionally preferred embodiments, the recombinant cells of the invention contain a construct encoding an inducible retroviral vector comprising random cDNA fragments from total tumor cell mRNA, wherein the fragments are each under the transcriptional control of an inducible promoter. In more preferred embodiments, the inducible promoter is responsive to a trans-acting factor whose effects can be modulated by an inducing agent. The inducing agent can be any factor that can be manipulated experimentally, including temperature and most preferably the presence or absence of an inducing agent. Preferably, the inducing agent is a chemical compound, most preferably a physiologically-neutral compound that is specific for the trans-acting factor. In the use of constructs comprising inducible promoters as disclosed herein, expression of the random cDNA fragments from the recombinant expression construct is mediated by contacting the recombinant cell with an inducing agent that induces transcription from the inducible promoter or by removing an agent that inhibits transcription from such promoter. A variety of inducible promoters and cognate trans-acting factors are known in the prior art, including heat shock promoters than can be activated by increasing the temperature of the cell culture, and more preferably promoter/factor pairs such as the tet promoter and fusions thereof with mammalian transcription factors (as are disclosed in U.S. Pat. Nos. 5,654,168, 5,851,796, and 5,968,773), and the bacterial lac promoter of the lactose operon and its cognate lacI repressor protein. In a preferred embodiment, the recombinant cell expresses the lacI repressor protein and a recombinant expression construct encoding the random cDNA fragments under the control of a promoter comprising one or a multiplicity of lac-responsive elements, wherein expression of the fragments can be induced by contacting the cells with the physiologically-neutral inducing agent, isopropylthio-β-galactoside. In this preferred embodiment, the lacI repressor is encoded by a recombinant expression construct identified as 3'SS (commercially available from Stratagene, LaJolla, Calif.).

The invention also provides recipient cell lines suitable for selection of growth-inhibitory GSEs. In preferred embodiments, the cell lines are human breast, lung, colon and prostate carcinoma cells, modified to comprise a trans-acting factor such as the lac repressor and further to express a retroviral receptor cognate to the tropism of the retroviral vector in which the library is constructed. In a preferred embodiment, the cells are modified to express the bacterial lac operon repressor, lacI (to allow for IPTG-inducible gene expression) and to express the ecotropic mouse retroviral receptor (to enable high-efficiency infection with ecotropic recombinant retroviruses). In alternative preferred embodiments, the cells are telomerase-immortalized normal human fibroblasts and retinal pigment and mammary epithelial cells that have been modified to express lacI and the mouse ecotropic retrovirus receptor.

The invention utilizes modifications of methods of producing genetic suppressor elements (GSEs) for identifying tumor cell growth controlling genes. These DNA fragments are termed "GSE" herein to designate both sense- and antisense-oriented gene fragments that can inhibit or modify the function of the target gene when expressed in a cell. Both types of functional GSEs can be generated by random fragmentation of the DNA of the target gene and identified by function-based selection of fragments that confer the desired cellular phenotype such as cell growth inhibition. Such function-based GSE selection makes it possible to develop genetic inhibitors for the selected targets, identify protein functional domains, and identify genes involved in various complex phenotypes.

Figure 2:
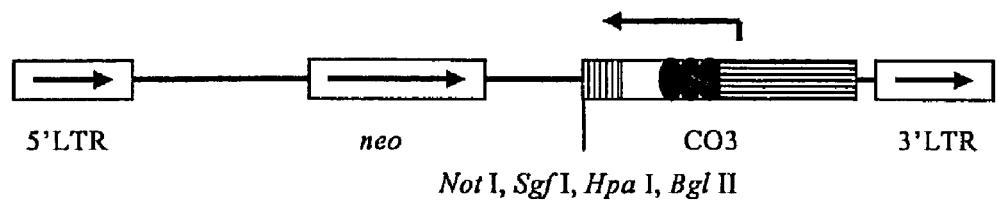
FIG. 2 is a schematic diagram of the structure of the LNCXCO3 retroviral vector.

A generalized scheme of GSE selection is shown in FIG. 1. Originally developed using a model bacterial system (see U.S. Pat. No. 5,217,889, incorporated by reference), this method has been adapted for use in mammalian cells. Because less than 1% of random fragments derived from a typical cDNA have GSE activity, the size of expression libraries required for GSE selection is much larger than the corresponding size of libraries that can be used for function-based selection of full-length cDNAs. Retroviral vectors are used to deliver such large libraries into mammalian cells, because it is a non-stressful delivery system that can be used for stable transduction into a very high fraction (up to 100%) of recipient cells. In the preparation of these retroviral-based libraries, packaging cell lines are used, most preferably human 293-based packaging cell lines, such as BOSC23 (Pear et al., 1993, *Proc. Natl. Acad. Sci. USA* 90: 8392–8396), which provide efficient and uniform retrovirus packaging after transient transfection (Gudkov and Roninson, 1997, in METHODS IN MOLECULAR BIOLOGY: cDNA LIBRARY PROTOCOLS, Cowell and Austin, eds. (Totowa, N.J.: Humana Press), pp. 221–240). Additionally, large-scale expression selection required modifications in conventional retroviral vectors. The retroviral vectors used to produce the normalized tumor libraries of the invention carry one constitutively expressing and one inducible promoter, which minimizes the problem of promoter interference under non-inducing conditions. Preferred embodiments of the modified retroviral vectors of the invention express the bacterial neomycin resistance gene (neo, selectable in mammalian cells with G418) from an LTR promoter in the retrovirus. The vectors also contain a multiple cloning site 3' to the selectable marker gene and adjacent to a regulatable promoter comprising promoters from cytomegalovirus (CMV) or *Rous sarcoma* virus (RSV) LTR containing 2–4 bacterial lac operator sequences. The regulatable promoter is cloned in the anti orientation to the retroviral LTR. A diagram of the topography of one of these viruses, LNXCO3 is shown in FIG. 2. In alternative embodiments, the neo gene is exchanged for a gene encoding green fluorescent protein (Kandel et al., 1997, *Somat. Cell Genet.* 23: 325–340) or firefly luciferase (Chang et al., 1999, *Oncogene* 18: 4808–4818). As a positive control for growth inhibition an embodiment of LNXCO3 was used that expressed human p21, a CDK inhibitor know to strongly inhibit tumor cell growth (see International Patent Application, Publication No. WO01/38532, incorporated by reference).

The invention provides a normalized cDNA fragment library from a mixture of poly(A)+RNA preparations from one or a multiplicity of human cell lines, derived from different types of cancer. This normalized library is prepared in a vector, preferably a retroviral vector and most preferably a retroviral vector containing sequences permitting regulated expression of cDNA fragments cloned therein. In a preferred embodiment, the vector is the retroviral vector LNXCO3, comprising a promoter inducible by isopropyl-β-thio-galactoside (IPTG), a physiologically neutral agent.

Figure 3:
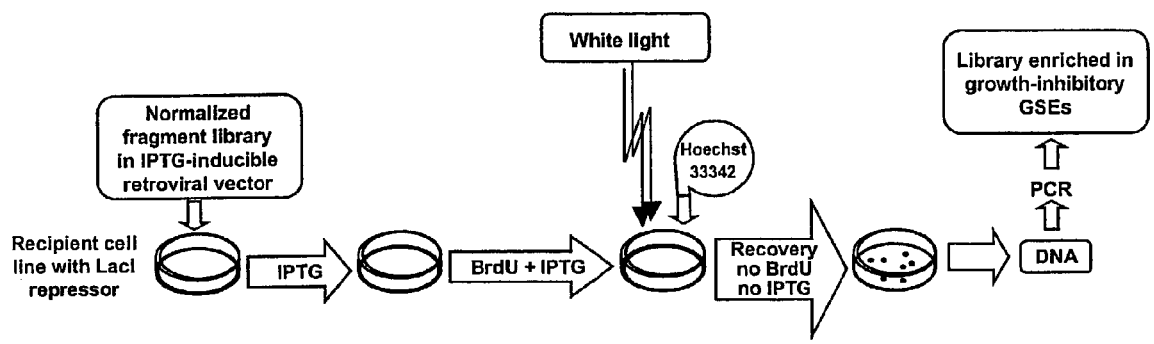
FIG. 3 is a schematic diagram of the BrdU selection protocol.

The invention provides methods for isolating growth-inhibitory GSEs from a normalized cDNA fragment library, representing most of the expressed genes in a human tumor cell. As provided herewith, normalized cDNA fragment libraries contain on the order of $5 \times 10^7$ clones (Gudkov et al., 1994, *Proc. Natl. Acad. Sci. USA* 91: 3644–3748; Levenson et al., 1999, *Somat. Cell Molec. Genet.* 25: 9–26), corresponding to >1,000 cDNA fragments per gene. Selection of individual GSEs from a library of this size requires a procedure with high sensitivity and low background, most preferably BrdU suicide selection. The principle of BrdU suicide selection is illustrated in FIG. 3. In preferred embodiments, the GSEs are expressed under the control of an inducible promoter, most preferably a promoter that is inducible by a physiologically neutral agent (such as IPTG), provided that the growth inhibitor is induced prior to the addition of BrdU. Following BrdU selection, the inducer is washed from the culture and cells infected with growth-inhibitory GSEs begin to proliferate, thus providing colonies of cells harboring selected GSEs.

BrdU suicide is not the only technique that can be used to select growth-inhibitory genes or GSEs. In one alternative approach, cells are labeled with a fluorescent dye that integrates into the cell membrane and is redistributed between daughter cells with each round of cell division. As a result, cells that have divided the smallest number of times after labeling show the highest fluorescence and can be isolated by FACS (Maines et al., 1995, *Cell Growth Differ.* 6: 665–671). It is also possible to isolate cells that die upon the addition of the inducer, by collecting floating dead cells or isolating apoptotic cells on the basis of altered staining with DNA-binding fluorescent dyes. These methods have been used to isolate GSEs from single-gene cDNA fragment libraries prepared from the MDR1 gene (Zuhn, 1996, Ph.D. Thesis, Department of Genetics, University of Illinois at Chicago, Chicago, Ill.) or from BCL2 (U.S. Pat. No. 5,789,389, incorporated by reference). There are no theoretical problems with any of these approaches, and all of them work to enrich for growth-inhibitory elements in low-complexity libraries. The only disadvantage of these alternatives when compared with BrdU selection is that they have higher spontaneous background rates that may prevent rare clones to be selected from an exceedingly complex normalized library. Thus, BrdU selection is the preferred embodiment of the inventive methods.

Prior art methods (Pestov and Lau, 1994, Id.) for adapting GSE technology to identify growth-inhibitory GSEs were of limited utility when applied to total tumor cell cDNA. The prior art methods cannot be efficiently used for transducing a library representing the total mRNA population from a mammalian cell such as a tumor cell because the method relies on plasmid expression vectors for library construction, and only a limited number of cells can be stably transfected by such libraries. To overcome this limitation, the invention provides a set of inducible retroviral vectors that are regulated by IPTG through the bacterial LacI repressor. This inducible system provides comparable levels of induction among most of the infected cells. The induced levels of expression can be finely regulated by using different doses of IPTG.

The methods of the invention are exemplified herein by use of this IPTG-inducible retroviral system to generate a normalized cDNA library from human breast cancer cells. This library was used to select GSEs that induce growth arrest in a breast carcinoma cell line. Using this approach, more than 90 genes were identified that were enriched by BrdU suicide selection. Many of these GSEs were shown to have a growth-inhibiting effect when re-introduced into tumor cells. Included in the genes identified using the inventive methods are known oncogenes, some of which have been specifically associated with breast cancer, as well as other genes with a known role in cell proliferation. Many of the identified genes, however, had no known function or were not previously known to play a role in cell cycle progression. The latter genes and their products represent therefore novel targets for cancer treatment. Furthermore, some of the genes giving rise to the GSEs that inhibited the proliferation of breast carcinoma cells appear to be inessential for normal cell growth, since homozygous knockout of these genes does not prevent the development of adult mice.

The invention provides methods for cloning unknown genes containing GSEs identified using GSE libraries and negative growth selection methods of the invention. In the practice of this aspect of the methods of the invention, GSEs with no homology to known human genes in the NCBI database are used to clone unknown genes by any technique known in the art.

In a preferred embodiment, genomic DNA is isolated from the two-step selected library-transduced cells and used as a template for PCR, using vector-derived sequences flanking the inserts as primers. The PCR-amplified mixture of inserts from the selected cells is recloned into a vector. In further preferred embodiments, the vector is a TA cloning vector from Invitrogen Life Technologies that facilitates direct cloning of PCR products. Plasmid clones from the library of selected fragments are sequenced by high-throughput DNA sequencing using vector-derived sequences flanking the inserts as primers. The sequences of growth-inhibitory GSEs are used as query for the BLAST homology search in the NCBI nr database to identify genes that gave rise to the selected GSE fragments.

In cases where no match can be found in the database, a pair of oppositely directed primers is designed according to the GSE sequence. cDNAs from the same human cell lines where the normalized GSE library is derived is used as template. Rapid Amplification of cDNA Ends (RACE) is performed using technique known in the art to capture the missing parts of the cDNA (Frohman et al., 1988, *Proc. Natl. Acad. Sci. USA* 85: 8998–9002; also see U.S. Pat. Nos. 5,578,467, and 5,334,515, incorporated by reference). Full-length cDNA of the unknown gene can be obtained by assembling the RACE products with the GSE clone. In a preferred embodiment, the GSE is used to BLAST search the NCBI human EST database. The longest corresponding EST is obtained from the I.M.A.G.E. Consortium (distributed by American Type Culture Collection or Research Genetics) and sequence verified. ORF Finder from NCBI is used to identify putative open reading frame from the GSE, which helps to determine if the cDNA fragment lacks the 3' or/and the 5' portion. The RACE primers are designed according to the extended cDNA sequence based on the EST sequence to amplify the end segments.

Alternatively, a GSE with no homology to known human genes in the NCBI database is PCR-amplified using primers derived from the end sequences of said GSE. The PCR product is then used as probe to screen a cDNA library constructed from the same human cell lines where the GSE library is derived. Positive clones that hybridize to said probe are sequenced to identify putative open reading frame. In cases where the cDNA is not full-length, RACE experiment is performed as described hereinabove.

The invention provides methods for measuring gene expression or activity of the gene products corresponding to GSEs identified using GSE libraries and negative growth selection methods of the invention. In the practice of this aspect of the methods of the invention, gene expression or gene product activity is assayed in cells in the presence or absence of a compound to determine whether the compound inhibits expression or activity of such a gene or gene product. In preferred embodiments, gene expression is assayed using any technique known in the art, such as comparison of northern blot hybridization to cellular mRNA using a detectably-labeled probe (as disclosed, for example, in Sambrook et al., 2001, MOLECULAR CLONING: A LABORATORY MANUAL, $3^{rd}$ ed., Cold Strong Harbor Laboratory Press: N.Y.), or by in vitro amplification methods, such as quantitative reverse transcription—polymerase chain reaction (RT-PCR) assays as disclosed by Noonan et al. (1990, *Proc. Natl. Acad. Sci. USA* 87: 7160–7164), or by western blotting using antibodies specific for the gene product (Sambrook et al., 2001, Id.). Gene product activity is assayed using assays specific for each gene product, such as immunoassay using antibodies specific for said gene products or biochemical assay of gene product function.

Alternatively, gene expression is assayed using recombinant expression constructs having a promoter from a gene corresponding to GSEs identified using GSE libraries and negative growth selection methods of the invention, wherein the promoter is operably linked to a reporter gene. The reporter gene is then used as a sensitive and convenient indicator of the effects of test compounds on gene expression, and enables compounds that inhibit expression or activity of genes required for cell, preferably tumor cell growth to be easily identified. Host cells for these constructs include any cell expressing the corresponding growth-promoting gene. Reporter genes useful in the practice of this aspect of the invention include but are not limited to firefly luciferase, Renilla luciferase, chloramphenicol acetyltransferase, beta-galactosidase, green fluorescent protein, and alkaline phosphatase.

The invention provides peptides encoded by some of the GSEs of the invention that have been identified using the GSE-negative growth selection methods disclosed herein. Such peptides are presented in Table 5 and in the Sequence Listing as SEQ ID NOS. 229–314. Some of these peptides are derived from proteins that were previously known to play a role in cell proliferation, and others from proteins that were first assigned such a role in the instant inventions. All of the identified peptides, however, are novel inhibitors of tumor cell proliferation. Also provided are related compounds within the understanding of those with skill in the art, such as chemical mimetics, organomimetics or peptidomimetics. As used herein, the terms "mimetic," "peptide mimetic," "peptidomimetic," "organomimetic" and "chemical mimetic" are intended to encompass peptide derivatives, peptide analogues and chemical compounds having an arrangement of atoms is a three-dimensional orientation that is equivalent to that of a peptide encoded by a GSE of the invention. It will be understood that the phrase "equivalent to" as used herein is intended to encompass compounds having substitution of certain atoms or chemical moieties in said peptide with moieties having bond lengths, bond angles and arrangements thereof in the mimetic compound that produce the same or sufficiently similar arrangement or orientation of said atoms and moieties to have the biological function of the peptide GSEs of the invention. In the peptide mimetics of the invention, the three-dimensional arrangement of the chemical constituents is structurally and/or functionally equivalent to the three-dimensional arrangement of the peptide backbone and component amino acid sidechains in the peptide, resulting in such peptido-, organo- and chemical mimetics of the peptides of the invention having substantial biological activity. These terms are used according to the understanding in the art, as illustrated for example by Fauchere, 1986, Adv. Drug Res. 15: 29; Veber & Freidinger, 1985, TINS p.392; and Evans et al., 1987, J. Med. Chem. 30: 1229, incorporated herein by reference.

It is understood that a pharmacophore exists for the biological activity of each peptide GSE of the invention. A pharmacophore is understood in the art as comprising an idealized, three-dimensional definition of the structural requirements for biological activity. Peptido-, organo- and chemical mimetics can be designed to fit each pharmacophore with current computer modeling software (computer aided drug design). Said mimetics are produced by structure-function analysis, based on the positional information from the substituent atoms in the peptide GSEs of the invention.

Peptides as provided by the invention can be advantageously synthesized by any of the chemical synthesis techniques known in the art, particularly solid-phase synthesis techniques, for example, using commercially-available automated peptide synthesizers. The mimetics of the present invention can be synthesized by solid phase or solution phase methods conventionally used for the synthesis of peptides (see, for example, Merrifield, 1963, J. Amer. Chem. Soc. 85: 2149–54; Carpino, 1973, Acc. Chem. Res. 6: 191–98; Birr, 1978, ASPECTS OF THE MERRIFIELD PEPTIDE SYNTHESIS, Springer-Verlag: Heidelberg; THE PEPTIDES: ANALYSIS, SYNTHESIS, BIOLOGY, Vols. 1, 2, 3, 5, (Gross & Meinhofer, eds.), Academic Press: New York, 1979; Stewart et al., 1984, SOLID PHASE PEPTIDE SYNTHESIS, 2nd. ed., Pierce Chem. Co.: Rockford, Ill.; Kent, 1988, Ann. Rev. Biochem. 57: 957–89; and Gregg et al., 1990, Int. J. Peptide Protein Res. 55: 161–214 , which are incorporated herein by reference in their entirety.)

The use of solid phase methodology is preferred. Briefly, an N-protected C-terminal amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods or the like. Cycles of deprotection, neutralization and coupling of successive protected amino acid derivatives are used to link the amino acids from the C-terminus according to the amino acid sequence. For some synthetic peptides, an FMOC strategy using an acid-sensitive resin may be used. Preferred solid supports in this regard are divinylbenzene cross-linked polystyrene resins, which are commercially available in a variety of functionalized forms, including chloromethyl resin, hydroxymethyl resin, paraacetamidomethyl resin, benzhydrylamine (BHA) resin, 4-methylbenzhydrylamine (MBHA) resin, oxime resins, 4-alkoxybenzyl alcohol resin (Wang resin), 4-(2',4'-dimethoxyphenylaminomethyl)-phenoxymethyl resin, 2,4-dimethoxybenzhydryl-amine resin, and 4-(2',4'-dimethoxyphenyl-FMOC-amino-methyl)-phenoxyacetamidonorleucyl-MBHA resin (Rink amide MBHA resin). In addition, acid-sensitive resins also provide C-terminal acids, if desired. A particularly preferred protecting group for alpha amino acids is base-labile 9-fluorenyl-methoxy-carbonyl (FMOC).

Suitable protecting groups for the side chain functionalities of amino acids chemically compatible with BOC (t-butyloxycarbonyl) and FMOC groups are well known in the art. When using FMOC chemistry, the following protected amino acid derivatives are preferred: FMOC-Cys(Trit), FMOC-Ser(But), FMOC-Asn(Trit), FMOC-Leu, FMOC-Thr(Trit), FMOC-Val, FMOC-Gly, FMOC-Lys(Boc), FMOC-Gln(Trit), FMOC-Glu(OBut), FMOC-His(Trit), FMOC-Tyr(But), FMOC-Arg(PMC (2,2,5,7,8-pentamethyl-chroman-6-sulfonyl)), FMOC-Arg(BOC)$_2$, FMOC-Pro, and FMOC-Trp(BOC). The amino acid residues can be coupled by using a variety of coupling agents and chemistries known in the art, such as direct coupling with DIC (diisopropyl-carbodiimide), DCC (dicyclohexylcarbodiimide), BOP (benzotriazolyl-N-oxytrisdimethylaminophosphonium hexa-fluorophosphate), PyBOP (benzotriazole-1-yl-oxy-tris-pyrrolidinophosphonium hexafluoro-phosphate), PyBrOP (bromo-tris-pyrrolidinophosphonium hexafluoro-phosphate); via performed symmetrical anhydrides; via active esters such as pentafluorophenyl esters; or via performed HOBt (1-hydroxybenzotriazole) active esters or by using FMOC-amino acid fluoride and chlorides or by using FMOC-amino acid-N-carboxy anhydrides. Activation with HBTU (2-(1H-benzotriazole-1-yl),1,1,3,3-tetramethyluronium hexafluorophosphate) or HATU (2-(1H-7-aza-benzotriazole-1-yl),1,1,3,3-tetramethyluronium hexafluoro-phosphate) in the presence of HOBt or HOAt (7-azahydroxybenztriazole) is preferred.

The solid phase method can be carried out manually, although automated synthesis on a commercially available peptide synthesizer (e.g., Applied Biosystems 431A or the like; Applied Biosystems, Foster City, Calif.) is preferred. In a typical synthesis, the first (C-terminal) amino acid is loaded on the chlorotrityl resin. Successive deprotection (with 20% piperidine/NMP (N-methylpyrrolidone)) and coupling cycles according to ABI FastMoc protocols (ABI user bulletins 32 and 33, Applied Biosystems are used to build the whole peptide sequence. Double and triple coupling, with capping by acetic anhydride, may also be used.

The synthetic mimetic peptide is cleaved from the resin and deprotected by treatment with TFA (trifluoroacetic acid) containing appropriate scavengers. Many such cleavage reagents, such as Reagent K (0.75 g crystalline phenol, 0.25 mL ethanedithiol, 0.5 mL thioanisole, 0.5 mL deionized water, 10 mL TFA) and others, can be used. The peptide is separated from the resin by filtration and isolated by ether precipitation. Further purification may be achieved by conventional methods, such as gel filtration and reverse phase HPLC (high performance liquid chromatography). Synthetic calcitonin mimetics according to the present invention may be in the form of pharmaceutically acceptable salts, especially base-addition salts including salts of organic bases and inorganic bases. The base-addition salts of the acidic amino acid residues are prepared by treatment of the peptide with the appropriate base or inorganic base, according to procedures well known to those skilled in the art, or the desired salt may be obtained directly by lyophilization out of the appropriate base.

Generally, those skilled in the art will recognize that peptides as described herein may be modified by a variety of chemical techniques to produce compounds having essentially the same activity as the unmodified peptide, and optionally having other desirable properties. For example, carboxylic acid groups of the peptide may be provided in the form of a salt of a pharmaceutically-acceptable cation. Amino groups within the peptide may be in the form of a pharmaceutically-acceptable acid addition salt, such as the HCl, HBr, acetic, benzoic, toluene sulfonic, maleic, tartaric and other organic salts, or may be converted to an amide. Thiols can be protected with any one of a number of well-recognized protecting groups, such as acetamide groups. Those skilled in the art will also recognize methods for introducing cyclic structures into the peptides of this invention so that the native binding configuration will be more nearly approximated. For example, a carboxyl terminal or amino terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Specifically, a variety of techniques are available for constructing peptide derivatives and analogues with the same or similar desired biological activity as the corresponding peptide compound but with more favorable activity than the peptide with respect to solubility, stability, and susceptibility to hydrolysis and proteolysis. Such derivatives and analogues include peptides modified at the N-terminal amino group, the C-terminal carboxyl group, and/or changing one or more of the amido linkages in the peptide to a non-amido linkage. It will be understood that two or more such modifications can be coupled in one peptide mimetic structure (e.g., modification at the C-terminal carboxyl group and inclusion of a —$CH_2$— carbamate linkage between two amino acids in the peptide).

Amino terminus modifications include alkylating, acetylating, adding a carbobenzoyl group, and forming a succinimide group. Specifically, the N-terminal amino group can then be reacted to form an amide group of the formula RC(O)NH— where R is alkyl, preferably lower alkyl, and is added by reaction with an acid halide, RC(O)Cl or acid anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—. Alternatively, the amino terminus can be covalently linked to succinimide group by reaction with succinic anhydride. An approximately equimolar amount or an excess of succinic anhydride (e.g., about 5 equivalents) are used and the terminal amino group is converted to the succinimide by methods well known in the art including the use of an excess (e.g., ten equivalents) of a tertiary amine such as diusopropylethylamine in a suitable inert solvent (e.g., dichloromethane), as described in Wollenberg et al., U.S. Pat. No. 4,612,132, is incorporated herein by reference in its entirety. It will also be understood that the succinic group can be substituted with, for example, $C_2$- through $C_6$-alkyl or —SR substituents, which are prepared in a conventional manner to provide for substituted succinimide at the N-terminus of the peptide. Such alkyl substituents are prepared by reaction of a lower olefin ($C_2$- through $C_6$-alkyl) with maleic anhydride in the manner described by Wollenberg et al., supra., and —SR substituents are prepared by reaction of RSH with maleic anhydride where R is as defined above. In another advantageous embodiments, the amino terminus is derivatized to form a benzyloxycarbonyl-NH— or a substituted benzyloxycarbonyl-NH— group. This derivative is produced by reaction with approximately an equivalent amount or an excess of benzyloxycarbonyl chloride (CBZ-Cl) or a substituted CBZ-Cl in a suitable inert diluent (e.g., dichloromethane) preferably containing a tertiary amine to scavenge the acid generated during the reaction. In yet another derivative, the N-terminus comprises a sulfonamide group by reaction with an equivalent amount or an excess (e.g., 5 equivalents) of R—$S(O)_2$Cl in a suitable inert diluent (dichloromethane) to convert the terminal amine into a sulfonamide, where R is alkyl and preferably lower alkyl. Preferably, the inert diluent contains excess tertiary amine (e.g., ten equivalents) such as diusopropylethylamine, to scavenge the acid generated during reaction. Reaction conditions are otherwise conventional (e.g., room temperature for 30 minutes). Carbamate groups are produced at the amino terminus by reaction with an equivalent amount or an excess (e.g., 5 equivalents) of R—OC(O)Cl or R—OC(O)O$C_6H_4$-p-$NO_2$ in a suitable inert diluent (e.g., dichloromethane) to convert the terminal amine into a carbamate, where R is alkyl, preferably lower alkyl. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes). Urea groups are formed at the amino terminus by reaction with an equivalent amount or an excess (e.g., 5 equivalents) of R—N═C═O in a suitable inert diluent (e.g., dichloromethane) to convert the terminal amine into a urea (i.e., RNHC(O)NH—) group where R is as defined above. preferably, the inert diluent contains an excess (e.g., about 10 equivalents) of a tertiary amine, such as dilsopropylethylamine. Reaction conditions are otherwise conventional (e.g., room temperature for about 30 minutes).

In preparing peptide mimetics wherein the C-terminal carboxyl group is replaced by an ester (e.g., —C(O)OR where R is alkyl and preferably lower alkyl), resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester. In preparing peptide mimetics wherein the C-terminal carboxyl group is replaced by the amide —C(O)NR$_3$R$_4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain Protected peptide from the support yields the free peptide amide and reaction with an alkylamine or a dialkylamine yields a side chain protected alkylamide or dialkylamide (i.e., the C-terminus is —C(O)NRR$_1$, where R and R$_1$ are alkyl and preferably lower alkyl). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by displacement of the —OH or the ester (—OR) of the carboxyl group or ester respectively with the N-terminal amino group to form a cyclic peptide. For example, after synthesis and cleavage to give the peptide acid, the free acid is converted in solution to an activated ester by an appropriate carboxyl group activator such as dicyclohexylcarbodiimide (DCC), for example, in methylene chloride (CH$_2$Cl$_2$), dimethyl formamide (DMF), or mixtures thereof. The cyclic peptide is then formed by displacement of the activated ester with the N-terminal amine. Cyclization, rather than polymerization, can be enhanced by use of very dilute solutions according to methods well known in the art.

Peptide mimetics as understood in the art and provided by the invention are structurally similar to the paradigm peptide encoded by each of the sense-oriented GSEs of the invention, but have one or more peptide linkages optionally replaced by a linkage selected from the group consisting of: —CH$_2$NH—, —CH$_2$S—, —CH$_2$CH$_2$—, —CH=CH— (in both cis and trans conformers), —COCH$_2$—, —CH(OH) CH$_2$—, and —CH$_2$SO—, by methods known in the art and further described in the following references: Spatola,1983, in CHEMISTRY AND BIOCHEMISTRY OF AMINO ACIDS, PEPTIDES, AND PROTEINS, (Weinstein, ed.), Marcel Dekker: New York, p. 267; Spatola, 1983, *Peptide Backbone Modifications* 1: 3; Morley, 1980, *Trends Pharm. Sci*. pp. 463–468; Hudson et al., 1979, *Int. J. Pept. Prot. Res.* 14: 177–185; Spatola et al., 1986, *Life Sci.* 38: 1243–1249; Hann, 1982, *J. Chem. Soc. Perkin Trans*. I 307–314; Almquist et al., 1980, *J. Med. Chem.* 23: 1392–1398; Jennings-White et al., 1982, *Tetrahedron Lett.* 23: 2533; Szelke et al., 1982, European Patent Application, Publication No. EP045665A; Holladay et al., 1983, *Tetrahedron Lett.* 24: 4401–4404; and Hruby, 1982, *Life Sci.* 31: 189–199, each of which is incorporated herein by reference. Such peptide mimetics may have significant advantages over polypeptide embodiments, including, for example: being more economical to produce, having greater chemical stability or enhanced pharmacological properties (such half-life, absorption, potency, efficacy, etc.), reduced antigenicity, and other properties.

Mimetic analogs of the tumor-inhibiting peptides of the invention may also be obtained using the principles of conventional or rational drug design (see, Andrews et al., 1990, *Proc. Alfred Benzon Symp.* 28: 145–165; McPherson, 1990, *Eur. J. Biochem.* 189:1–24; Hol et al., 1989a, in MOLECULAR RECOGNITION: CHEMICAL AND BIOCHEMICAL PROBLEMS, (Roberts, ed.); Royal Society of Chemistry; pp. 84–93; Hol, 1989b, *Arzneim-Forsch.* 39:1016–1018; Hol, 1986, *Agnew Chem. Int. Ed. Engl.* 25: 767–778, the disclosures of which are herein incorporated by reference).

In accordance with the methods of conventional drug design, the desired mimetic molecules are obtained by randomly testing molecules whose structures have an attribute in common with the structure of a "native" peptide. The quantitative contribution that results from a change in a particular group of a binding molecule can be determined by measuring the biological activity of the putative mimetic in comparison with the tumor-inhibiting activity of the peptide. In a preferred embodiment of rational drug design, the mimetic is designed to share an attribuite of the most stable three-dimensional conformation of the peptide. Thus, for example, the mimetic may be designed to possess chemical groups that are oriented in a way sufficient to cause ionic, hydrophobic, or van der Waals interactions that are similar to those exhibited by the tumor-inhibiting peptides of the invention, as disclosed herein.

The preferred method for performing rational mimetic design employs a computer system capable of forming a representation of the three-dimensional structure of the peptide, such as those exemplified by Hol, 1989a, ibid.; Hol, 1989b, ibid.; and Hol, 1986, ibid. Molecular structures of the peptido-, organo- and chemical mimetics of the peptides of the invention are produced according to those with skill in the art using computer-assisted design programs commercially available in the art. Examples of such programs include SYBYL 6.5®, HQSAR™, and ALCHEMY 2000™ (Tripos); GALAXY™ and AM2000™ (AM Technologies, Inc., San Antonio, Tex.); CATALYST™ and CERIUS™ (Molecular Simulations, Inc., San Diego, Calif.); CACHE PRODUCTS™, TSAR™, AMBER™, and CHEM-X™ (Oxford Molecular Products, Oxford, Calif.)and CHEMBUILDER3D™ (Interactive Simulations, Inc., San Diego, Calif.).

The peptido-, organo- and chemical mimetics produced using the peptides disclosed herein using, for example, art-recognized molecular modeling programs are produced using conventional chemical synthetic techniques, most preferably designed to accommodate high throughput screening, including combinatorial chemistry methods. Combinatorial methods useful in the production of the peptido-, organo- and chemical mimetics of the invention include phage display arrays, solid-phase synthesis and combinatorial chemistry arrays, as provided, for example, by SIDDCO, Tuscon, Ariz.; Tripos, Inc.; Calbiochem/Novabiochem, San Diego, Calif.; Symyx Technologies, Inc., Santa Clara, Calif.; Medichem Research, Inc., Lemont, Ill.; Pharm-Eco Laboratories, Inc., Bethlehem, Pa.; or N.V. Organon, Oss, Netherlands. Combinatorial chemistry production of the peptido-, organo- and chemical mimetics of the invention are produced according to methods known in the art, including but not limited to techniques disclosed in Terrett, 1998, COMBINATORIAL CHEMISTRY, Oxford University Press, London; Gallop et al., 1994, "Applications of combinatorial technologies to drug discovery. 1. Background and peptide combinatorial libraries," *J. Med. Chem.* 37: 1233–51; Gordon et al., 1994, "Applications of combinatorial technologies to drug discovery. 2. Combinatorial organic synthesis, library screening strategies, and future directions," *J. Med. Chem.* 37: 1385–1401; Look et al., 1996, *Bioorg. Med. Chem. Lett.* 6: 707–12; Ruhland et al., 1996, *J. Amer. Chem. Soc.* 118: 253–4; Gordon et al., 1996, *Acc.Chem. Res.* 29: 144–54; Thompson & Ellman, 1996, Chem. Rev. 96: 555–600; Fruchtel & Jung, 1996, *Angew. Chem. Int. Ed. Engl.* 35: 17–42; Pavia, 1995, "The Chemical Generation of Molecular Diversity", Network Science Center, www.netsci.org; Adnan et al., 1995, "Solid Support Combinatorial Chemistry in Lead Discovery and SAR Optimization," Id., Davies and Briant, 1995, "Combinatorial Chemistry Library Design using Pharmacophore Diversity," Id., Pavia, 1996, "Chemically Generated Screening Libraries: Present and Future," Id.; and U.S. Pat. Nos. 5,880,972 to Horlbeck; 5,463,564 to Agrafiotis et al.; 5,331573 to Balaji et al.; and 5,573,905 to Lerner et al.

The invention also provides methods for using the genes identified herein (particularly the genes set forth in Table 3) to screen compounds to identify inhibitors of expression or activity of said genes. In the practice of this aspect of the methods of the invention, cells expressing a gene required for cell growth, particularly a gene identified in Table 3, are assayed in the presence and absence of a test compound, and test compounds that reduce expression or activity of the gene or gene product identified thereby. Additionally, the assays can be performed under suicide selection conditions, wherein compounds that inhibit cell growth by inhibiting expression or activity of the gene select for survival of the cells. In alternative embodiments, reporter gene constructs of the invention are used, wherein expression of the reporter gene is reduced in the presence but not the absence of the test compound.

The methods of the invention are useful for identifying compounds that inhibit the growth of tumor cells, most preferably human tumor cells. The invention also provides the identified compounds and methods for using the identified compounds to inhibit tumor cell, most preferably human tumor cell growth. Exemplary compounds include neutralizing antibodies that interfere with gene product activity; antisense oligonucleotides, developed either as GSEs according to the methods of the invention or identified by other methods known in the art; ribozymes; triple-helix oligonucleotides; and "small molecule" inhibitors of gene expression or activity, preferably said small molecules that specifically bind to the gene product or to regulatory elements responsible for mediating expression of a gene in Table 3. It is recognized by one skilled in the art that a gene of the present invention can be used to identify biological pathways that contain the protein encoded by such. Any member of such pathways may be used to identify compounds that inhibit the growth of tumor cells.

The invention also provides embodiments of the compounds identified by the methods disclosed herein as pharmaceutical compositions. The pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries that facilitate processing of the active compounds into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—$CH_3$ where n is 0–4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

For injection, tumor cell growth-inhibiting compounds identified according to the methods of the invention can be formulated in appropriate aqueous solutions, such as physiologically compatible buffers such as Hank's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity. Additionally, the compounds can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the compounds for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compounds of the invention can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0–4, and the like. Salts tend to be more soluble in aqueous or other protonic solvents that are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical compositions of the compounds of the present invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the compound in a local rather than systemic manner, for example, via injection of the compound directly into a specific tissue, often in a depot or sustained release formulation.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, ie., the concentration of the test compound which achieves a half-maximal inhibition of bacterial cell growth. Such information can be used to more accurately determine useful doses in humans.

It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician.

Preferred compounds of the invention will have certain pharmacological properties. Such properties include, but are not limited to oral bioavailability, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcová et al. (1996, *J. Chromat. B* 677: 1–27). Compound half-life is inversely proportional to the frequency of dosage of a compound. In vitro half-lives of compounds may be predicted from assays of microsomal half-life as described by Kuhnz and Gieschen (1998, DRUG METABOLISM AND DISPOSITION, Vol. 26, pp. 1120–1127).

Toxicity and therapeutic efficacy of such compounds can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch.1, p.1).

Dosage amount and interval can be adjusted individually to provide plasma levels of the active moiety that are sufficient to maintain tumor cell growth-inhibitory effects. Usual patient dosages for systemic administration range from 100–2000 mg/day. Stated in terms of patient body surface areas, usual dosages range from 50–910 mg/m²/day. Usual average plasma levels should be maintained within 0.1–1000 µM. In cases of local administration or selective uptake, the effective local concentration of the compound cannot be related to plasma concentration.

The following Examples are intended to further illustrate certain preferred embodiments of the invention and are not limiting in nature.

EXAMPLES

1. Production of Normalized Tumor Library from MCF-7 Human Breast Cancer Cells

A normalized cDNA fragment library was generated from MCF-7 breast carcinoma cell line (estrogen receptor positive, wild-type for p53; ATCC Accession No. HTB22, American Type Culture Collection, Manassas, Va.). Poly (A)+RNA from MCF-7 cells was used to prepare a population of normalized cDNA fragments through a modification of the procedure described in Gudkov and Roninson (1997). Briefly, RNA was fragmented by heating at 100° C. for 9 minutes. Double-stranded cDNA was generated from this heat-fragmented RNA using the Gibco Superscript kit with a reverse-transcription primer (5'-GGATCCTCACT-CACTCANNNNNNNN-3'; SEQ ID NO. 1). This primer contains a random octamer sequence at its 3' end for random priming, and it carries a tag (termed "stop adaptor" in its double-stranded form) that provides TGA stop codons in all three open reading frames, together with BamHI restriction site. PCR assays were used to establish the presence of β2-microglobulin, β-actin and estrogen receptor mRNA sequences in this cDNA preparation. Double-stranded cDNA fragments were ligated to the following adaptor:

(SEQ ID NO.2)
5'GTACCTGAGTTATAGGATCCCT*GCC*ATG*CC*ATG*CC*ATG3'

(SEQ ID NO.3)
3'CCTAGGGAC*GG*TAC*GG*TAC*GG*TAC5'

The latter adaptor ("start adaptor") contains translation start sites in all three frames, together with a BamHI site. The double-stranded cDNA was amplified by PCR with primers that anneal to the start and stop adaptors. Although the start adaptor is initially ligated at both ends of cDNA fragments, the PCR products were generated predominantly by the two different primers and contain the start adaptor only at the 5' but not at 3' end. This desirable outcome is explained by the "PCR suppression effect", due to PCR inhibition by pan-handle-like structures formed upon renaturation of sequences flanked by an inverted repeat (Siebert et al., 1995, *Nucleic Acids Res.* 23: 1087–1088). Furthermore, any residual start adaptors at the 3' ends were subsequently removed by BamHI digestion prior to cloning. The amplified cDNA fragment population was again tested for the presence of β2-microglobulin, β-actin and estrogen receptor sequences. This procedure produced a population of randomly initiating and terminating double-stranded cDNA fragments (100–400 bp size), which are tagged by different adaptors at the ends corresponding to the 5' and 3' direction of the original mRNA. The 5' adaptor contains translation initiation codons in three open reading frames, and the 3' adaptor contains stop codons in all three reading frames. Such fragments direct the synthesis of peptides derived from the parental protein when cloned in sense orientation, or give rise to antisense RNA molecules when cloned in antisense orientation.

The cDNA fragment mixture was subjected to normalization, through a modification of the procedure of Patanjali et al. (1991, *Proc. Natl. Acad. Sci. USA* 88: 1943–1947), based on $C_o t$ fractionation. Normalization was achieved by reannealing portions of denatured cDNA for 24, 48, 72, or 96 hours. Single-stranded products were separated from re-annealed double stranded DNA by hydroxyapatite chromatography. Normalization of cDNA fragments was tested by Southern hybridization with probes corresponding to genes expressed to different levels in MCF-7 cells and performed with each single-stranded fraction. This analysis indicated that the content of β-actin, an abundant mRNA species, decreased over normalization time, with the lowest content found at the 96 hr time point. Conversely, a moderately-abundant cDNA sequence, c-MYC and a low-abundant cDNA sequence, MDR1 (which was undetectable in MCF-7 cDNA prior to normalization) increased their levels to those comparable with β-actin by 96 hr, suggesting that the 96 hr fraction was the best-normalized. To confirm the normalization of the 96 hr fraction, this DNA was digested (on a small scale) with BamHI, ligated into a plasmid vector and transformed into *E. coli* (Top10) by electroporation. Colony hybridization analysis was performed on nitrocellulose filters to which 10,000 colonies were plated, using radiolabeled probes for different genes. The following signal numbers per filter were obtained: β-actin, 3 signals; MDR1, 3 signals; C-MYC, 2 signals; C-FOS, 2 signals. These results indicated that the sequences from the tested genes are found on average in 1 of 3,000–5,000 clones of this library, and also confirmed that the 96 hr fraction was normalized.

The normalized cDNA fraction was amplified by PCR and ligated into IPTG-inducible retroviral vector LNXCO3 (Chang and Roninson, 1996, *Gene* 183: 137–142). The ligation produced a library of approximately 50 million clones. Percent recombination in this library was assessed by PCR of the DNA from bacterial colonies, using primers that flank the insertion site of LNXCO3. The number of clones containing an insert was 131/150 or 87%. Most of the inserts ranged in size from 100 to 300 bp. For further characterization of the library, a fraction of the inserts were recloned into the pcDNA3 vector. The insert sequences of 69 randomly picked clones in pcDNA3 were determined using a high-throughput DNA sequencer, and analyzed for homology to known gene sequences in the public-domain database. Fifty-two of the inserts matched no known genes, 16 corresponded to different human genes, and one sequence was found to be of bacterial origin. This normalized MCF-7 cDNA fragment library was used to select growth-inhibitory GSEs in breast carcinoma cells.

2. Production of Breast Cancer Recipient Cells

The normalized tumor library described in Example 1 was prepared from MCF-7 human breast carcinoma cells. As recipient cells for GSE selection, a different breast carcinoma cell line, MDA-MB-231 (ATCC Accession No. HTB26) was chosen. This line represents a more malignant class of breast cancers relative to MCF-7: it is estrogen receptor-negative and p53-deficient. The choice of different cell lines as the source of RNA and as the recipient was aimed at isolating growth-inhibitory GSEs that are more likely to be effective against different types of breast cancer.

MDA-MB231 cells were first rendered susceptible to infection with ecotropic retroviruses, which can be readily generated at a high titer using convenient packaging cell lines, and are not infectious to humans or unmodified human cells. MDA-MB-231 cells were infected with amphotropic recombinant virus that carries the gene for the murine ecotropic receptor in retroviral vector LXIHis (Levenson et al., 1998, *Hum. Gene Ther.* 9: 1233–1236), and the infected cell population was selected with histidinol. The susceptibility of the selected cells to infection with ecotropic retroviruses was determined by infecting such cells with an ecotropic retrovirus LXSE (Kandel et al., 1997, Id.) that carries the gene for the Green Fluorescent Protein (GFP). Over 86% of LXSE-infected cells were positive for GFP fluorescence (as determined by flow cytometry), indicating a correspondingly high infection rate. These cells were next transfected with the 3'SS plasmid (Stratagene) that carries the LacI repressor (Fieck et al., 1992, *Nucleic Acids Res.* 20: 1785–1791) and the hygromycin resistance marker, and stable transfectants were selected with hygromycin. The selected transfectants were subcloned, and 33 single-cell clones were individually tested for IPTG-regulated expression of a LacI-inhibited promoter. This testing was carried out by transient transfection of the cell clones with pCMVI3luc plasmid (Stratagene) that expresses luciferase from the LacI-regulated CMV promoter. As a positive control, the same assay was carried out on a previously characterized well-regulated fibrosarcoma cell line HT1080 3'SS6 (Chang and Roninson, 1996, Id.; Chang et al., 1999, Id.). Three of the tested clones showed the induction of luciferase expression in the presence of IPTG at a level similar to that of HT1080 3'SS6.

These clones were further tested by the following assays. The first assay was infection with LXSE ecotropic retrovirus, followed by FACS analysis of GFP fluorescence, to determine the susceptibility to ecotropic infection. The second assay was ecotropic retroviral transduction with IPTG-regulated retrovirus LNLucCO3 (Chang and Roninson, 1996), followed by G418 selection and testing for IPTG inducibility of luciferase expression. The third assay was the infection with IPTG-regulated ecotropic retrovirus LNp21CO3 (Chang et al., 1999, Id.), which carries the cell cycle inhibitor p21 (a positive control for an IPTG-inducible genetic inhibitor), followed by BrdU suicide selection (described below) in the presence and in the absence of IPTG. Based on the results of these assays, a cell line called MDA-MB231 3'SS31 was selected as being optimal for growth-inhibitory GSE selection. This cell line showed about 80% infectability with ecotropic retroviruses, approximately 10-fold inducibility by IPTG (which is higher than the concurrently determined value for HT1080 3'SS6) and over 20-fold increase in clonogenic survival of BrdU suicide upon infection with LNp21CO3.

3. Isolation of Tumor Cell Growth Inhibiting Genetic Suppressor Elements

Figure 4:
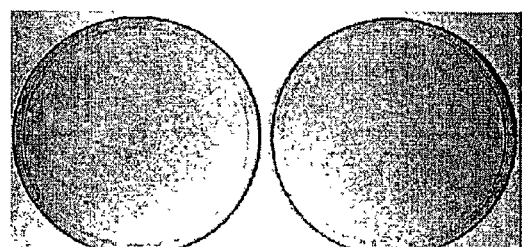
FIG. 4 is a photograph of cell culture plates containing library-transduced cells subjected to BrdU suicide selection in the presence or in the absence of IPTG, immediately after G418 selection (top), after one round of BrdU suicide selection in the presence of IPTG (middle), or after two rounds of BrdU suicide selection in the presence of IPTG (bottom).
Figure 4:
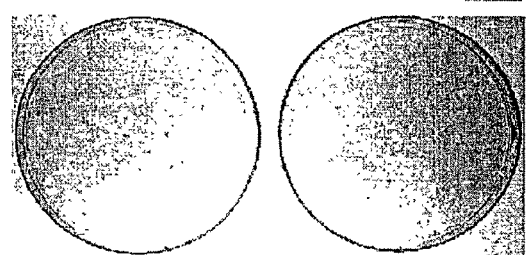
Figure 4:
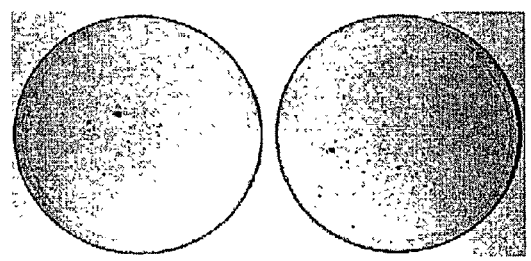

The MCF-7 derived normalized tumor library in the LNXCO3 vector was transduced into MDA-MB231 3'SS31 cell line by ecotropic retroviral transduction using the BOSC23 packaging cell line (Pear et al., 1993, Id.), as described in Roninson et al. (1998, *Methods Enzymol.* 292: 225–248). Two hundred million ($2 \times 10^8$) recipient cells were infected and selected with G418. The infection rate (as determined by the frequency of G418-resistant colonies) was 36%. Eighty million ($8 \times 10^7$) G418-selected infectants were subjected to selection for IPTG-dependent resistance to BrdU suicide, as follows. Cells were plated at $10^6$ cells per P150 and treated with 50 μM IPTG for 36 hrs, then with 50 μM IPTG and 50 μM BrdU for 48 hrs. Cells were thereafter incubated with 10 μM Hoechst 33342 for 3 hrs and illuminated with fluorescent white light for 15 min on a light box, to destroy the cells that grew and incorporated BrdU in the presence of IPTG. Cells were then washed twice with phosphate-buffered saline and allowed to recover in G418-containing medium without IPTG or BrdU for 7–10 days. The surviving cells were then subjected to a second step of BrdU selection under the same conditions. Control plates were selected in the absence of IPTG, and representative plates were stained to count the colonies; these results are shown in FIG. 4. The number of surviving colonies after the second step of selection in the presence of IPTG was approximately three times higher than the corresponding number in the absence of IPTG. In contrast, control cells infected with an insert-free LNXCO3 vector showed no difference in BrdU survival in the presence or in the absence of IPTG. As a positive control, cells were infected with p21-expressing LNp21CO3, but the number of survivors in the presence of IPTG was too high to count. These results demonstrated that the frequency of library-infected cells that survived BrdU suicide selection increased in IPTG-dependent manner, consistent with successful selection of IPTG-inducible growth-inhibitory GSEs.

Genomic DNA was isolated from the two-step selected library-transduced cells and used as a template for PCR, using vector-derived sequences flanking the inserts as primers. The PCR-amplified mixture of inserts from the selected cells was recloned into LNXCO3 vector and close to 3,000 randomly picked plasmid clones from the library of selected fragments were sequenced by high-throughput DNA sequencing by PPD Discovery, Inc., Menlo Park, Calif. 1482 clones containing human cDNA fragments were identified among these sequences by BLAST homology search using the NCBI database and analyzed to identify genes that gave rise to the selected cDNA fragments. Ninety-three genes were found to give rise to two or more of the sequenced clones, indicating the enrichment for such genes in the selected library, with 67 genes represented by three or more clones. Forty-nine of the enriched genes were represented by two or more non-identical sequences. The sequences of the enriched clones are provided in Table 4 and the Sequence Listing. Many of these clones encode peptides derived from the corresponding gene products. The sequences of these growth-inhibitory peptides are provided in Table 5 and in the Sequence Listing as SEQ ID NOS. 229–314. The enriched genes with the corresponding accession numbers, as well as the numbers of selected clones and different sequences derived from each genes are listed in Table 1. Table 2 lists enriched genes previously known to be involved in cell proliferation, and Table 3 lists enriched genes that were not previously known to be involved in cell proliferation.

The following criteria were used for assigning genes to Table 2 or Table 3. The function of each gene was first confirmed according to the corresponding entry in the LocusLink database of NCBI. On the basis of this information, genes that are essential for basic cell functions (such as general transcription or translation), and genes known to play a role in cell cycle progression or carcinogenesis were excluded from Table 3 and assigned to Table 2. The functions of the other genes were then investigated through a database search of the art, using all the common names of the gene listed in LocusLink as keywords for the search. Through this analysis, additional genes were assigned to Table 2 by the following criteria (i) if overexpression of the gene, alone or in combinations, was shown to promote neoplastic transformation or cell immortalization; (ii) if inhibition of the gene function or expression was shown to produce cell growth inhibition or cell death; (iii) if homozygous knockout of the gene was shown to be embryonic lethal in mammals; or (iv) if the gene was found to be activated through genetic changes (such as gene amplification, rearrangement or point mutations) in a substantive fraction of any type of cancers. Genes that did not satisfy any of the above criteria were then assigned to Table 3.

4. Analysis of Tumor Cell Growth Inhibiting Genetic Suppressor Elements

Figure 5:
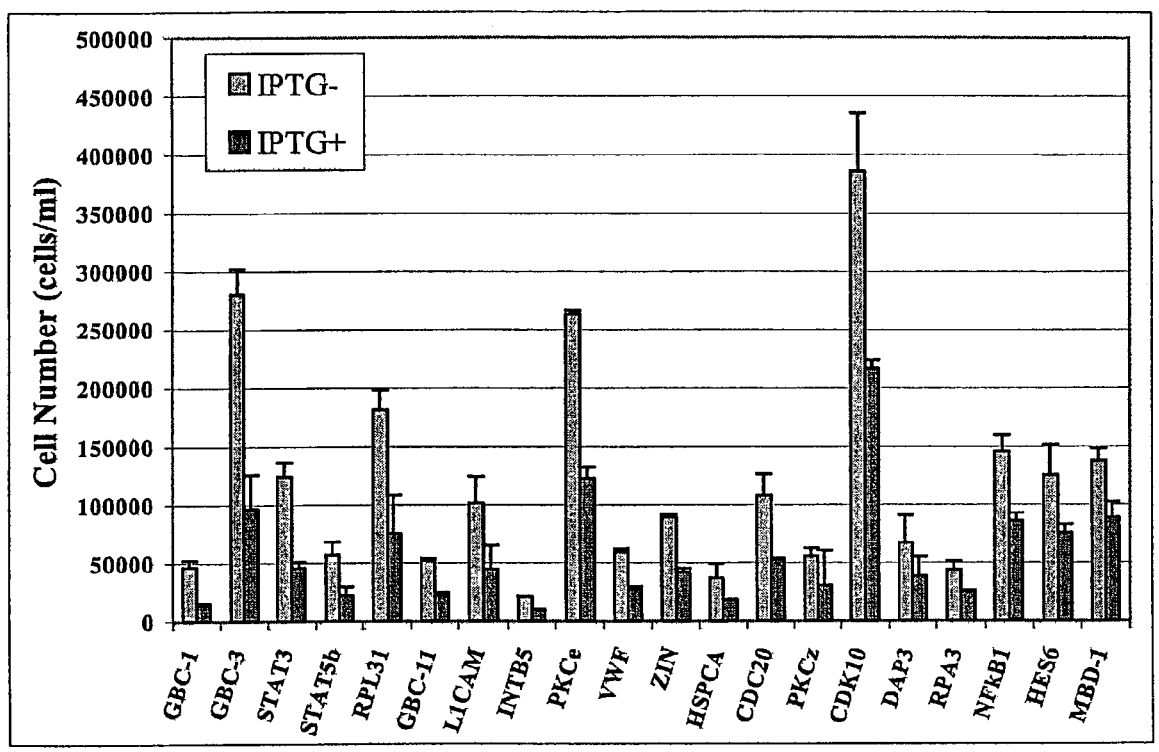
FIG. 5 is a bar diagram of the results of testing of cell populations transduced with individual GSEs for IPTG-dependent resistance to BrdU suicide, measured in triplicates and expressed as mean and standard deviation of the numbers of colonies surviving BrdU suicide selection in the presence and in the absence of IPTG. Sequences for the shown results are GSE (SEQ ID NO): GBC-1 (79), GBC-3 (94), STAT3 (205), STAT5b (211), PRL31 (192), GBC-11 (85), L1CAM (125), INTB5 (112), OKCeta (170), VWF (225), ZIN (228), HSPCA (103), CDC20 (37), PKC zeta (172), CDK10 (39), DAP3 (59), RPA3 (190), NFkB1 (157), HES6 (99), and MBD1 (142).

Individual selected clones representative of enriched genes have been analyzed by functional testing for GSE activity. Results of these assays are summarized in Table 1. The principal assay involves the transduction of individual putative GSE clones (in the LNXCO3 vector) into MDA-MB-231-3'SS31 cells, followed by G418 selection of infected populations (for the neo gene of LNXCO3) and testing the transduced populations for IPTG-dependent survival of BrdU suicide. The latter assay was carried out as follows. Infected cells (200,000 per P100, in triplicate) were treated with 50 µM IPTG for 72 hrs, then with 50 µM IPTG and 50 µM BrdU for 48 hrs. A parallel set of cells was treated in the same way but without IPTG (in triplicate). Cells were then illuminated with white light and allowed to recover in the absence of BrdU and IPTG for 12–14 days. Results are expressed as the average number of colonies per P100, with standard deviations. In each set of assays, insert-free LNXCO3 vector was used as a negative control. As a positive control, LNXCO3 vector expressing CDK inhibitor p21 was used, but this control consistently gave excessively positive values of surviving colonies. Alternative positive controls comprised a GSE derived from a proliferation-associated transcription factor Stat3, which produced moderate but reproducibly positive results in multiple assays. Table 1 lists the results of this assay (IPTG-dependent survival of BrdU suicide) as positive ("A" in Functional Assays column) if t-test analysis of the difference in the number of colonies surviving in the presence and in the absence of IPTG provides a significance value of P<0.05. Results of this analysis on a subset of positive GSEs are shown in FIG. 5.

Figure 6:
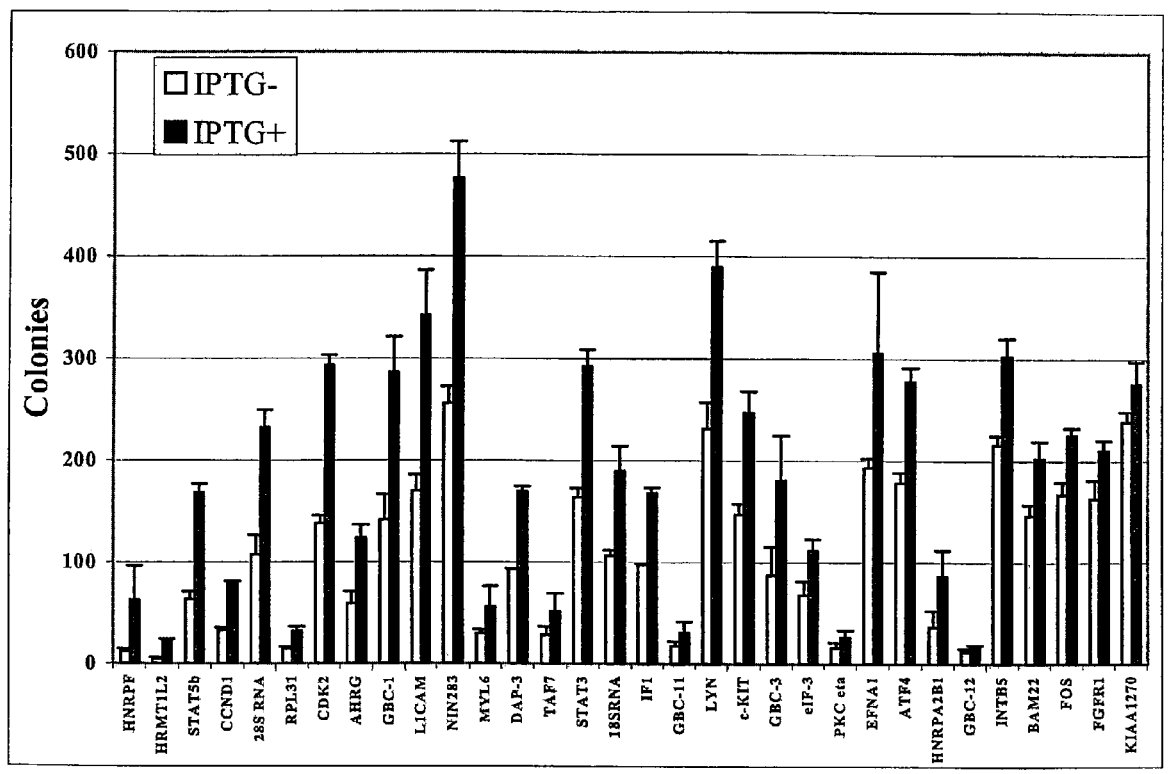
FIG. 6 is a bar diagram of the results of IPTG growth inhibition assays carried out with clonal cell lines transduced with individual GSEs, measured in triplicates and expressed as mean and standard deviation of the cell numbers after 7 days of culture in the presence and in the absence of IPTG. Sequences for the shown results are GSE (SEQ ID NO): HNRPF (101), HRMT1L2 (102), STAT5b (211), CCND1 (57), 28S RNA (17), RPL31 (192), CDK2 (40), AHRG (183), GBC-1 (79), L1CAM (125), NIN283 (158), MYL6 (155), DAP3 (59), TAF7 (215), STAT3 (205), IF1 (32), GBC-11 (85), LYN (138), c-KIT (48), GBC-3 (94), eIF-3 (62), PKCeta (170), EFNA1 (67), ATF4 (27), HNRPA2B1 (102), GBC-12(86), INTB5 (112), BAM22 (35), FOS (43), FGFR1 (77), and KIAA1270 (123).

The assay for IPTG-dependent survival of BrdU suicide was performed for GSEs derived from 38 genes with positive results. Several infected cell populations that scored positive in this assay were also tested by a more stringent assay for direct growth inhibition by IPTG. None of the tested populations, however, showed significant growth inhibition by IPTG. A similar result (positivity in BrdU selection but not in the growth inhibition assay) was reported by Pestov et al. (1998, Id.) for a weak growth-inhibitory cDNA clone encoding a ubiquitin-conjugation enzyme. To determine whether increased BrdU survival in such cell populations reflects the heterogeneity of GSE expression and function among the infected cells, multiple (10 or more) clonal cell lines were generated from a subset of infected populations and tested for the ability to be growth-inhibited by IPTG. Through this process, IPTG-inhibited cell lines containing GSEs from 19 of the enriched genes were produced. The genes that scored positive by this assay are indicated in Table 1 ("B" in Functional Assays column). In contrast to these GSE-containing cell lines, cells transduced with an insert-free LNXCO3 vector showed no growth inhibition in the presence of IPTG. Results of IPTG growth inhibition assays with positive cell lines are shown in FIG. 6.

Putative GSEs from 7 of the tested genes gave a greatly diminished yield of G418-resistant infectants, relative to cells infected with the control LNXCO3 virus or with other tested clones. When the resulting small populations of G418-resistant cells infected with these clones were expanded and tested for IPTG-dependent survival of BrdU suicide, almost all of these populations produced negative results. Remarkably, most of the genes in this category ("C" in Functional Assays column of Table 1) are known to be important positive regulators of cell growth (JUN B, INT-2, MCM-3 replication protein, delta and eta isoforms of protein kinase C) and therefore are expected to give rise to growth-inhibitory GSEs. Since LNXCO3 vector is known to provide substantial basal expression in the absence of IPTG (Chang and Roninson, 1996), it seems likely that this group may include the strongest functional GSEs, which inhibit cell growth even in the absence of IPTG. Altogether, GSEs from a total of 51 genes have so far been confirmed by functional assays (IPTG-dependent survival of BrdU suicide or IPTG-dependent growth inhibition) or a putative positive criterion (decreased apparent infection rate).

The genes shown in Table 2 are known to be positive regulators of the cell growth or neoplastic transformation. These include genes directly involved in cell cycle progression (such as CCN D1 and CDK2) or DNA replication (e.g. PCNA, RPA3 or MCM-3), growth factors (e.g. INT-2/FGF-3 and TDGF1) and growth factor receptors (e.g. FGFR1, C-KIT), transcription factors known to be positive regulators of cell proliferation (e.g. STAT3, c-FOS, NF☐B-

1), several proliferation-associated signal transduction proteins, such as three isoforms of PKC (the primary target of tumor promoters) and three integrin proteins, as well as several ribosomal components required for protein synthesis. The enriched genes include many known protooncogenes, such as JunB and c-FOS (which gave rise to two of three growth-inhibitory GSEs isolated by Pestov and Lau (1994, Id.) from a 19-gene library in NIH 3T3 cells), a FOS-related gene, INT-2, c-KIT, LYN B (YES protooncogene), MET, RAN (a member of RAS family), several growth-promoting genes that are known to be amplified in cancers (CCN D1, CDK2, FGFR1), and several genes reported to be overexpressed in cancers. Some of the enriched genes have specific associations with breast cancer, including INT-2, originally identified as a mammary oncogene (Peters et al., 1984, *Nature* 309: 273–275), CCN D1 and FGFR1 found to be amplified in a substantial minority of breast cancers (Barnes and Gillett, 1998, Breast Cancer Res Treat. 52: 1–15; Jacquemier et al., 1994, *Int. J. Cancer* 59: 373–378), and HSPCA, which was shown to be expressed in all the tested breast cancers (143 total) at a higher level than in non-malignant breast tissue (Jameel et al., 1992, *Int. J. Cancer* 50: 409–415). The abundance of such genes among the selected sequences provides strong validation of this approach to the elucidation of positive growth regulators in breast carcinoma cells.

The genes in Table 3 have no known function in growth regulation. These genes encode several transcription factors, proteins involved in signal transduction or cell adhesion, a number of proteins involved in RNA transport or protein trafficking and processing, a group of genes with miscellaneous other functions that are not related to cell growth, and 10 genes, the functions of which are presently unknown.

Of special interest, at least three of the genes in Table 3 appear to be inessential for growth of normal cells, since homozygous knockout of these genes in mice does not prevent the development of adult animals (except for some limited developmental abnormalities). These genes include L1CAM (Dahme et al., 1997, *Nat. Genet.* 17 346–349), ICAM2 (Gerwin et al., 1999, *Immunity* 10: 9–19), and von Willebrand factor (Denis et al., 1998, *Proc Natl Acad Sci USA* 95: 9524–9529). The effect of GSEs derived from these genes on breast carcinoma cells suggests that inhibition of such "inessential" genes may have a desirable tumor-specific or tissue-specific antiproliferative effect.

A striking example of an apparently inessential gene enriched in the selected library, which has been independently identified as a highly promising target for breast cancer treatment, is provided by HSPCA (included in Table 2). The basic function of this gene, which belongs to of a heat shock responsive family of chaperone proteins, which play a role in refolding of mature proteins, does not indicate that it should be required for cell growth. HSPCA, however, was found to play a role in stabilizing several proteins that are involved in oncogenic pathways, including Raf, Met, steroid receptors, and members of the HER kinase family, and to serve as the target of an antitumor antibiotic geldanamycin (Stebbins et al., 1997, *Cell* 89: 239–250). The HSPCA-inhibiting geldanamycin analog 17-AAG has been shown to arrest the growth of breast carcinoma cell lines (including MDA-MB-231; Munster et al, 2001, *Cancer Res.* 61: 2945–2952) and to sensitize such cells to chemotherapy-induced apoptosis (Munster et al., 2001, *Clin Cancer Res* 7: 2228–2236); 17-AAG is currently in clinical trial. The example of HSPCA suggests that other apparently inessential genes identified by GSE selection are likely to provide similarly promising targets for cancer treatment. Some of these potential novel targets are described in more detail in the next section.

5. Potential Novel Drug Targets.

Several of the selected genes warrant consideration as potential novel targets for cancer drug development. Non-limiting examples are as follows.

L1CAM. L1 cell adhesion molecule (L1CAM) is represented in the set of growth-inhibiting GSEs by eight sense-oriented and four antisense-oriented GSEs. L1CAM is a 200–220 kDa type I membrane glycoprotein of the immunoglobulin superfamily expressed in neural, hematopoietic and certain epithelial cells. The non-neuronal (shortened) form of L1CAM is expressed highly in melanoma, neuroblastoma, and other tumor cell types, including breast. L1CAM is found not only in membrane-bound form but also in the extracellular matrix of brain and tumor cells. Soluble L1CAM directs the migration of glioma cells, and one of anti-L1CAM antibodies was found to inhibit this migration (Izumoto et al., 1996, *Cancer Res.* 56: 1440–1444). Such an antibody might be useful as an initial prototype agent to validate L1CAM as a cancer drug target.

Figure 7:
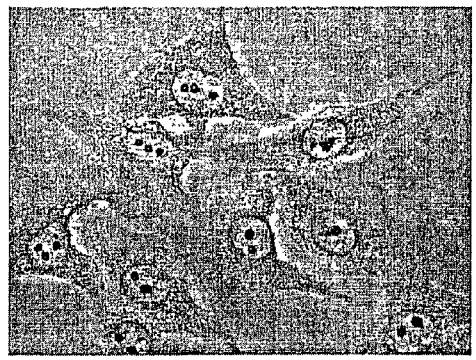
FIGS. 7A and 7B are photomicrographs illustrating the morphological effects of an L1CAM-derived GSE (SEQ ID NO 134) in a clonal IPTG-inhibited cell line.
Figure 7:
Figure 7:
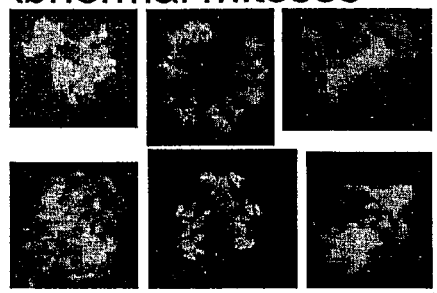
Figure 7:
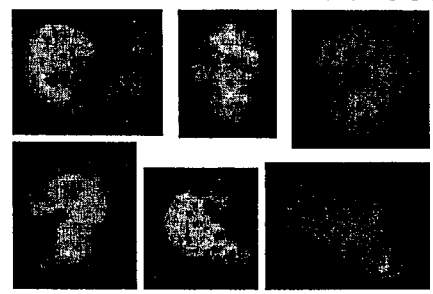

As a cell surface molecule, L1CAM should be easily accessible to different types of drugs. FIGS. 7A and 7B illustrate morphological effects of an L1CAM-derived GSE in a clonal IPTG-inhibited cell line. Four-day treatment with IPTG drastically altered cell morphology, with the cells developing lamellipodia and apparent focal adhesion plaques (FIG. 7A). This effect suggests that the IPTG-induced GSE affects cell adhesion, as would have been expected from targeting L1CAM. GSE induction not only arrested cell growth but also induced mitotic catastrophe in 15–20% of IPTG-treated cells. Mitotic catastrophe is a major form of tumor cell death (Chang et al., 1999, Id.), which is characterized by abnormal mitotic figures and formation of cells with multiple micronuclei (FIG. 7B). The ability of a GSE to induce mitotic catastrophe is a good general indication for the potential promise of a GSE-inhibited target.

Human L1CAM gene is mutated in patients with a severe X-linked neurological syndrome (CRASH: corpus callosum hypoplasia, retardation, aphasia, spastic paraplegia and hydrocephalus). L1CAM "knockout" (−/−) mice develop to adulthood and appear superficially normal (slightly smaller than adults), but they have a shortened lifespan due to CRASH-like neurological deficits, which may be related to a decrease in neurite outgrowth (Dahme et al., 1997, Id.). These observations suggest that targeting L1CAM in an adult cancer patient should not have major toxicity outside of the nervous system, where most drugs will not penetrate due to the blood-brain barrier. Furthermore, it is quite likely that the neurological effects result only from a lack of L1CAM during embryonic development and would not develop from L1CAM inhibition in an adult.

ICAM2. The intercellular cell adhesion molecule-2 (ICAM2) is represented in the set of growth-inhibiting GSEs by two sense-oriented and one antisense-oriented GSE. ICAM2 has many similarities to L1CAM and is also inessential for the growth of normal cells (Gerwin et al., 1999, Id.). Anti-ICAM2 antibodies, for example, are attractive possibilities for prototype drugs.

NIN283. This gene has recently been described (Araki et al., 2001, *J. Biol. Chem.* 276: 34131–34141) as being induced in Schwann cells upon nerve injury and termed NIN283. Induction of NIN283 is a part of injury response of Schwann cells, which then act to promote the growth of the injured nerve. NIN283 is also induced by nerve growth factor (NGF). Like L1CAM, NIN283 is expressed primarily in the brain. It is localized to lysosomes, is highly conserved in evolution (with identifiable homologs in Drosophila and C. elegans), and contains a unique combination of a single zinc finger and a RING finger motif. Based on these structural features and localization, Araki et al. (2001, Id.) speculated that NIN283 may be involved in ubiquitin-mediated protein modification and degradation. With this putative function in protein modification, stress inducibility and evolutionary conservation, NIN283 appears analogous to the above-discussed HSPCA.

Here, this gene was found to give rise to one of the strongest functionally active GSEs in breast carcinoma growth-inhibition assays. The available information on functional domains of NIN283 should be useful in structure-based rational design of small molecule inhibitors of this interesting protein.

A TF4. Activating transcription factor 4 gave rise to the most highly enriched antisense GSE in these selection assays. Homozygous knockout of ATF4 results in only minor developmental abnormalities (in the eye lens; Tanaka et al., 1998, *Genes Cells* 3: 801–810; Hettmann et al., 2000, *Dev. Biol.* 222: 110–123), indicating that this factor is not essential for normal cell growth. The results disclosed herein implicate ATF4 in breast cancer cell proliferation and are strengthened by reports in the art that ATF4 expression and function are augmented by heregulin β1, a factor that stimulates the growth of breast cancer cells (Talukder et al., 2000, *Cancer Res.* 60: 276–281).

Zinedin. Zinedin is a recently described calmodulin-binding protein with a WD repeat domain, which is preferentially expressed in the brain (Castets et al., 2000, *J. Biol. Chem.* 275: 19970–19977). This expression pattern suggests that zinedin-targeting drugs are unlikely to have an effect on any normal proliferating cells. An antisense-oriented GSE derived from zinedin, however, was found herein to inhibit breast carcinoma cell growth, both by the IPTG-dependent BrdU suicide assay and by the ability to give rise to an IPTG-inhibited cell line. Structural analysis of zinedin indicates specific domains that apparently mediate its interactions with calmodulin and caveolin (Castets et al., Id.). Structure-based targeting of these domains, as well as screening based on the interference with zinedin-calmodulin interactions, can be used as strategies for developing zinedin-targeting drugs.

Novel genes. Several genes identified by this selection have no known function, no significant homologies with known genes or identifiable functional domains. These results provide the first functional evidence for such genes. One of the most highly enriched and functionally active GSEs is designated GBC-1 (Growth of Breast Carcinoma 1). Translated protein sequence of GBC-1 matches a partial sense-oriented sequence of a hypothetical unnamed protein (accession No. XP_031920). GBC-1 GSE encodes a helical-repeat peptide. The strong growth-inhibitory activity of this GSE suggests that molecules derived from or mimicking this peptide are likely to have antitumor activity. The GBC-1 peptide disclosed herein can be regarded as a prototype drug, the structure of which can be used to direct rational design of a synthetic compound.

Among other novel genes identified in the instant invention, two genes, designated herein GBC-3 (Growth of Breast Carcinoma 3) and GBC-11 (Growth of Breast Carcinoma 11) are the most highly enriched, and their GSEs show strong functional activity. Cell lines that comprise these GSE and that are efficiently growth-inhibited by treatment with IPTG are useful for characterizing the cellular effects of GBC-3 or GBC-11 inhibition. GBC-3 matches an otherwise uncharacterized EST AA443027 and maps to chromosome 3q29, GBC-11 maps to chromosome 14 and does not match any known cDNA sequences. GBC-3 appears according to "Virtual Northern" analysis carried out using the NCBI SAGE database to be expressed at a very low level in all cell types, suggesting that it may be an easy target to inhibit.

6. In Vivo Testing of Test Compounds

The efficacy of inhibiting expression or activity of the genes set forth in Table 3 is tested in vivo as follows.

Cells ($1-2\times10^6$) expressing an IPTG-inducible GSE of the invention that inhibits expression or activity of a gene in Table 3 are injected into a mouse as a xenograft, most preferably in one flank of the mouse so that tumor growth can be visually monitored. IPTG-regulated gene expression in mouse xenografts of MDA-MB-231 breast carcinoma has been demonstrated in the art, for example by Lee el al. (1997, *Biotechniques* 23: 1062–1068) and the experiments described herein can be performed substantially as described by Lee et al. but using the GSE-containing tumor cells of the invention. Conveniently, GSE-naïve tumor cells are injected in the opposite flank in each mouse. Two sets of injected mice are housed and maintained in parallel, with one set of mice having feed supplemented with IPTG at a concentration as taught by Lee et al. and the other set of mice not receiving IPTG supplemented food. Emergent tumors are observed on the mice under humane animal care conditions until the extent of tumor cell growth is life-threatening or inhumane. Biopsy samples are taken and the tumors measured and weighed after animal sacrifice to determine differences between the GSE-expressing and non-GSE-expressing tumors in each mouse and between mice fed IPTG and mice without IPTG supplementation.

IPTG-fed mice will bear one tumor of naïve xenograft cells whose growth is unaffected by IPTG. These tumors will be substantially identical to the size of both naïve xenograft cell and GSE-containing xenograft cell tumor in mice not fed IPTG. In contrast, the tumor produced from the GSE-containing xenograft cells in mice fed IPTG will be substantially smaller than the other tumors. Biopsy will show proliferating tumor cells in both naïve xenograft cell and GSE-containing xenograft cell tumor in mice not fed IPTG and naïve xenograft cells from IPTG-fed mice, and quiescent or dying cells in the GSE-containing xenograft tumor.

These results demonstrate that inhibition of expression or activity of genes set forth in Table 3 inhibits tumor cell growth in vivo.

It should be understood that the foregoing disclosure emphasizes certain specific embodiments of the invention and that all modifications or alternatives equivalent thereto are within the spirit and scope of the invention as set forth in the appended claims.

TABLE 1

Genes Enriched among 1482 Sequences of Clones Containing cDNA Inserts in the Selected Library

| Gene | Accession # | # Sequences (s/as) | # clones | Functional Assays* |
|---|---|---|---|---|
| ATF4 | NM_001675.1 | 5(as) | 369 | A |
| STAT5b | NM_012448.1 | 4(s), 4(as) | 152 | A, B |
| GBC-1 | NM_031221.1 | 2(s) | 70 | A, B |
| ARHG | NM_001665.1 | 5(s), 1(as) | 43 | A |

TABLE 1-continued

Genes Enriched among 1482 Sequences of Clones Containing cDNA Inserts in the Selected Library

| Gene | Accession # | # Sequences (s/as) | # clones | Functional Assays* |
|---|---|---|---|---|
| VWF | NM_000552.2 | 6(s), 5(as) | 39 | B |
| MCM3 | NM_002388.2 | 3(s), 4(as) | 38 | C |
| 18S RNA | K03432.1 | 8(s), 4(as) | 33 | A |
| ITGB5 | NM_002213.1 | 4(s), 1(as) | 30 | A, B |
| HSPCA | NM_005348.1 | 2(s) | 27 | B |
| STAT3 | NM_003150.1 | 4(s), 3(as) | 25 | A, B |
| L1CAM | NM_000425.2 | 8(s), 4(as) | 20 | A, B |
| 28S RNA | M27830.1 | 3(s) | 17 | A |
| C-FOS | NM_005252.2 | 3(s), 3(as) | 17 | A |
| C-KIT | NM_021099.2 | 4(s), 2(as) | 12 | A |
| FEN1 | NM_004111.3 | 2(s), 2(as) | 12 | A |
| GBC-3 | AA443027 | 1(s) | 12 | A, B |
| NIN283 | NM_032268 | 1(s) | 11 | A |
| ADPRT | NM_001618 | 1(s), 1(as) | 10 | |
| CCN D1 | NM_001758.1 | 2(s), 2(as) | 9 | A |
| CDC20 | NM_001255 | 1(as) | 9 | B |
| EFNA1 | NM_004428 | 1(s), 3(as) | 9 | A |
| KIAA1270 | XM_044835 | 1(as) | 9 | A |
| RPL31 | NM_013403.1 | 2(s) | 9 | A, B |
| 7SL | X04248.1 | 4(s), 1(as) | 8 | C |
| ENO1 | NM_001428 | 2(s) | 8 | |
| GSTP | NM_000852 | 2(s) | 8 | |
| ICAM2 | NM_000873 | 2(s), 1(as) | 8 | |
| INT-2/FGF3 | NM_005247 | 2(s) | 8 | C |
| LYN-B | NM_002350 | 2(as) | 8 | A |
| RPS24 | NM_001026 | 1(s), 1(as) | 8 | |
| FGFR1 | NM_000604.2 | 2(s), 1(as) | 6 | A |
| HES6 | XM_043579 | 1(s) | 6 | B |
| PKC zeta | NM_002744 | 2(s), 1(as) | 6 | B |
| RAN | NM_006325 | 1(s) | 6 | |
| RPA3 | NM_002947.1 | 1(s) | 6 | A |
| ZIN | NM_013403.1 | 1(as) | 6 | A, B |
| TAF7 | NM_005642 | 1(s) | 6 | A |
| AP1B1/BAM22 | NM_001127.1 | 2(s) | 5 | A |
| HNRPF | NM_004966 | 1(s) | 5 | A |
| HNRPMT | AF222689 | 1(s) | 5 | A |
| NFkB-1 | NM_003998.1 | 1(as) | 5 | A, B |
| NR3C1 | NM_000176 | 1(s) | 5 | A |
| PKC delta | NM_006254.1 | 2(s), 1(as) | 5 | C |
| BAG-1 | NM_004323.2 | 2(s) | 4 | A |
| GBC-11 | W84777 | 1(s) | 4 | A, B |
| HNRPA2B1 | NM_002137 | 1(s) | 4 | A |
| IF1 | NM_016311.1 | 1(s) | 4 | A |
| ITGA4 | NM_000885 | 1(s), 1(as) | 4 | |
| JunB | NM_002229.1 | 1(s) | 4 | C |
| GRP58 | NM_005313.1 | 1(s), 1(as) | 4 | |
| PKC eta | NM_006255.1 | 3(s), 1(as) | 4 | A, B, C |
| PSMB7 | NM_002799 | 1(s) | 4 | |
| RAB2L | NM_004761 | 1(s) | 4 | |
| RPL35 | NM_004632.1 | 2(as) | 4 | C |
| CDK2 | NM_001798.1 | 2(s) | 3 | A |
| DAP-3 | NM_004632.1 | 2(as) | 3 | A, B |
| EIF-3 | NM_003750 | 3(s) | 3 | A |
| GBC-12 | | 1(s) | 3 | A |
| IGF2R | NM_000876 | 2(s) | 3 | |
| KIFC1 | XM_042626 | 1(as) | 3 | |
| MET | NM_031517 | 2(s), 1(as) | 3 | |
| PCNA | NM_002592 | 1(s) | 3 | |
| PPP2R1B | NM_002716 | 2(as) | 3 | |
| RAB5B | NM_002868.1 | 1(s), 1(as) | 3 | |
| TDGF1 | NM_003212 | 1(as) | 3 | |
| ARFAPTIN1 | NM_014447 | 1(as) | 2 | |
| CDK10 | NM_003674 | 2(s) | 2 | B |
| CREB1 | NM_004379 | 1(s) | 2 | |
| EDF-1 | NM_003792 | 1(s) | 2 | |
| FLJ10006 | XM_041928 | 1(as) | 2 | |
| FLJ13052 | NM_023018 | 1(s) | 2 | |
| FOSL2 | NM_005253.1 | 1(s), 1(as) | 2 | |
| GBC-13 | | 1(s) | 2 | |
| GBC-14 | AL557138 | 1(s) | 2 | |
| GBC-15 | BE079876 | 1(s) | 2 | |
| GBC-16 | | 1(s) | 2 | |
| GBC-17 | | 1(s) | 2 | |
| GBC-18 | | 1(s) | 2 | |
| GNAS | M21139 | 1(as) | 2 | |
| IL4R | NM_000418 | 1(as) | 2 | |
| ITGA3 | NM_002204 | 1(as) | 2 | |
| MAP2K2 | NM_030622 | 2(as) | 2 | |
| MBD-1 | NM_015847 | 1(s), 1(as) | 2 | B |
| MCM-6 | NM_005915 | 1(s) | 2 | |
| MYL6 | NM_021019 | 2(s) | 2 | A |
| NUMA1 | NM_006185 | 1(s) | 2 | |
| PC4 | NM_006713 | 1(s) | 2 | |
| RAD23A | NM_005053 | 1(s) | 2 | |
| REL | NM_002908 | 1(s) | 2 | |
| RPA1 | NM_002945 | 1(as) | 2 | |
| RPL12 | NM_000976 | 1(s) | 2 | |
| RPS29 | NM_001032 | 1(s) | 2 | |
| SQSTM1 | NM_003900 | 1(s) | 2 | |

*A, confirmed by BrdU suicide assay; B, gave rise to cell line inhibited by IPTG; C, low infection rate

TABLE 2

Enriched Genes Previously Implicated in Cell Proliferation

| Gene | Accession No. | # Sequences (s/as) | # clones | Description | Association with cancer |
|---|---|---|---|---|---|
| CCN D1 | NM_001758 | 2(s), 2(as) | 9 | Cyclin, G1/S transition | Amplified in cancers |
| CDK2 | NM_001798 | 2(s) | 3 | Cyclin-dependent kinase, S-phase | Amplified in cancers |
| PCNA | NM_002592 | 1(s) | 3 | DNA replication | Upregulated in cancers |
| RPA3 | NM_002947 | 1(s) | 6 | DNA replication, excision repair | |
| RPA1 | NM_002945 | 1(as) | 2 | DNA replication | |
| MCM3 | NM_002388 | 3(s), 4(as) | 38 | DNA replication | |
| MCM6 | NM_005915 | 1(s) | 2 | DNA replication | |
| FEN1 | NM_004111 | 2(s), 2(as) | 12 | DNA replication and repair | |
| CDC20 | NM_001255 | 1(as) | 9 | CDC2-related kinase, mitosis | |

TABLE 2-continued

Enriched Genes Previously Implicated in Cell Proliferation

| Gene | Accession No. | # Sequences (s/as) | # clones | Description | Association with cancer |
|---|---|---|---|---|---|
| NUMA1 | NM_006185 | 1(s) | 2 | Nuclear reassembly in late mitosis | |
| RAN | NM_006325 | 1(s) | 6 | Small GTPase, mitosis | Ras family |
| CDK10 | NM_003674 | 2(s) | 2 | Cell cycle, G2/M | |
| C-KIT | NM_021099 | 4(s), 2(as) | 12 | Growth factor receptor, oncogene | Protooncogene |
| EFN A1 | NM_004428 | 1(s), 3(as) | 9 | Receptor tyrosine kinase ligand | RAS pathway regulator |
| LYN-B | NM_002350 | 2(as) | 8 | Tyrosine kinase | YES protooncogene |
| INT-2/FGF-3 | NM_005247 | 2(s) | 8 | Fibroblast growth factor | Mammary oncogene |
| FGFR1 | NM_000604 | 2(s), 1(as) | 6 | Fibroblast growth factor receptor, tyrosine kinase | Amplified in breast cancers |
| TDGF1 | NM_003212 | 1(as) | 3 | Teratocarcinoma derived growth factor 1 (EGF family) | Overexpressed in teratocarcinomas |
| MET | NM_031517 | 2(s), 1(as) | 3 | Hepatocyte growth factor receptor | Protooncogene |
| IL4R | NM_000418 | 1(as) | 2 | Interleukin-4 receptor | |
| STAT3 | NM_003150 | 4(s), 3(as) | 25 | Transcription factor (proliferation) | Upregulated in breast ca |
| STAT5b | NM_012448 | 4(s), 4(as) | 152 | Transcription factor (proliferation) | |
| C-FOS | NM_005252 | 3(s), 3(as) | 17 | AP-1 component | Protooncogene |
| NFκB-1 | NM_003998 | 1(as) | 5 | Stress, apoptosis, paracrine activities | |
| TAF7 | NM_005642 | 1(s) | 6 | Transcription initiation factor | |
| PC4 | NM_006713 | 1(s) | 2 | General positive coactivator of transcription | |
| CREB1 | NM_004379 | 1(s) | 2 | Transcription factor, regulates expression of cAMP-inducible genes including Cyclin A | |
| JUNB | NM_002229 | 1(s) | 4 | AP-1 component | Protooncogene |
| FOSL2 | NM_005253 | 1(s), 1(as) | 2 | AP-1 component | FOS-related |
| REL | NM_002908 | 1(s) | 2 | Transcription factor | Protooncogene |
| ADPRT | NM_001618 | 1(s), 1(as) | 10 | Poly(ADP ribosyl) transferase | |
| PKC zeta | NM_002744 | 2(s), 1(as) | 6 | Serine/threonine protein kinase | Stimulated by tumor promoters |
| PKC delta | NM_006254 | 2(s), 1(as) | 5 | Serine/threonine protein kinase | Stimulated by tumor promoters |
| PKC eta | NM_006255 | 3(s), 1(as) | 4 | Serine/threonine protein kinase | Stimulated by tumor promoters |
| MAP2K2 | NM_030662 | 2(as) | 2 | MAP kinase kinase | Implicated in medulloblastoma metastasis |
| GRP58 | NM_005313 | 1(s), 1(as) | 4 | Membrane signal transduction | |
| PPP2R1B | NM_002716 | 2(as) | 3 | Protein phosphatase 2 regulatory subunit β | |
| BAG1 | NM_004323 | 2(s) | 4 | Apoptosis inhibitor (Bcl-2 family) | Overexpressed in cancers |
| DAP3 | NM_004632 | 2(as) | 3 | Positive/negative apoptosis regulator | Overexpressed in gliomas |
| ITGA4 | NM_000885 | 1(s), 1(as) | 4 | Cell adhesion, signal transduction | Involved in Src pathway |
| ITGA3 | NM_002204 | 1(as) | 2 | Cell adhesion, signal transduction | Involved in colorectal cancer growth |
| ITGB5 | NM_002213 | 4(s), 1(as) | 30 | Cell adhesion, signal transduction | Correlates with invasiveness in gastric ca |
| AHRG | NM_001665. | 5(s), 1(as) | 43 | Small GTPase, cytoskeletal reorganization | Ras family, contributes to Ras transforming activity |
| GNAS complex | M21139 | 1(as) | 2 | G-protein alpha subunit s, knockout is embryonic lethal | |
| HSPCA | NM_005348 | 2(s) | 27 | Chaperone, protein folding | Overexpressed in breast ca, activates tyrosine kinases |
| EIF-3 | NM_003750 | 3(s) | 3 | Translation initiation factor | |
| RPL31 | NM_013403 | 2(s) | 9 | Ribosomal protein L31 | |
| RPL35 | NM_004632 | 2(as) | 4 | Ribosomal protein L35 | |
| RPL12 | NM_000976 | 1(s) | 2 | Ribosomal protein L12 | |
| RPS29 | NM_001032 | 1(s) | 2 | Ribosomal protein S29 | |
| RPS24 | NM_001026 | 1(s), 1(as) | 8 | Ribosomal protein S24 | |
| 18S RNA | K03432.1 | 8(s), 4(as) | 33 | Ribosomal RNA | |
| 28S RNA | M27830 | 3(s) | 17 | Ribosomal RNA | |
| 7SL | X04248 | 4(s), 1(as) | 8 | RNA component of signal recognition particle | |

TABLE 3

Enriched Genes That Have Not Been Previously Implicated in Cell Proliferation

| Gene | Accession No. | # Sequences (s/as) | # clones | Description | Association with cancer |
| --- | --- | --- | --- | --- | --- |
| Transcription factors | | | | | |
| ATF4 | NM_001675 | 5(as) | 369 | Activating transcription factor | Induced in breast ca by heregulin |
| HES6 | XM_043579 | 1(s) | 6 | Transcription co-factor, differentiation inducer | |
| NR3C1 | NM_000176 | 1(s) | 5 | Glucocorticoid receptor | |
| EDF1 | NM_003792 | 1(s) | 2 | Transcription factor, stimulates endothelial cell growth, represses endothelial cell differentiation | |
| MBD1 | NM_015847 | 1(s), 1(as) | 2 | Methylated DNA binding protein, transcription inhibitor | |
| RNA transport | | | | | |
| HRPMT1L2 | NM_001536 | 1(s) | 5 | Hnrp arginine methyltransferase | |
| HNRPF | NM_004966 | 1(s) | 5 | Heterogeneous nuclear ribonucleoprotein F | |
| HNRPA2B1 | NM_002137 | 1(s) | 4 | Heterogeneous nuclear ribonucleoprotein A2/B1 | |
| Signal transduction and cell adhesion | | | | | |
| ZIN | NM_013403 | 1(as) | 6 | Calmodulin-binding WD repeat protein | |
| Arfaptin 1 | NM_014447 | 1(as) | 2 | Similar to POR1 GTP-binding protein; may act in cellular membrane ruffling and formation of lamellipodia | |
| L1CAM | NM_000425 | 8(s), 4(as) | 20 | Cell adhesion, neural | |
| ICAM2 | NM_000873 | 2(s), 1(as) | 8 | Cell adhesion, intercellular | |
| Intracellular transport | | | | | |
| AP1B1/BAM22 | NM_001127 | 2(s) | 5 | Clathrin-associated adaptor protein | |
| RAB2L | NM_004761 | 1(s) | 4 | Small GTPase, intracellular transport | Ras family |
| KIFC1 | XM_042626 | 1(as) | 3 | Intracellular trafficking | |
| Rab5B | NM_002868 | 1(s), 1(as) | 3 | Small GTPase, vesicle transport | Ras family |
| Protein processing | | | | | |
| NIN283 | NM_032268 | 1(s) | 11 | ubiquitin-mediated protein modification | |
| PSMB7 | NM_002799 | 1(s) | 4 | Proteasome subunit β7 | |
| SQSTM1 | NM_003900 | 1(s) | 2 | Sequestosome 1; ubiquitin-mediated protein degradation | |
| RAD23A | NM_005053 | 1(s) | 2 | Nucleotide excision repair, ubiquitin-mediated protein degradation | |
| Other | | | | | |
| VWF | NM_000552 | 6(s), 5(as) | 39 | Blood clotting | |
| GSTP | NM_000852 | 2(s) | 8 | Xenobiotic metabolism | |
| ENO1 | NM_001428 | 2(s) | 8 | Glycolysis | |
| IF1 | NM_016311 | 1(s) | 4 | Inhibitor of Fo/F1 mitochondrial ATPase | |
| MYL6 | NM_021019 | 2(s) | 2 | Contractility | |
| FLJ13052 | NM_023018 | 1(s) | 2 | NAD kinase (predicted) | |
| GBC-14 | AL557138 | 1(s) | 2 | similar to tyrosine 3-monooxygenase/tryptophan 5-monooxygenase activation protein, zeta polypeptide | |
| KIAA1270 | XM_044835 | 1(as) | 9 | Alanyl-tRNA synthetase homolog | |
| IGF2R | NM_000876 | 2(s) | 3 | Insulin-like growth factor 2 receptor | Mutated in breast cancers |
| Unknown function | | | | | |
| GBC-1 | NM_031221 | 2(s) | 70 | Contains helical repeat peptide | |
| FLJ10006 | XM_041928 | 1(as) | 2 | | |
| GBC-3 | AA443027 | 1(s) | 12 | HC 3q29 | |
| GBC-11 | | 1(s) | 4 | HC 14 | |
| GBC-12 | | 1(s) | 3 | HC 1 | |
| GBC-13 | | 1(s) | 2 | | |
| GBC-15 | BE079876 | 1(s) | 2 | | |
| GBC-16 | | 1(s) | 2 | | |
| GBC-17 | | 1(s) | 2 | | |
| GBC-18 | | 1(s) | 2 | | |

TABLE 4

Nucleotide Sequences of GSEs

| Gene/ Accession No. | No. of Clones | Orientation | SEQ ID NO | | Sequence | |
|---|---|---|---|---|---|---|
| 18S RNA K03432.1 | 1 | AS | 4 | 1089 | gccgctagaggtgaaattccttggaccggcgcaagacggaccagagcgaaagcatttgccaa gaatgttttcattaatcaagaacgaaagtcggaggttcgaagacgatcagataccgtcgtag ttccgaccataaacgatgccgaccggcgatgcggcggcgttattcccatgacccgccgg | 1271 |
| | 2 | AS | 5 | 1413 | ccggacacggacaggattgacagattgatagctctttctcgattccgtgggtggtggtgcat ggccgttcttagttggtggagcgatttgtctggttaattccgataacgaacgaga | 1529 |
| | 6 | S | 6 | 177 | caaagattaagccatgcatgtctaagtacgcacggccggtacagtgaaactgcgaatggctc attaaatcagttatggttcctttggtcgct | 268 |
| | 7 | S | 7 | 1414 | cggacacggacaggattgacagattgatagctctttctcgattccgtgggtggtggtgcatg gccgttc | 1482 |
| | 4 | AS | 8 | 154 | ctgccagtagcatatgcttgtctcaaagattaagccatgcatgtctaagtacgcacggccgg tac | 218 |
| | 1 | AS | 9 | 199 | taagtacgcacggccggtacagtgaaactgcgaatggctcattaaatcagttatggt | 255 |
| | 2 | S | 10 | 570 | cggagagggagcctgagaaacggctaccacatccaaggaaggca | 613 |
| | 3 | S | 11 | 177 | caaagattaagccatgcatgtctaagtacgcacggccggta | 217 |
| | 1 | S | 12 | 1040 | cggaactgaggccatgattaagagggacggccggg | 1074 |
| | 1 | S | 13 | 1433 | cagattgatagctctttctcgattccgtgggtggt | 1467 |
| | 1 | S | 14 | 224 | aactgcgaatggctcattaaatcagttatggttcctttggtcgct | 268 |
| | 4 | S | 15 | 185 | aagccatgcatgtctaagtacgcacggccg | 214 |
| 28S RNA M27830.1 | 10 | S | 16 | 83 | ccctactgatgatgtgttgttgccatggtaatcctgctcagtacgagaggaaccgcaggttc agacatttggtgtatgtgcttggctgaggagccaatggggcgaacgtaccatctgt | 200 |
| | 4 | S | 17 | 1 | gaattcaccaagcgttggattgttcacccactaataggaacgtgagct | 49 |
| | 3 | S | 18 | 136 | cgcaggttcagacatttggtgtatgtg | 162 |
| 7SL RNA X04248.1 | 3 | S | 19 | 29 | cccagctactcgggaggctgaggctggaggatcgcttgagtccaggagttctgggctgtagt gcgctatgccgatcgggtgtccgcactaagttcggcatcaatatgg | 136 |
| | 1 | S | 20 | 70 | ccaggagttctgggctgtagtgcgctatgccgatcgggtgtccgcactaagttcggcatcaa tatggt | 137 |
| | 3 | S | 21 | 144 | ccggggagcgggggaccaccaggttgcctaaggagggggtga | 183 |
| | 9 | AS | 22 | 24 | gtagtcccagctactcgggaggctgaggctggaggatcgcttga | 67 |
| | 3 | S | 23 | 153 | ggggaccaccaggttgcctaaggagggggtga | 183 |
| ADPRT NM_001618 | 9 | S | 24 | 2736 | gctgtgcacgggtctaggaccaccaactttgctgggatcctgtcccagggtcttcggatag ccccgcctgaagcgcccgtgacag | 2821 |
| | 1 | AS | 25 | 2422 | gaccctcccctgagcagactgtaggccacctcgatgtccagcaggttgtcaagcatttcc accttggcctgcacactgtctgc | 2504 |
| ARFAPTIN1 NM_014447 | 2 | AS | 26 | 26 | ttcacactgaccaaccgccgaggacagtcggaccggcgacctctcaacccagcc | 79 |
| ATF4 NM_001675.1 | 359 | AS | 27 | 833 | acaccttcgaattaagcacattcctcgattccagcaaagcaccgcaacatgaccgaaatgag cttcctgagcagcg | 909 |
| | 6 | AS | 28 | 833 | gacaccttcgaattaagcacattcctcgattccagcaaagcaccgcaaca | 883 |
| | 2 | AS | 29 | 838 | ----ccttagaattaagcacattcctcgattccagcaaagcgccgcaacatgacggaaa | 893 |
| | 1 | AS | 30 | 843 | ---------gaattaagcactttcctcgagtccagcaaagcccgca------------ | 880 |
| | 1 | AS | 31 | 864 | cgctgctcagcaagctctgttcggtcatgttgcggtgctttgctgg | 909 |
| IF1 NM_016311.1 | 4 | S | 32 | 13 | ccagcagcaatggcagtgacggcgttggcggcgcggacgtggcttggcgtgtggggc | 69 |

TABLE 4-continued

Nucleotide Sequences of GSEs

| Gene/ Accession No. | No. of Clones | Orientation | SEQ ID NO | | Sequence | |
|---|---|---|---|---|---|---|
| BAG1 NM_004323.2 | 3 | S | 33 | 434 | ccgggacgaggagtcgacccggagcgaggaggtgaccagggaggaaatggcggcagctgggc tcaccgtgactgtcacccacagc | 518 |
| | 1 | S | 34 | 461 | ggaggtgaccagggaggaaatggcggcagctgggctcaccgtgactgtcacccacagc | 518 |
| AP1B1 NM_001127.1 | 5 | S | 35 | 275 | gccaagagtcagcctgacatggccattatggccgtcaacacctttgtgaaggactgtgagga | 336 |
| | 1 | S | 36 | 286 | gcctgacatggccattatggccgtcaacacctttgtgaaggactgtgag | 334 |
| CDC20 NM_001255 | 4 | AS | 37 | 1001 | gccagggacaccatgctacggccttgacagcccccttgatgctgggtaatgtctgcagagga acccagccaccctctccaggagcactgggccacacattgaccaagttatcattaccaccact ggccaaatgtcgtccatctggggcccagcgcagcccacacacttcctggctgtggccactca gtgtggccacatggtgttctgct | 1209 |
| CDK10 NM_003674 | 1 | S | 38 | 1159 | gccccagccacctccgagggccagagcatgcgctgtaaacc | 1199 |
| | 1 | S | 39 | 1734 | ctaccaggagagccctgggctggaggctgagctgcatccctgctccccacatggaggaccca acaggaggccgtggctctgatgctgagcgaagct | 1829 |
| CDK-2 NM_001798.1 | 2 | S | 40 | 322 | agatctctctgcttaaggagcttaaccatcctaatattgtcaagctg | 368 |
| | 1 | S | 41 | 645 | tacacccatgaggtggtgaccctgtggtaccgagctcctgaaatcctcctgggctgca | 702 |
| c-FOS NM_005252.2 | 1 | AS | 42 | 347 | cactgccatctcgaccagtccggacctgcagtggctggtgcagcccgccctcgtctcctctg tggccccatcgcagaccagagcccctcaccctttcggagtccccgccccc | 458 |
| | 1 | AS | 43 | 246 | cactcacccgcagactccttctccagcatgggctcgcctgtcaacgcgcaggacttctgcac ggacctggcc | 317 |
| | 12 | S | 44 | 57 | agcgaacgagcagtgaccgtgctcctacccagctctgcttcacagcgcccacctgtctccgc ccct | 122 |
| | 1 | S | 45 | 1342 | gcccgagctggtgcattacagagaggagaaacacatcttccctagagggttcctgtag acctaggg | 1407 |
| | 1 | AS | 46 | 717 | gaggcagggtgaaggcctcctcagactccggggtggcaacctctggcaggcccccagtcaga tcaagggaagccacagacatctcttctgggaagcccaggtcatcagggatcttgcaggcggg tcggtgagctgccaggatgaactctagttttttccttctccttt | 882 |
| | 1 | S | 47 | 596 | taagatggctgcagccaaatgccgcaaccggagga | 630 |
| c-KIT NM_021099.2 | 2 | AS | 48 | 2448 | gcgatttcgggctagccagagacatcaggaatgattcgaattacgtggtcaaaggaaatgca cgactgcccgtgaagtggatggcaccagagagcattttcagctgcg | 2555 |
| | 4 | AS | 49 | 2632 | cccagggatgccggtcgactccaagttctacaagatgatcaaggaaggcttccggatggtca gcccggagcacgcgcctgccgaaatgtatgacgtcatgaagacttgctgggacg | 2747 |
| | 2 | S | 50 | 3466 | aacggggcatcggaagtctggtcacgctaagaagaccgaggctgagaaggaacaagccaggg gaagcgtga | 3536 |
| | 1 | S | 51 | 4650 | gctggtttggaggtcctgtggtcatgtacgagactgtcaccagttaccgcgctctgtttgaa acatgtc | 4718 |
| | 2 | S | 52 | 3508 | tgagaaggaacaagccaggggaagcgtgaacaatgatgctctgctctgggctgcc gctcgggcttctgtacaactgacctggttt | 3592 |
| | 1 | S | 53 | 3595 | gaacaagccaggggaagcgtgaacaatgatgctctgctctgggctgccgctcgggcttctgta caactgacctggtttctc | 3515 |
| CREB1 NM_004379 | 2 | S | 54 | 199 | aagcccagccacagattgccacattagcccaggtatctatgccagcagctcatgcaacatca tctg | 264 |
| CCND1 NM_001758.1 | 6 | S | 55 | 311 | tgcggaagatcgtcgccacctggatgctggaggtctgcgaggaacagaagtgcgaggaggag gtcttcccgctggccatgaactacctggaccgcttcctgtcgctgg | 418 |
| | 1 | S | 56 | 935 | agaacatggaccccaaggccgcc | 957 |
| | 2 | AS | 57 | 331 | tggatgctggaggtctgcgaggaacagaagtgcgaggaggaggtcttc ccgctggccatgaactacctggaccgcttcct | 411 |
| | 1 | | 58 | 406 | cacagcttctcggccgtcaggggatggtctccttcatcttagaggccacgaacatgcaagt ggcccccagcagctgcaggcggctctttttcacgggctccagcgacaggaa | 518 |

TABLE 4-continued

Nucleotide Sequences of GSEs

| Gene/ Accession No. | No. of Clones | Orientation | SEQ ID NO | | Sequence | |
|---|---|---|---|---|---|---|
| DAP3 NM_004632.1 | 2 | AS | 59 | 1249 | gcggcactgtgcctacctctaagccaagatcacagcatgtgaggaagacagtggacatctgc tttatgctggacccagtaagatgaggaagtcgggcagtacacaggaagaggagccaggccct tgtacctatgggattggacaggactgcagttggctctggacctgc | 1417 |
| | 1 | AS | 60 | 1259 | gcctacctctaagccaagatcacagcatgtgaggaagacagtggacatctgctttatgctgg acccagtaagatgaggaagtcgggcagtacacaggaagaggagccaggcccttgtacctatg ggattggacaggactgcagttggctctggacctgc | 1417 |
| EDF1 NM_003792 | 2 | S | 61 | 97 | ggccaaatccaagcaggctatcttagcggcacagagacgaggaggagat | 145 |
| eIF-3 NM_003750 | 1 | S | 62 | 3259 | ggcgaggaggcgctgatgatgagcgatcatcctggcgtaatgctgatgatgaccggggtccc aggcgaggggttggatga | 3337 |
| | 1 | S | 63 | 40 | gcagcgttgggcccatgcaggacgc | 64 |
| | 1 | S | 64 | 269 | cagcttcaggcagaaacagaaccaa | 293 |
| ENO-1 NM_001428 | 7 | S | 65 | 5 | agatctcgccggctttacgttcacctcggtgtctgcagcaccctccgcttcctctcctaggc gacg | 70 |
| | 1 | S | 66 | 11 | cgccggctttacgttcacctcggtgtctgcagcaccctccgcttcct | 57 |
| EFNA1 NM_004428 | 5 | S | 67 | 228 | cgcactatgaagatcactctgtggcagacgctgccatggagcagtacatactgtacctggtg gagcatgaggagtaccagctgt | 311 |
| | 2 | AS | 68 | 517 | tgctgcaagtctcttctcctgtggattgacatgggcctgaggactgtgagtgattttgcca | 577 |
| | 1 | AS | 69 | 1183 | tggcacagccccctgctggcacagctctgggagtgctgccccaggatgggagagaatgca gtacctggctacaaacttctctgtggcagctccacagatgaggtctt | 1291 |
| | 1 | AS | 70 | 467 | gacagtcaccttcaacctcaagcagcggtcttcatgctggtggatggg | 514 |
| FEN1 NM_004111.3 | 5 | S | 71 | 634 | gccacagctcaagtcaggcgagctggccaaacgcagtgagcggcgggctgaggcagagaagc agctgcagcaggctcaggctgctgg | 720 |
| | 4 | AS | 72 | 841 | ggcagaggccagctgtgctgccctggtgaaggctggcaaagtctatgctgcggctaccga | 900 |
| | 2 | AS | 73 | 634 | gccacagctcaagtcaggcgagctggccaaacgcagtgagcggc | 677 |
| | 1 | S | 74 | 651 | gcgacctggacaaacgcattgagcggcggcctgaggcagagaagcagctgtatcatgctcaa gctgctgg | 720 |
| FGFR1 NM_000604.2 | 1 | S | 76 | 2004 | ggtaacagtgtctgctgactccagtgcatccatgaactctgggggttcttctggttcggccat cacggctctcctccagtgggactcccatgctagcaggggtctctgagtatgagcttcccgaa gacccctcgcgggagctgcctcgggacagactggtcttaggc | 2169 |
| | 1 | AS | 77 | 2844 | ggaggaacttttcaagctgctgaaggagggtcaccgcatggacaagcccagtaactgcacca acgagctgtacatgatgatgcgggactgctggcatgcagtgccctcacagagacccaccttc aagcagctggt | 2978 |
| | 4 | S | 78 | 1930 | ggtaccaagaagagtgacttccacagccagatggctgtgcacaagctggccaagagcatcct ctgcgcagacaggtaacagtgtctgctgactccagtg | 2029 |
| GBC-1 NM_031221 | 68 | S | 79 | 876 | tcctcacatcccagacgatgggcggccaggcagagacgctcctcacttcccagacggggtag cggccg | 943 |
| | 2 | S | 80 | 876 | tcctcacatcccagacgatgggcggccaggcagagacgctcctcacttcccag | 928 |
| FLJ10006 XM_041928 | 2 | AS | 81 | 1010 | agaaagtgaggaccctcaggaggctgcaggccagtgagtcagcaaatgaagagattcccgaa ccccgaatcagtgattcggaaagtgaggatcc | 1102 |
| FLJ13052 NM_023018 | 2 | S | 82 | 2508 | ctaacacagcgagggactcaacacgctgattctcctcctgcctctcccg | 2556 |
| FOSL2 NM_005253.1 | 1 | S | 83 | 708 | ggcggggctggacaatgcccagcgctctgtctcaagcccatcagcattgctgggggcttcta cggtgaggatcccc | 784 |
| | 1 | AS | 84 | 881 | ggtgactcctgctccaggacgctaggataggtga | 848 |
| GBC-11 W84777 | 4 | AS | 85 | 437 | cagagcccccaaaacgctgggcagagttgacaggacccaaatgctaaagttgtggaggg | 378 |
| GBC-12 | 4 | S | 86 | | tggggagaccggagacggtggctggggtgtcctcagcccgggagagctgagtcagccgcgc cccgcacacagcatacttaggagccaaggacttggacctcgcttctcgccggtacgcga | |

TABLE 4-continued

Nucleotide Sequences of GSEs

| Gene/ Accession No. | No. of Clones | Orientation | SEQ ID NO | | Sequence | |
|---|---|---|---|---|---|---|
| GBC-13 | 3 | S | 87 | | accccctggnaacatggflaaatataaaacaacttggtgtttttgaaaaaccgcaaagcgtta tggtgtggatgtaacacaggggtgtggtgt | |
| GBC-14 AL557138 | 2 | S | 88 | 176 | tggaggaaaccccgtgtctgcggagcggctgtagcctgtgagcagcgagatccagggacag | 236 |
| GBC-15 BE079876 | 2 | S | 89 | 107 | cagctacccagaagtctgaggcaggagaaatgctggaacccggggaggcagagg | 159 |
| GBC-16 | 2 | S | 90 | | cagcgatccgtccagcagatgacgaatatcgacggccatttccggcataccgagctgttgca taatgcccgcagactgtgct | |
| GBC-17 | 2 | S | 91 | | cggaagagctcacaatgctcatttcgcgtctcgctcgggtgttgtgctgttcttaatactg tgggcaattcaggtgtgtcgcttagaaaacggaggtactcaatggagtcctcaacaatgagg ggccctgttcatggctttgtgttggccgttcgttccacatgttctt | |
| GBC-18 | 2 | S | 92 | | cgatgattattttcttggcaaagttttttagcagaacgtcaaaaattgattacatcttttaaa cgtggtttattaccggc | |
| GBC-2 | 1 | | 93 | 1 | agagcgaggcgtgaagtccacacgcccagccccgtcgcagtgtggttgccgagcaaggctac gtctgcggcgcgtgcggta | 81 |
| GBC-3 AA443027 | 12 | S | 94 | 4 | ccgggatgaagtgacccagcagaaataccagagaccggagacggaatggcccagggtcagcc tccacccggaaccggaggatgcagcgaagacgtctc | 101 |
| GBC-4 AV710590 | 1 | AS | 95 | 87 | cctcgctcaggattgcttcccgcggtgcctcccgcggctgcacggaaggccacgaaccgaca acttgcacagcagccatcttttct | 1 |
| GNAS NM_000516 | 2 | AS | 96 | 44 | cgcgcgcagctccccgcccctcgagccgaggccgaggggggctgatggccgccgccgggccga g | 106 |
| GSTP NM_000852 | 7 | S | 97 | 275 | ggaccagcaggaggcagccctggtggacatggtgaatgacggcgtggaggacctccgctgca | 336 |
| | 1 | S | 98 | 670 | tgcctggctgcgtttcccctgctctcagcatatgtggggcgcctcagcgcccggcccaagct caaggccttcctggcctcccctgagtacgtgaacttccccatcaatggcaacgggaaacagt gagg gttggg | 537 |
| HES6 XM_043579 | 6 | S | 99 | 935 | gcagggcagcccctggtaaccagcccagtcaggcccccagccccgtttcttaagaaacttttta gggaccctgcagctctg | 1013 |
| HNRPA2B1 NM_002137 | 4 | S | 100 | 826 | cggaccaggaccaggaagtaactttagaggaggatctgatggatatggcagtggacgtggat ttggggatggctata | 902 |
| HNRPF NM_004966 | 5 | S | 101 | 1000 | caggcctggaaaggatgaggcctggtgcctacagcacaggctacggggctacgaggagtac agtggcctcagtgatggctacggcttcaccaccgacctgttcgggagagacctcagctactg tctctccggaatgtatgaccacagatacgccgac | 1157 |
| HRMT1L2 NM_001536 | 5 | S | 102 | 2707 | ggtgcgggtgaagatggcggcagccgaggccgcgaactgcat | 2748 |
| HSPCA NM_005348 .1 | 24 | S | 103 | 1554 | caaggaccaggtagctaactcagcctttgtggaacgtcttcggaaacatggc | 1605 |
| | 3 | S | 104 | 1553 | ccaaggaccaggtagctaactcagcctttgtggaac | 1588 |
| ICAM2 NM_000873 | 5 | S | 105 | 12 | ggcagcccttggctggtccctgcgagcccgtgtggagactgccagagatgtcctctttcggtta caggaccctgactgtggccctcttcaccctgatctgctg | 112 |
| | 2 | S | 106 | 705 | gagcctgtgtcggacagccagatggtcatcatagtcacggtggtgtcggtgttgctgtccct gt | 768 |
| | 1 | AS | 107 | 745 | gccgctcactccccgtaggtgcccatccgctgctggcgcaagtgctggccgaagatgaagca gagcaggacagatgtcacgaacagggacagcaacaccgacacca | 850 |
| IGF2R NM_000876 | 2 | S | 108 | 903 | gaagctggtgcgcaaggacaggcttgtcctgagttacgt | 941 |
| | 1 | S | 109 | 1571 | gcggtgccaccgacgggna&gaagcgctatgacctgtccgcgctggtccgccatgcagaacc | 1631 |
| IL4R NM_000418 | 2 | AS | 110 | 1178 | ctcctcctcctcacactccaccgggngcctcaaacaactccacacatcgcaccacgctgatg ctctctggccagaggactgtcttgctgatctccactgggcaccatgctgattttccagagcc | 1300 |
| INTB5 NM_002213 .1 | 25 | S | 111 | 67 | tggggctctgcgcgctcctgccccggctcgcaggtctcaacatatgcactagtggaagtgcc acctcatgtgaagaatgtctgctaatccacccaaaatgtgcctggtgctccaaagaggactt cggaagcc | 198 |

TABLE 4-continued

Nucleotide Sequences of GSEs

| Gene/ Accession No. | No. of Clones | Orientation | SEQ ID NO | | Sequence | |
|---|---|---|---|---|---|---|
| | 2 | S | 112 | 2088 | ccaaggactgcgtcatgatgttcacctatgtggagctccccagtgggaagtccaacctgacc gtcctcagggagccagagtgtggaaacaccccaacgccatgaccatcctcct | 2203 |
| | 1 | S | 113 | 1722 | ggccatggcgagtgtcactgcggggaatgcaagtgccatgcaggttacatcggggacaactg taactgctcgacagacatcagcaca | 1808 |
| | 1 | S | 114 | 2118 | gtggagctccccagtgggaagtccaacctgaccgtcctcagggagccagagtgtggaaacac cccaacgccatgaccatcctcctggctg | 2208 |
| | 1 | AS | 115 | 2047 | tgaaagatgaccaggaggctgtgctatgtttctaca | 2082 |
| ITGA3 NM_002204 | 2 | AS | 118 | 1993 | tgggcgtcctccccggagcgctccgaggtccgggtgttcgtcacgttgatgctcaggagcaa tttccggacgtctctgctgtactggagcctg | 2085 |
| ITGA4 NM_000885 | 2 | S | 119 | 1188 | ggcgcgaacccggccccgaaggccgccgtccgggagacggtgatgctgttgctgtgcctgg gggtcccgaccggccgccccctacaacgt | 1276 |
| | 1 | AS | 120 | 2797 | tgtgttctacagttagcttctctgctggacacctgtatgcttcnctgtaatca | 2848 |
| JunB NM_002229 .1 | 1 | S | 121 | 306 | cgggatacgccgggcccctggtggcctctctctacacgactacaaac | 353 |
| | 1 | S | 122 | 322 | ccctggtggcctctctctacacgactac | 349 |
| KIAA1270 XM_044835 | 9 | AS | 123 | 1591 | cctgtccaagaggaggccacagcgctggcctttccccacggaggccactgctgtcccgtcct ctgtatacagttgcaacacctgggcctcacaggt | 1683 |
| KIFC1 XM_042626 | 3 | AS | 124 | 2193 | tctggatccgtcttcacttcctgttggcctgagcagtaccaataacacactggttcaccttg gagcaa | 2125 |
| L1CAM NM_000425 .2 | 1 | AS | 125 | 4465 | ttggggacccaggagacgacacttggatgttgtgtggtgggtaccgaaggcagcgtgtgtat ggagctcctgaaagccggccatgggtgggc | 4392 |
| | 1 | AS | 126 | 2457 | caggcaatccctgagctggaaggcattgaaatcctcaactcaagtgccgtgctggtcaagtg gcggccggtggacctggcccaggtcaagggccacctccgcggatacaatg | 2568 |
| | 2 | S | 127 | 1389 | agtgttcagtggctggacgaggatgggacaacagtgcttcaggacgaacgcttcttccccta tgccaatgggaccctgggcattcgagacctccaggccaatgacac | 1495 |
| | 2 | AS | 128 | 1518 | gccaatgaccaaaacaatgttaccatcatggctaacctgaaggttaaagatgcaactcagat cactcaggggccccgcagcacaatgagaagaaaggttccagggg | 1623 |
| | 1 | S | 129 | 666 | accaggaccatcattcagaaggaacccattgacctccgggtcaaggccaccaacagcatgat tgacaggaagccgcgcctgctcttccccaccaactccagcagccacc | 774 |
| | 1 | S | 130 | 591 | ggcaacctctactttgccaatgtgctcacctccgacaaccactcagactacatctgccacgc ccacttcccaggcaccaggaccatcatt | 680 |
| | 1 | S | 131 | 253 | ccaaggaagagctgggtgtgaccgtgtaccagtcgcccact | 294 |
| | 1 | S | 132 | 1367 | ggccttcggagcgcctgtgcccagtgttcagtggctggacgaggatgggacaacagtgctt | 1427 |
| | 1 | S | 133 | 729 | gacaggaagccgcgcctgctcttccccaccaactccagcagccacctggtg | 779 |
| | 12 | S | 134 | 94 | aatatgaaggacaccatgtgatggagccacctgtcaccac | 133 |
| | 1 | AS | 135 | 2889 | cccctggatgagggggggcaaggggcaact | 2917 |
| | 7 | S | 136 | 94 | aatatgaaggacaccatgtgatggagc | 120 |
| LYN-B NM_002350 | 1 | AS | 137 | 1243 | tacatcatcaccgagttcatggctaagggtagtttgctggatttcctcaagagtgatgaag gtggcaaggtgctgctgcccaagctcattgacttctcggcccagattgca | 1353 |
| | 4 | AS | 138 | 1208 | ggctgtacgctgtggtcaccaaggaggagcccatctacatcatcaccg | 1255 |
| PSMB7 NM_002799 | 4 | S | 139 | 595 | caagaatctggtgagcgaagccatcgcagctggcatcttcaacgacctgggc | 647 |
| MAP2K2 NM_ 030662.1 | 1 | AS | 140 | 435 | tcatcgtctttgagttcgccgaccttggctttctgggtgag | 475 |
| | 1 | AS | 141 | 881 | ccgctccggagccatgtaggagcgcgtgcccacgaaggagttggccatggagtctatgagct ggccgctcaccccgaagtcacacagcttgatctcc | 977 |

TABLE 4-continued

Nucleotide Sequences of GSEs

| Gene/ Accession No. | No. of Clones | Orientation | SEQ ID NO | Sequence | |
|---|---|---|---|---|---|
| MBD1 NM_015847 | 1 | S | 142 | 2829 cctcgtgccgaattcttggcctcgagggccaaattccctatagtgagtcgtattaaattcg | 2889 |
| | 1 | AS | 143 | 2846 tttaatacgactcactatagggaatttggccctcgaggcc | 2885 |
| MCM3 NM_002388.2 | 3 | AS | 144 | 2207 cactccaaagacggcagactcacaggagaccaaggaatcccagaaagtggagttgagtgaat ccaggttgaaggcattcaaggtggccctcttggatgtgttccgggaagctcatgcgcagtca atcggcatgaatcgcctcacagaatccatcaaccgggacagcgaagagcccttctcttcagt tg | 2394 |
| | 6 | S | 145 | 1597 tgcccttgggtagtgctgtggatatcctggccacagatgatcccaactttagccaggaagat cagcaggacacccagat | 1675 |
| | 14 | AS | 146 | 1707 accaagaagaaaaaggagaagatggtgagtgcagcattcatgaagaagtacatccatgtggc caaatcatcaagcc | 1783 |
| | 4 | AS | 147 | 1597 tgcccttgggtagtgctgtggatatcctggccacagatgatcccaactttagccaggaagat cagcaggacacccagat | 1675 |
| | 6 | S | 148 | 2410 tgagcaagatgcaggatgacaatcaggtcatggtgtctgag | 2450 |
| | 1 | AS | 149 | 2400 acccaagttcggagacgaggcctcctcagatgaggaagatgatgccctcagacaccatgacc tgattgtcatcctgcatcttgctcagagcaacctg | 2496 |
| | 1 | S | 150 | 2799 agcagtggctcatccgccctacttcccatcccacacaaacccaattgtaaataacatatgac ttcgtgagtacttttggg | 2721 |
| MCM6 NM_005915 | 2 | S | 151 | 2127 gccctgctcctgtgaacgggatcaatggctacaatgaagacataaatcaagagtctgctccc aaagcc | 2194 |
| MYL6 NM_021019 | 1 | S | 155 | 35 gtcaagatgtgtgacttcaccgaagaccagaccgcagagttcaaggaggccttccagctgtt tgaccgaacag | 107 |
| | 1 | S | 156 | 54 ccgaagaccagaccgcagagttcaaggaggccttccagctgtttgaccgaacaggtgatggc aagatcctgtacagccagtg | 135 |
| NFkB1 NM_003998.1 | 5 | AS | 157 | 1 ggccaccggagcggcccggcgacgatcgctgacagcttcccctgcc | 46 |
| NIN283 NM_032268 | 11 | S | 158 | 1116 ggcaccccttctgcactgacttccagatatggttctcccttcctccctgaggacaccaaatt ggatgagagcaagtttgagagaag | 1202 |
| NR3C1 NM_000176 | 5 | S | 159 | 511 gcaaacctcatatgtcgaccagtgttccagagaaccccaagagttcagcatccactgctgtg tctgctgcccccacagagaaggagtt | 599 |
| NUMA1 NM_006185 | 2 | S | 160 | 4197 ggagctgacctcacaggctgagcgtgcggaggagctgggccaagaattgaaggcgtggc | 4255 |
| GRP58 NM_005313.1 | 3 | S | 161 | 1166 caatctgaagagataccctgaagtctgaacctatcccagagagcaatgatgggcctgtgaagg tagtggtagc | 1237 |
| | 1 | AS | 162 | 1084 ttagcagttctgatagcaacaacaggaatctctccagcagtgctctccaagtgagtgagcgg ccgc | 1034 |
| PC4 NM_006713 | 2 | S | 163 | 93 tgctccagaaaaacctgtaaagagacaaaagacaggtgagacttcgagagccctg | 147 |
| PCNA NM_002592 | 3 | S | 164 | 1 ccgctacaggcaggcgggaaggaggaaagtctagctggtttcggcttcaggagcctcaga gcgagcgggcgaacgtcgcgacgacgggctgagacct | 97 |
| PKC delta NM_006254.1 | 1 | S | 165 | 897 gcggcatcaaccagaagcttttggctgaggccttgaaccaagtcacccagagagcctccc ggagatcagactcagcctcctcagagcctgttgggatatatcagggtttcgagaagaagacc ggagtt | 1024 |
| | 1 | S | 166 | 667 gatcatcggcagatgcactggcaccgcggccaacagccgggacactatattccagaaaga acgcttcaacatcgacatgccgcaccgcttcaaggttcacaactacatg | 775 |
| | 3 | AS | 167 | 1935 cacccagagactacagtaactttgaccaggagttcctgaacgagaaggcgcgcctctcctac agcg | 2000 |
| PKC eta NM_006255.1 | 1 | S | 168 | 327 tgggccagaccagcaccaagcagaagaccaacaaacccacgtacaacgaggagttttgcgct aacgtcaccgacggcggccacctcgagttg | 418 |
| | 1 | S | 169 | 383 tgcgctaacgtcaccgacggcggccacctcgagttggccgtcttccacgagacccccctggg ctacgaccacttcgtggccaactgcaccctgcagttccaggagct | 486 |

TABLE 4-continued

Nucleotide Sequences of GSEs

| Gene/ Accession No. | No. of Clones | Orientation | SEQ ID NO | | Sequence | |
|---|---|---|---|---|---|---|
| | 1 | AS | 170 | 371 | aacgaggagttttgcgctaacgtcaccgacggcggccacctcgagttggccgtcttccacga gaccccctgggc | 445 |
| | 1 | S | 171 | 362 | cccacgtacaacgaggagttttgcgctaa | 390 |
| PKCZETA NM_002744 | 4 | S | 172 | 386 | acggccacctcttccaagccaagcgctttaacaggagagcgtactgcggtcagtgcagcg | 445 |
| | 1 | S | 173 | 163 | ccgctcaccctcaagtgggtggacagcgaaggtgacccttgcacggtgtcctcccagatgg agctggaagaggctttccgcctggcccgtcagtgcagggatgaaggcctcatcattcatg | 283 |
| | 1 | AS | 174 | 842 | gacgtactcaatgaccaggaacaaccgacttgtcgtctggaagcaggagtgtaatccgacca ggaaggggttgctggatgcctgctcaaacacgtgcttctctgtctgtacccagtcaatatcc tcgccatcatgcaccagctctttcttcaccactt | 999 |
| PPP2R1B NM_002716 | 2 | AS | 175 | 504 | acggaattgctgtctgatttctgctttaacagcatttgatgccctgggatagcaaacgctg aacaaaccacatgc | 578 |
| | 1 | AS | 176 | 805 | aggacccatggctttctggagctctgaaaatctgtcagccaccatatagcgaacgcgcca agatttatcttctgctgcttgtcgaagtg | 893 |
| RAB2L NM_004761 | 4 | S | 177 | 871 | gtcacacagtttaacaaggtggcaggggcagtggttagttctgtcctgggggctacttcc actggagagggacctggggaggtgaccatacggcc | 965 |
| RAB5B NM_002868 | 2 | S | 178 | 834 | aacaccaggcagctgttccgactggcctcct | 864 |
| .1 | 1 | AS | 179 | 1345 | gggcggaggtggaggtgcagggtcaactgtggctctgta | 1383 |
| RAD23A NM_005053 | 2 | S | 180 | 1351 | gcctgctcanagaagctggcaggactgggaggcgacagatgggcccctcttggcctctgtc ccagctct | 1419 |
| RAN NM_006325 | 6 | S | 181 | 750 | ggatggtgacctgtgagaatgaagctggagcccagcgtcagaagtctagttttataggcag ctgtcc | 816 |
| REL NM_002908 | 2 | S | 182 | 1727 | tgaatcttgaaaaccccctcatgtaattcagtgttagacccaagagacttgagacagctcca tcagatgtcctcttccagtatgtcagcaggcgccaattccaatactactgcccattgtttc acaatcagatgcatttgagggatctgacttcagttgtgcagataacagcatgataaatg | 1906 |
| AHRG NM_001665 .1 | 36 | S | 183 | 518 | aggagcagagccaggcgcccatcacaccgcagcagggccaggcactcgcgaaacagatcc acgctgtgcgctacctcgaatgctcagccctgcaacaggatggtgtcaaggaagtgttcgc cgaggctgtccgggctgtgctc | 660 |
| | 2 | AS | 184 | 377 | ccattgccagtccgccgtcctatgagaacgtgcggcacaagtggcatccagaggtgtgcca ccactgccctgatgtgtgcccatcctgctggtgggcaccaagaaggacctgagagcccagcct gacacccctacggc | 511 |
| | 1 | S | 185 | 518 | aggagcagagccaggcgcccatcacaccgcagcagggccaggcact | 563 |
| | 2 | S | 186 | 273 | ggcaatggagaaacagatgacgaaaacgttggtctgagggtaggagagtgtacggaggcgg tcatactcctcctggcccgcagtgtcccacaggttcaggttcactttgcgc | 384 |
| | 1 | S | 187 | 516 | caccatcctgttgcagggctgagcattcgaggtagcgcacagcgtggatctgcttggccag tgcctggccctgctgcggtgtgatgggcgcctggccctgctccttg | 622 |
| | 1 | S | 188 | 541 | gagcacagcccgacagcctcggcgagctattccttggctccatcgtgttgcagggtggc gtcctaggtagcgcgcagcgtggatatgctcggccagtgcatggccctgatgcggtgt | 660 |
| RPA1 NM_002945 | 2 | AS | 189 | 2163 | tggagaagcaaaaacctagttacataatttacttcatggtctgcagttagggtcagtgactt acgacataattcctgcttgatgataatgaaattgacagaagcctgaaggctgagtgagtga | 2285 |
| RPA3 NM_002947 .1 | 6 | S | 190 | 8 | agccgcagtcttggaccataatcatgg | 34 |
| RPL12 NM_000976 | 2 | S | 191 | 24 | ggccaaggtgcaacttccttcggtcgtcccgaatccgggttcatccgacaccagccgcctc caacatgccgccgaagttcgaccccaacga | 114 |
| RPL31 NM_013403 | 9 | S | 192 | 28 | tggcgagaagaaaaagggccgttctgccatcaacgaagtggtaacccgagaat | 80 |
| .1 | 1 | S | 193 | 44 | ggccgttctgccatcaacgaagtggtaacccgagaat | 80 |
| RPL35 NM_004632 | 2 | AS | 194 | 12 | ggcggcttgtgcagcaatggccaagatcaaggctcgagatct | 53 |
| .1 | 1 | AS | 195 | 12 | ggcggcttgtgcagcaatggccaagatcaaggc | 44 |

TABLE 4-continued

Nucleotide Sequences of GSEs

| Gene/ Accession No. | No. of Clones | Orientation | SEQ ID NO | | Sequence | |
|---|---|---|---|---|---|---|
| RPS24 NM_001026 | 4 | AS | 196 | 351 | gccagcaccaacattggcctttgcagtcccccctgactttcttcattctgttcttgcgttcc t ttcgttgct | 421 |
| | 4 | S | 197 | 373 | cagaatgaagaaagtcaggggactgcaaaggccaatgttggtgctggcaaaaag | 427 |
| RPS29 NM_001032 | 2 | S | 198 | 4 | ttaccctcgttgcactgctgagagcaagatgggtcaccagcagctgtactggagcca | 59 |
| SQSTM1 NM_003900 | 2 | S | 199 | 1278 | ggcagcaaaacaagtgacatgaagggagggtccctgtgtgtgtgtgc | 1324 |
| STAT3 NM_003150 .1 | 11 | S | 200 | 2288 | gagagccaggagcatcctgaagctgacccaggtagcgctgccccatacctgaagaccaagt ttatctgtgtgacaccaacgacctgcagcaataccattgacctgccgatgtccccccgc | 2407 |
| | 7 | AS | 201 | 2111 | aagacccagatccagtccgtggaaccatacacaaagcagcagctgaacaacatgtcatttg ctgaaatcatcatgggctataagatcatggatgctaccaatatcctg | 2218 |
| | 2 | S | 202 | 667 | ggatgtccggaagagagtgcaggatctagaacagaaaatgaaagtggtagagaatctcca ggatgactttgatttcaactataaaaaccctcaagagtc | 764 |
| | 2 | S | 203 | 431 | ttcctgcaagagtcgaatgttctctatcagcacaatctacgaagaatcaagcagtttcttc agagcaggtatcttgagaagccaatggagattgcccggattgtggcccggtgcc | 545 |
| | 1 | AS | 204 | 834 | agatgctcactgcgctggaccagatgcggagaagcatcgtgagtgagctggcggggctttt gtcagcgatggagtacgtgcagaa | 918 |
| | 1 | S | 205 | 413 | gaccagcagtatagccgcttcctgcaagagtcgaatgttctctatca | 459 |
| | 1 | AS | 206 | 935 | gagctggctgactggaagaggcggcaacagatggagtacgtgcagaa | 980 |
| STAT5b NM_012448 .1 | 102 | AS | 207 | 287 | tcttgataatccacaggagaacattaaggccacccagctcctggagggcctggtgcag gagctgcagaagaaggcagaacaccaggtgggggaagatgggttttt | 391 |
| | 1 | AS | 208 | 303 | gagaacattaaggccacccagctcctggagggcctggcgcaggagctgcagaacaaggcac aacaccaggaggggaagatg | 384 |
| | 3 | S | 209 | 1941 | aacaagcagcaggccacgacctgctcatcaacaagccagatgggaccttcctgctgcgct tcagcgactcggaaatcgggggcatcaccattgcttggaagtttga | 2047 |
| | 36 | S | 210 | 1409 | aaacgaatcaagaggtctgaccgccgtggtgcagagtcggtcacggaagagaagttcacaa tcttgtttgactcacagttcagtgttggtggaaatgagctggt | 1513 |
| | 3 | AS | 211 | 287 | tcttgataatcctcaggaggccattaagcccacccagctcatgaagggcatggtgcagtag ctgcagaagaagagcagaactccaggtgggggaagatgggttt | 389 |
| | 1 | AS | 212 | 287 | tcttgataatccacaggagaacattaaggccacccagctcctggaggg | 334 |
| | 2 | S | 213 | 1467 | acaatcctgttttgaatcccagttcagtgttggtggaaatgagctggt | 1513 |
| | 1 | S | 214 | 1484 | ccagttcagtgttggtggaaatgagctggt | 1513 |
| TAF7 (TFIID) NM_005642 | 6 | S | 215 | 65 | cgagctgcgcctctcggcaagatttcgcgctgaccatcccgggccctttcatcactaatcg gt | 127 |
| TDGF1 NM_003212 | 3 | AS | 216 | 57 | ggtcgtagcagaagcaggagcaaggcgtccaggggaaactggagggctt | 105 |
| VWF NM_000552 .2 | 8 | S | 217 | 3646 | ccagcatggcaaggtggtgacctggaggacggccacattgtgcccccagagctgcgaggaga ggaatctccgggagaacgggtatgagtgtgagtggcgctataacagctgtgcacctgcctg | 3768 |
| | 3 | AS | 218 | 4687 | ccttgcccctgaagcccctcctcctactctgccccccacatggcacaagtcactgtgggc ccggggctcttggggggttttcgaccctggggcccaagaggaactccatggttctggatgtgg cgttc | 4813 |
| | 3 | S | 219 | 1124 | gcccggacctgtgcccaggagggaatggtgctgtacggctggaccgaccacagcgcgtgca gcccagtgtgccctgctggtatg | 1207 |
| | 2 | S | 220 | 7776 | agtgctgtggaaggtgcctgccatctgcctgtgaggtggtgactggctcaccgcgggggga ctcccagtcttcctg | 7851 |
| | 2 | S | 221 | 5082 | tggtcagccagggtgaccgggagcaggcgcccaacctggtctacatggtcaccggaaatcc tg | 5144 |
| | 3 | S | 222 | 6003 | agtgccacaccgtgacttgccagccagatggccagaccttgctgaagagtcatcgggtcaa ctgt | 6067 |

TABLE 4-continued

Nucleotide Sequences of GSEs

| Gene/ Accession No. | No. of Clones | Orientation | SEQ ID NO | Sequence | |
|---|---|---|---|---|---|
| | 1 | AS | 223 | 4725 acatggcacaagtcactgtgggcccggggctcttgggggtttcgaccctggggcccaagag gaactccatggttctggatg | 4805 |
| | 2 | S | 224 | 4376 tccaccagcgaggtcttgaaatacacactgttccaaatcttcagcaagatcgaccgccctg aagc | 4440 |
| | 1 | AS | 225 | 7818 ctggctaccgcggggggactcccagtcttcctggaagagtgtcggctcccagtggg | 7874 |
| | 1 | AS | 226 | 1380 accctcccggcacctccctctctcgagactgcaacacctgcatttgccgaaacagcc | 1436 |
| | 2 | AS | 227 | 8762 agctgcatgggtgcctgctgctgcc | 8786 |
| ZIN NM_013403.1 | 6 | AS | 228 | 1782 ctcagtggccttcaccagcaccgagcctgcccacatcgtggcctccttccgctctggcgac accgtcttgtatgacatggaggttggcagtgccctcctcacgctggagtcccggggcagca gcggtccaaccca | 1916 |

TABLE 5

Peptides encoded by sense-oriented GSEs

| Gene | GSE SEQ ID NO | Peptide SEQ ID NO | Location in Parent (AA Protein Residues) | Sequence |
|---|---|---|---|---|
| ADPRT | 24 | 229 | 860–887 | LWHGSRTTNFAGILSQGLRIAPPEAPVT |
| IF1 | 32 | 230 | 1–16 | MAVTALAARTWLGVWG |
| BAG1 | 33 | 231 | 53–80 | RDEESTRSEEVTREEMAAAGLTVTVTVTHS |
| BAG1 | 34 | 232 | 62–80 | EVTREEMAAAGLTVTVTHS |
| AP1B1 | 35 | 233 | 76–97 | YAKSQPDMAIMAVNTFVKDCED |
| AP1B1 | 36 | 234 | 81–96 | PDMAIMAVNTFVKDCE |
| CDK1O | 38 | 235 | 347–360 | APATSEGQSKRCKP |
| CDK2 | 40 | 236 | 51–66 | EISLLKELNHPNIVKL |
| CDK2 | 41 | 237 | 159–177 | YTHEVVTLWYRAPEILLGC |
| c-FOS | 45 | 238 | 362–378 | PELVHYREEKHVFPQRF |
| c-FOS | 47 | 239 | 148–158 | KMAAAKCRNRR |
| CREB1 | 54 | 240 | 27–49 | VQAQPQIATLAQVSMPAAHATSS |
| CCND1 | 55 | 241 | 56–91 | MRKIVATWMLEVCEEQKCEEEVFPLAMN YLDRFLSL |
| EDF1 | 61 | 242 | 22–37 | AKSKQAILAAQRRGGD |
| EIFI | 62 | 243 | 1050–1063 | RGGADDERSSWRNA |
| EFNA1 | 67 | 244 | 53–79 | HYEDHSVADAAMEQYILYLVEHEEYQL |
| FEN1 | 71 | 245 | 90–101 | PQLKSGELAKRS |
| FGFR1 | 76 | 246 | 427–470 | VTVSADSSASMNSGVLLVRPSRLSSSGTPMLAGVSEYELPEDPR |
| FGFR1 | 78 | 247 | 402–421 | GTKKSDFHSQMAVHKLAKSI |
| GBC1 | 79 | 248 | 36–54 | LTSQTMGGQAETLLTSQKG |
| FOS2L | 83 | 249 | 246–261 | IKPISIAGGFYGEEPL |
| GSTP | 97 | 250 | 83–102 | DQQEAALVDMVNDGVEDLRC |

TABLE 5-continued

Peptides encoded by sense-oriented GSEs

| Gene | GSE SEQ ID NO | Peptide SEQ ID NO | Location in Parent (AA Protein Residues) | Sequence |
|---|---|---|---|---|
| GSTP | 98 | 251 | 170–210 | CLDAFPLLSAYVGRLSARPKLKAFLASPEYVNLPINGNGKQ |
| GBC-3 | 94 | 252 | | WMDGRDEVTQQKYQRPETEWPRVSLHPEPEDAAKTSLSE |
| HES6 | 99 | 253 | 874–948 | RAAPGNQPSQAPAPFLKKLLGTLQL |
| HNRPA2B1 | 100 | 254 | 786–866 | ISDQDQEVTLEEDLMDMAVDVDLGMAI |
| HNRPF | 101 | 255 | 226–278 | AGLERMRPGAYSTGYGGYEEYSGLSDGYGFTTDLFGRDLSYCL SGMYDHRYGD |
| HRMT1L2 | 102 | 256 | 2701–2748 | GVGAGEDGGSRGRELH |
| HSPCA | 103 | 257 | 499–515 | KDQVANSAFVERLRKHG |
| ICAM2 | 105 | 258 | 1–19 | MSSFGYRTLTVALFTLICC |
| ICAM2 | 106 | 259 | 216–229 | YEPVSDSQMVIIVT |
| IGF2R | 108 | 260 | 253–265 | KLVRKDRLVLSYV |
| IGF2R | 109 | 261 | 481–496 | KKRYDLSALVRHAEPE |
| INTB5 | 111 | 262 | 12–56 | LLGLCALLPRLAGLNICTSGSATSCEECLLIHPKCAWCSKEDFGS |
| INTB5 | 112 | 263 | 688–724 | KDCVMMFTYVELPSGKSNLTVLREPECGNTPNAMTIL |
| INTB5 | 113 | 264 | 457–485 | GHGECHCGECKCHAGYIGDNCNCSTDIST |
| INTB5 | 114 | 265 | 697–726 | VELPSGKSNLTVLREPECGNTPNAMTILLA |
| ITGA4 | 119 | 266 | 18–41 | PEAAVRETVMLLLCLGVPTGRPYN |
| JUNB | 121 | 267 | 19–34 | GYGRAPGGLSLHDYKL |
| JUNB | 122 | 268 | 24–32 | PGGLSLHDY |
| L1CAM | 127 | 269 | 457–491 | SVQWLDEDGTTVLQDERFFPYANGTLGIRDLQAND |
| L1CAM | 129 | 270 | 216–251 | TRTIIQKEPIDLRVKATNSMIDRKPRLLFPTNSSSH |
| L1CAM | 130 | 271 | 191–220 | GNLYFANVLTSDNHSDYICHAHFPGTRTII |
| L1CAM | 132 | 272 | 450–469 | AFGAPVPSVQWLDEDGTTVL |
| L1CAM | 134 | 273 | 25–39 | EYEGHHVMEPPVITE |
| L1CAM | 131 | 274 | 79–91 | KEELGVTVYQSPH |
| L1CAM | 133 | 275 | 237–253 | DRKPRLLFPTNSSSHLV |
| PSMB7 | 139 | 276 | 193–211 | EAKNLVSEAIAAGIFNDLG |
| MCM3 | 145 | 277 | 519–543 | PLGSAVDILATDDPNFSQEDQQDTQ |
| MCM3 | 148 | 278 | 789–802 | LSKMQDDNQVMVSE |
| MCM6 | 151 | 279 | 690–711 | PAPVNGINGYNEDINQESAPKA |
| MET | 154 | 280 | 1253–1317 | YSVHNKTGAKLPVKWMALESLQTQKFTTKSDVWS FGVVLWELMTRGAPPYPDVNTFDITVYLLQG |
| MYL6 | 155 | 281 | 2–23 | MCDFTEDQTTEFKEAFQLFDRT |
| MYL6 | 156 | 282 | 7–32 | EDQTTEFKEAFQLFDRTGDGKILYNQ |
| NR3C1 | 159 | 283 | 132–155 | STSVPENPKSSASTAVSAAPTEKE |
| NUMA1 | 160 | 284 | 1314–1332 | ELTSQAERAEELGQELKAW |

TABLE 5-continued

Peptides encoded by sense-oriented GSEs

| Gene | GSE SEQ ID NO | Peptide SEQ ID NO | Location in Parent (AA Protein Residues) | Sequence |
|---|---|---|---|---|
| GRP58 | 161 | 285 | 360–382 | NLKRYLKSEPIPESNDGPVKVVV |
| PC4 | 163 | 286 | 32–49 | APEKPVKKQKTGETSRAL |
| PKC delta | 165 | 287 | 281–322 | GINQKLLAEALNQVTQRASRRSDSASSEPVGIYQGFEKKTGV |
| PKC delta | 166 | 288 | 204–239 | IIGRCTGTAANSRDTIFQKERFNIDMPHRFKVHNYM |
| PKC eta | 168 | 289 | 55–84 | GQTSTKQKTNKPTYNEEFCANVTDGGHLEL |
| PKC eta | 169 | 290 | 73–106 | CANVTDGGHLELAVFHETPLGYDHFVANCTLQFQE |
| PKCzeta | 172 | 291 | 130–148 | GHLFQAKRFNRRAYCGQCS |
| PKC zeta | 173 | 292 | 55–94 | PLTLKWVDSEGDPCTVSSQMELEEAFRLARQCRDEGLIIH |
| RAB2L | 177 | 293 | 291–321 | VTQFNKVAGAVVSSVLGATSTGEGPGEVTIR |
| REL | 182 | 294 | 518–553 | NLENPSCNSVLDPRDLRQLHQMSSSSMSAGANSNTT |
| AHRG | 183 | 295 | 131–177 | EQSQAPITPQQGQALAKQIHAVRYLECSALQQDGVKEVFAEAVRAVL |
| AHRG | 186 | 296 | 49–85 | GWMEEQSQAPITPQQGQALE |
| AHRG | 187 | 297 | 130–164 | KEQSQAPITPQQGQALAKQIHAVRYLECSALQQDG |
| AHRG | 188 | 298 | 138–155 | TPQQGQALAKQIHAVRYL |
| RPL12 | 191 | 299 | 209–228 | SRIRVHLTPAASTMLPKFNP |
| RPL31 | 192 | 300 | 8–24 | GEKKKGRSAINEVVTRE |
| RPS24 | 197 | 301 | 113–130 | WMDGRMKKVRGTAKANVGAGKK |
| STAT3 | 200 | 302 | 6150–729 | ESQEHPEADPGSAAPYLKTKFICVTPTTCSNTIDLPMSPR |
| STAT3 | 202 | 303 | 90–181 | DVRKRVQDLEQKMKVVENLQDDFDFNYKTLKS |
| STAT3 | 203 | 304 | 71–108 | FLQESNVLYQHNLRRIKQFLQSRYLEKPMEIARIVARC |
| STAT3 | 205 | 305 | 65–79 | DQQYSRFLQESNVLY |
| STAT5 | 209 | 306 | 599–633 | NKQQAHDLLINKPDGTFLLRFSDSEIGGITIAWKF |
| STAT5 | 210 | 307 | 422–455 | KRIKRSDRRGAESVTEEKFTILFESQFSVGGNEL |
| STAT5 | 213 | 308 | 441–455 | TILFESQFSVGGNEL |
| VWF | 217 | 309 | 1113–1152 | QHGKVVTWRTATLCPQSCEERNLRENGYECEWRYNSCAPA |
| VWF | 219 | 310 | 272–299 | ARTCAQEGMVLYGWTDHSACSPVCPAGM |
| VWF | 220 | 311 | 2490–2513 | CCGRCLPSACEVVTGSPRGDSQSS |
| VWF | 221 | 312 | 1592–1611 | VSQGDREQAPNLVYMVTGNP |
| VWF | 222 | 313 | 1899–1919 | CHTVTCQPDGQTLLKSHRVNC |
| VWF | 224 | 314 | 1356–1376 | STSEVLKYTLFQIFSKIDRPE |

We claim:

1. A method for identifying a compound that inhibits growth of a mammalian cell, the method comprising the steps of:
   (a) culturing a cell in the presence or absence of the compound;
   (b) assaying the cell for expression or activity of L1CAM (L1 cell adhesion molecule, ICAM2 (intercellular cell adhesion molecule-2), NIN283, ATF4, Zinedin, GBC-1 (Growth of Breast Carcinoma 1), GBC-3 (Growth of Breast Carcinoma 3), and GBC-11 (Growth of Breast Carcinoma 11); and
   (c) identifying the compound when expression or activity of L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) is lower in the presence of the compound than in the absence of the compound.

2. A method according to claim 1, wherein the cell is a tumor cell.

3. A method according to claim 2, wherein the cell is a human tumor cell.

4. A method according to claim 1, further comprising the step of comparing cell growth in the presence of the compound with cell growth in the absence of the compound.

5. The method of claim 1, where expression of L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) is detected by hybridization to a complementary nucleic acid.

6. The method of claim 1, wherein expression of L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) is detected using an immunological reagent.

7. The method of claim 1, wherein expression of L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) is detected by assaying for an activity of the L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) gene product.

8. A method according to claim 1, wherein expression of L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) is assayed using a recombinant mammalian cell comprising a reporter gene operably linked to a promoter from L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) and detecting decreased expression of the reporter gene in the presence of the compound than in the absence of the compound.

9. The method of claim 8, further comprising the step of assaying cell growth in the presence and absence of the compound and identifying compounds that inhibit cell growth and L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11).

10. A method according to claim 9, wherein the cell is a tumor cell.

11. A method according to claim 10, wherein the cell is a human tumor cell.

12. The method of claim 9, where expression of L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) is detected by hybridization to a complementary nucleic acid.

13. The method of claim 9, wherein expression of L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) is detected using an immunological reagent.

14. The method of claim 9, wherein expression of L1CAM (L1 cell adhesion molecule), ICAM2 (intercellular cell adhesion molecule-2), NIN283, ATF4, Zinedin, GBC-1 (Growth of Breast Carcinoma 1), GBC-3 (Growth of Breast Carcinoma 3), or GBC-11 (Growth of Breast Carcinoma 11) is detected by assaying for an activity of the cellular gene product.

* * * * *